US007767424B2

(12) United States Patent
Qu et al.

(10) Patent No.: US 7,767,424 B2
(45) Date of Patent: Aug. 3, 2010

(54) CLONING AND CHARACTERIZATION OF THE BROAD-SPECTRUM RESISTANCE GENE PI2

(75) Inventors: Shaohong Qu, Davis, CA (US); Guo-liang Wang, Columbus, OH (US); Bo Zhou, Columbus, OH (US)

(73) Assignee: The Ohio State University, Columbus, OH (US)

( * ) Notice: Subject to any disclaimer, the term of this patent is extended or adjusted under 35 U.S.C. 154(b) by 573 days.

(21) Appl. No.: 11/472,042

(22) Filed: Jun. 21, 2006

(65) Prior Publication Data

US 2006/0228751 A1 Oct. 12, 2006

Related U.S. Application Data

(63) Continuation of application No. 10/656,394, filed on Sep. 5, 2003, now Pat. No. 7,094,951.

(60) Provisional application No. 60/455,713, filed on Mar. 18, 2003, provisional application No. 60/409,216, filed on Sep. 9, 2002.

(51) Int. Cl.
*C12Q 1/68* (2006.01)
*C12P 19/34* (2006.01)

(52) U.S. Cl. ......................... 435/91.2; 435/6; 435/91.1

(58) Field of Classification Search ....................... None
See application file for complete search history.

(56) References Cited

U.S. PATENT DOCUMENTS

| | | | |
|---|---|---|---|
| 5,677,175 | A | 10/1997 | Hodges et al. |
| 6,274,789 | B1 | 8/2001 | Yano et al. |
| 6,479,731 | B1 | 11/2002 | Valent et al. |
| 2002/0108140 | A1 | 8/2002 | Bennetzen |
| 2004/0006788 | A1 | 1/2004 | Wang et al. |

FOREIGN PATENT DOCUMENTS

| | | |
|---|---|---|
| JP | 10-262682 | 6/1998 |
| WO | WO 02/34927 | 5/2002 |

OTHER PUBLICATIONS

Bryan, G.T., "A Single Amino Acid Difference Distinguishes Resistant and Susceptible Alleles of the Rice Blast Resistance Gene *Pi-ta,*" *The Plant* Cell, 2000, pp. 2033-2045, vol. 12.

GenBank Accession No. AB026839, Oct. 31, 1999.

GenBank Accession No. AF207842, Feb. 1, 2001.

GenBank Accession No. L32142, May 23, 1994.

Amante-Bordeos, A., et al., "Transfer of Bacterial Blight and Blast Resistance From the Tetraploid Wild Rice *Oryza minuta* to Cultivated Rice, *Oryza sativa,*" *Theor. Appl. Genet.* 1992, pp. 345-354, vol. 84.

Bent, A., "Plant Disease Resistance Genes: Function Meets Structure," *The Plant Cell*, 1996, pp. 1757-1771, vol. 8.

Bryan, G.T., et al., "A Single Amino Acid Difference Distinguishes Resistant and Susceptible Alleles of the Rice Blast Resistance Gene *PI-ta," The Plant Cell*, 2000, pp. 2033-2045, vol. 12.

Jia, Y., et al., "Direct Integration of Resistance Gene and Avirulence Gene Products Confers rice Blast Resistance," *The EMBO Journal*, 2000, pp. 4004-4014, vol. 19(15).

Chen, D.H., et al., "Phenotypic Characterization of the Rice Blast Resistance Gene *Pi-2(t)*," *Plant Disease*, 1996, pp. 52-56, vol. 80(1).

Hittalmani, S., et al., "Fine Mapping and DNA Marker-Assisted Pyramiding of the Three Major Genes for Blast Resistance in Rice," *Theor. Appl. Genet.*, 2000, pp. 1121-1128, vol. 100.

Liu, G., et al., "Two Broad-Spectrum Blast Resistance Genes, *Pi9(t)* and *Pi2(t)*, are Physically Linked on Rice Chromosome 6," *Mol. Genet. Genomics*, 2002, pp. 472-480, vol. 267.

Mackill, D.J. and J.M. Bonman, "Inheritance of Blast Resistance in Near-Isogenic Lines of Rice," *The American Phytopathological Society*, 1992, pp. 746-749, vol. 82(7).

Moffat, A.S., "Mapping the Sequence of Disease Resistance," *Science*, 1994, pp. 1804-1805, vol. 256.

Parker, et al. "Characterization of *eds*1, a Mutation in Arabidopsis Suppressing Resistance to *Peronospora parasitica* Specified by Several Different *RPP* Genes," *Plant Cell*, 1996, pp. 2033-2046, vol. 8.

Wang, Z., et al., "The *Pib* Gene for Rice Blast Resistance Belongs to the Nucleotide Binding and Leucine-rich Repeat Class of Plant Disease Resistance Genes," *The Plant Journal*, 1999, pp. 55-64, vol. 19(1).

Yu, Z.H., et al., "Tagging Genes for Blast Resistance in Rice via Linkage to RFLP Markers," *Theor. Appl. Genet.* 1991, pp. 471-476, vol. 81.

*Primary Examiner*—Young J Kim

(74) *Attorney, Agent, or Firm*—Alston & Bird LLP

(57) ABSTRACT

Methods for enhancing or creating plant disease resistance to plant pests are provided. Transforming a plant with a novel rice Pi2-like disease resistance gene of the invention enhances disease resistance of the plant.

7 Claims, 8 Drawing Sheets

Multiple sequence alignment of NBS1, 2, 4, 6 with Cloned blast resistance gene Pib

```
NBS2    ------------------------------------------------------------
NBS4    ------------------------------------------------------------
NBS6    ------------------------------------------------------------
NBS1    ------------------------------------------------------------
Pib     MMRSFMMEAHEEQDNSKVVKTWVKQVRDTAYDVEDSLQDFAVHLKRPSWWRFPRTLLERH

NBS2    -----------------------------------MAETVLSMARSLVGSAISKAASAAA
NBS4    -----------------------------------MAETVLSMARSLVGSAISKAASAAA
NBS6    -----------------------------------MAETVLSMARSLVGSAISKAASAAA
NBS1    ----------------------------------MAAETVVSMAMSVLGSAVGKAASAAA
Pib     RVAKQMKELRNKVEDVSQRNVRYHLIKGSAKATINSTEQSSVIATAIFGIDDARRAAKQD
                                            :*   :* ::.*   .: *:

NBS2    NETSLLLGVEKD------------------------------------------------
NBS4    DETSLLLGVEKD------------------------------------------------
NBS6    DETSLLLGVEKD------------------------------------------------
NBS1    DEATLLLGIQKE------------------------------------------------
Pib     NQRVDLVQLINSEDQDLKVIAVWGTSGDMGQTTIIRMAYENPDVQIRFPCRAWVRVMHPF
        ::   *: : :.

NBS2    -----IWYIKDELKTMQAFLRAAEXMKKKDELLKVWAEQIRDL----------SYDIEDS
NBS4    -----IWYIKDELKTMQAFLRAAELMKKKDELLKVWAEQIRDL----------SYDIEDS
NBS6    -----IWYL---------------------------------------------------
NBS1    -----IWYIKDELKTIQAFLRAAEVTKKKDDLLKVWAEQVRDL----------SYNIEDC
Pib     SPRDFVQSLVNQLHATQGVEALLEKEKTEQDLAKKFNGCVNDRKCLIVLNDLSTIEEWDQ
             :  : ..  : ..     .  .....  .        .            :  .  .

NBS2    LDEFKVHIESQTLFRQLVKLRERHRIAIRIHNLKSRVEEVSSRNTRYNLVEPISSG-TED
NBS4    LDEFKVHIESQTLFRQLVKLRERHRIAIRIHNLKSRVEEVSSRNTRYSLVKPISSG-TEI
NBS6    ----------------------FRHGVGRSNGGPVVGMVASGNQ------------SCL
NBS1    LDEFKVHVESQSLAKQLMKLGERHRIAVQIRNLKSRIEEVSNRNTRYSLIKPISSITTED
Pib     IKKCFQKCRKGSRIIVSSTQVEVASLCAGQESQASELKQLSADQTLYAFYDKGSQIIEDS
         ..       . :      .  .              .  . :  ::  :       .  :.

NBS2    DMDSYAEDIRNQSARN-----------------------------------VDEAELVGF
NBS4    DMDSYAEDIRNQSARN-----------------------------------VDEAELVGF
NBS6    AIDSYAEDIRNQSARN-----------------------------------VDEAELVGF
NBS1    ERDSYLEDARNRSGSN-----------------------------------TDESELVGF
Pib     VKPVSISDVAITSTNNHTVAHGEIIDDQSMDADEKKVARKSLTRIRTSVGASEESQLIGR
           .*    *   *                                      :*::*:*

NBS2    SDSKKRLLEMIDTNANDGPAKVICVVGMGGLGKTALSRKIFESEEDIRKNFPCNAWITVS
NBS4    SDSKKRLLEMIDTNANDGPAKVICVVGMGGLGKTALSRKIFESEEDIRKNFPCNAWITVS
NBS6    SDSKKRLLEMIDTNANDGPAKVICVVGMGGLGKTALSRKIFESEEDIRKNFPCNAWITVS
NBS1    AKTKDELLKLIDVNTNDGPAKVICVVGMGGLGKTTLARKAYENKEHM-KNFSCCAWITVS
Pib     EKEISEITHLILNNDSQ-QVQVISVWGMGGLGKTTLVSGVYQS-PRLSDKFDKYVFVTIM
         .  ..: .:*  * .:. .:**.* ********:*     ::..  : .:*   .::*:

NBS2    QSFHRIELLKDMIRQLLGPSS-----LDQLLHELQGKVVVQVHHLSEYLIEELKEKRYFV
NBS4    QSFHRIELLKDMIRQLLGPSS-----LDQLLQELQGKVVVQVHHLSEYLIEELKEKRYFV
NBS6    QSFHRIELLKDMIRQLLGPSS-----LDQLLQELQGKVVVQVHHLSEYLIEELKEKRYFV
NBS1    QSFDRKEILKQMIRQLLGADS-----LDKLLKEFSEKLLVQVQHLADHLVEGLKEKRYFV
Pib     RPFILVELLRSLAEQLHKGSSKKEELLENRVSSKKSLASMEDTELTGQLKRLLEKKSCLI
        :.*   *:*:.: .**    .*     *:: :  . .    ::  .*:  * . *::*  ::

NBS2    VLDDLWILHDWNWINEIAFPKNNKKGSRIVITTRNVDLAEKCATAS-LVYHLDFLQMNDA
```

FIGURE 5A

```
NBS4     VLDDLWILHDWNWINEIAFPKNNKKGSRIVITTRNVDLAEKCATAS-LVYHLDFLQMNDA
NBS6     VLDDLWILHDWNWINEIAFPKNNKKGSQIVITTWNVDLAEKCATAS-LVYHLDFLQMNDA
NBS1     VLDDLWTIDAWNWIHDIAFPKINNRGSRIIITTRDAGLAGRCTSES-LIYHLEPLHIDDA
Pib      VLDDFSDTSEWDQIKPTLFP-LLEKTSRIIVTTRKENIANHCSGKNGNVHNLKVLKHNDA
         ****:      *: *:   **.  :: *:*::** . .:* :*:   .  :::*. *: :**

NBS2     ISLLLRKTNKNHEDME--SNKNMQKMVERIVNKCGRLPLAILTIGAVLAT--KQVSEWEK
NBS4     ITLLLRKTNKNHEDME--SNKNMQKMVERIVNKCGRLPLAILTIGAVLAT--KQVSEWEK
NBS6     ITLLLRKTNKNHEDME--SNKNMQKMVERIVNKCGRLPLAILTIGAVLAT--KQVSEWEK
NBS1     IHLLLAKTNIRLEDME--NDEDLGSIVTKLVKRCGYLPLAILTIGGILAT--KKIMEWGK
Pib      LCLLSEKVFEEATYLDDQNNPELVKEAKQILKKCDGLPLAIVVIGGFLANRPKTPEEWRK
         : **  *.  .    ::  .: :: . . :::::*. *****:.**..**.  *   ** *

NBS2     FYEQLPSELEINPSLEALRRMVTLGYNHLPSHLKPCFLYLSIFPEDFEIQRNRLVGRWIA
NBS4     FYEHLPSELEINPSLEALRRMVTLGYNHLPSHLKPCFLYLSIFPEDFEIKRNRLVGRWIA
NBS6     FYEHLPSELEINPSLEALRRMVTLGYNHLPSHLKPCFLYLSIFPEDFEIKRNRLVGRWIA
NBS1     FYRELPSELESNPSLEAMRRMVTLSYNHLPSHLKPCFLYLSIFPEDFEIQRGRLVDRWIA
Pib      LNENINAELEMNPELGMIRTVLEKSYDGLPYHLKSCFLYLSIFPEDQIISRRRLVHRWAA
         : ..: :*** **.*  :* ::  .*: ** ***.***********  *.* *** ** *

NBS2     EGFVRPKVGMTTKDVGESYFNELINRSMIQRSRVGTAG--KIKTCRIHDIIRDITVSISR
NBS4     EGFVRPKVGMTTKDVGESYFNELINRSMIQRSRVGIAG--KIKTCRIHDIIRDITVSISR
NBS6     EGFVRPKVGMTTKDVGESYFNELINRSMIQRSRVGIAG--KIKTCRIHDIIRDITVSISR
NBS1     EGFVRATDGVNIEDVGNSHFNELINRSLIQPSKVSTDG--VVKRCRIHDIMRDIIVSISR
pib      EGYSTAAHGKSAIEIANGYFMELKNRSMILPFQQSGSSRKSIDSCKVHDLMRDIAISKST
         **:  .  * .  ::.:.:* ** ***:*    : .  .    :. *::**::*** :* *

NBS2     QENFVLLPMGDGSDLVQENTRHIAFHGSMSCKTG-----LDWSIIRSLAIFGDRPKSLAH
NBS4     QENFVLLPMGDGSDLVQENTRHIAFHGSMSCKTG-----LDWSIIRSLAIFGDRPKSLAH
NBS6     QENFVLLPMGDGSDLVQENTRHIAFHGSMSCKTG-----LDWSIIRSLAIFGDRPKSLAH
NBS1     EENFVLLTREKITVVAEESIRHLAFHGSKCSKIC-----LEWNHLRSVTLFGDRPVGRTP
pib      EENLVFRVEEGCSAYIHGAIRHLAISSNWKGDKSEFEGIVDLSRIRSLSLFG----DWKP
         :**:*:       :    .   **:*: ..    .        :: . :**:::**. . .

NBS2     AVCPDQLRMLRVLDLEDVTFLITQKDFDRIALLCHLKYLSIGYSSSIYSLPRSIGKLQGL
NBS4     AVCPDQLRMLRVLDLEDVTFLITQKDFDRIALLCHLKYLSIGYSSSIYSLPRSIGKLQGL
NBS6     AVCPDQLRMLRVLDLEDVTFLITQKDFDRIALLCHLKYLSIGYSSSIYSLPRSIGKLQGL
NBS1     ALCSPQFRMLRVLDLEDAKFKFTQNDIRNIGLLRHMKYLNFARASTIYTLPRSIGKLQCL
pib      FFVYGKMRFIRVLDFEGTRG-LEYHHLDQIWKLNHLKFLSLRGCYRIDLLPDLLGNLRQL
              ::*::****:*..   :   :.: .*  * *:*:*.:    .   *  **  :*:*: *

NBS2     QTLNMSSTYIAALPSEISKLQCLHTLRCIREL-----EFDNFSLN-HPMKCITNTICLPK
NBS4     QTLNMPSTYIAALPSEISKLQCLHTLRCIGQF-----HYDNFSLN-HPMKCITNTICLPK
NBS6     QTLNMPSTYIAALPSEISKLQCLHTLRCSRKF-----VSDNFSLN-HPMKCITNTICLPK
NBS1     QILNMREANISALTTEVTKLQNLRSLRCSRRS-----GSGYFSIIDNPKECLMITMCLPM
pib      QMLDIRGTYVKALPKTIIKLQKLQYIHAGRKTDYVWEEKHSLMQRCRKVGCICATCCLPL
         * *::  : : **.. : *** *: ::.  .                :     .   *:  * ***

NBS2     VFTPLVSRDNRAKQIAEFHMATKSFWS-------ESFGVKVPKGIGKLRDLQVLEYVDIR
NBS4     VFTPLVSRDDRAKQIAELHMATKSCWS-------ESIGVKVPKGIGKLRDLQVLEYVDIR
NBS6     VFTPLVSRDDRAIQIAELHMATKSCWY-------KSFGVKVPKGIGKLRDLQVLEYVDIR
NBS1     VFLTSINFSDRVKLIPEICMSCSTRWS-------DTKGVRVPRGIDNLKELQILEVVDIN
pib      LCEMYGPLHKALARRDAWTFACCVKFPSIMTGVHEEEGAMVPSGIRKLKDLHTLRNINVG
         :          .          ::     :         .  *. ** ** :*::*: *. :::

NBS2     RTSSRAIKELGQLSKLRKLAVITKGSTKEKCKILYAAIEKLSSLQSLYMNAALLSDIETL
NBS4     RTSSRAIKELGQLSKLRKLGVTTNGSTKEKCKILYAAIEKLSSLQSLHVDAAGISDGGTL
NBS6     RTSSRAIKELGQLSKLRKLGVMTNGSTKEKCKILCAAIEKLSSLQYLYVNAAGISDGGTL
NBS1     RTSRKAIEELGELIQLRKLSVTTKGATNKKYQIFCAAIEKLSSLQSLRVDAEGFSDTGTL
pib      RGN-AILRDIGMLTGLHKLGVAG--INKKNGRAFRLAISNLNKLESLSVSSAGMP--GLC
         * .    :.::* *   *:**.*   .. .::: : :   **.:*..*: * :.:   :..
```

FIGURE 5B

```
NBS2     ECLDSISSPPPLLRTLGLNGSLEEMPNWIEQLTHLKKFNLWSSKLKE-GKNMLILGALP-
NBS4     ECLDSISSPPPLLRTLVLDGILEEMPNWIEQLTHLKKIYLLRSKLKE-GKTMLILGALP-
NBS6     ECLDSISSPPPLLRTLVLYGSLEEMPNWIEQLTHLKKIYLLRSKLKE-GKTMLILGALP-
NBS1     EWLNSIACPPPFLKRLKLNGSLADTPNWFGNLKQLVKMCLSRCGLKD-GKTMEILGALP-
pib      GCLDDISSPPENLQSLKLYGSLKTLPEWIKELQHLVKLKLVSTRLLEHDVAMEFLGELPK
           *:.*:.**  *: * * * *  *:*: :* :* *: *    * : .  * :** **

NBS2     -NLMFLSLYHNSYLGEKLVFKTGAFPNLRTLVIFNLDQLREIRFEDGSSPQLEKIEIS-C
NBS4     -NLMVLHLYRNAYLGEKLVFKTGAFPNLRTLWIYELDQLREIRFEDGSSPLLEKIEIG-E
NBS6     -NLMVLDLYRKAYLGEKLVFKTGAFPNLRTLSIYDLDQLREIRFEDGSSPQLEKIEIR-F
NBS1     -NLMVLRLYRNAYADEKMTFRRGTFPNLRCLDIYLLKQLREIRFEEGTSPTMESIEIY-G
pib      VEILVISPFKSEEIHFKPPQTGTAFVSLRVLKLAGLWGIKSVKFEEGTMPKLERLQVQGR
          ::::.:  ::.      *      :* .** * :  *  ::.::**:*: * :* :::

NBS2     CRLESGIIGIIHLPRLKEISLEYKSKVARLGQLKGEVNTHPNRPVLRMDSDRRDHDLGAE
NBS4     CRLESGITGIIHLPKLKEIPIRYGSKVAGLGQLEGEVNAHPNRPVLLMYSDRRYHDLGAE
NBS6     CRLESGIIGIIHLPRLKEISLGYESKVAGLAQLEGEVRTHPNHPVLRKREDRSDHDLACD
NBS1     CRLESGIIGIKHLPRLKIISLEYDGKVAKLDVLQEEVNTHPNHTELQMAEDRSHHDLGGL
pib      IENEIGFSGLEFLQNINEVQLSVWFPTDHDRIRAARAAGADYETAWEEEVQEARRKGGEL
          . * *: *: .* .:: : :      .        ..      ..       :.  :. .

NBS2     AEGSSIEVQTADPVPDAQGSVTVAVEATDP-------LPEQEGES---------------
NBS4     AEGSSIEVQTADPVPDAEGSVTVAVEATDP-------LPEQEGES---------------
NBS6     AEGSPVEVEATDPLPEQEGESSQRRDKHSSSWFYQVMISSSIGISGRPCFCGCAHLAVPR
NBS1     ASDG---------DDAHDNPALRYQTSC--------------------------------
pib      KRKIR---------EQLARNPNQPIIT---------------------------------
                      :

NBS2     --SQSQVITLTTNDSEEIGTAQAG-----------------
NBS4     --SQSQVITLTTNDSEEIGTAQAG-----------------
NBS6     RGADLRRLPLSSIASHALDSSLSGMNCFNLTFSRDMLLVPA
NBS1     -----------------------------------------
pib      -----------------------------------------
```

FIGURE 5C

SEQUENCE LISTING

```
<160> NUMBER OF SEQ ID NOS: 43

<210> SEQ ID NO 1
<211> LENGTH: 2982
<212> TYPE: DNA
<213> ORGANISM: Oryza minuta
<220> FEATURE:
<221> NAME/KEY: CDS
<222> LOCATION: (1)...(2982)

<400> SEQUENCE: 1

atg gcg gcg gag acg gtg gtg agc atg gcg atg tcg gtg ctg ggc agc       48
Met Ala Ala Glu Thr Val Val Ser Met Ala Met Ser Val Leu Gly Ser
1               5                   10                  15

gcc gtc ggg aag gcc gcc tcc gcc gcc gcc gac gag gcc acc ctc ctg       96
Ala Val Gly Lys Ala Ala Ser Ala Ala Ala Asp Glu Ala Thr Leu Leu
            20                  25                  30

ctc ggc atc cag aag gag atc tgg tac atc aag gac gag ctg aaa act      144
Leu Gly Ile Gln Lys Glu Ile Trp Tyr Ile Lys Asp Glu Leu Lys Thr
        35                  40                  45

att cag gca ttc tta aga gct gct gaa gta aca aag aag aaa gat gac      192
Ile Gln Ala Phe Leu Arg Ala Ala Glu Val Thr Lys Lys Lys Asp Asp
    50                  55                  60

ttg cta aag gta tgg gca gag caa gta cga gat ctg tca tat aac att      240
Leu Leu Lys Val Trp Ala Glu Gln Val Arg Asp Leu Ser Tyr Asn Ile
65                  70                  75                  80

gaa gat tgc cta gac gaa ttc aag gtt cat gtt gag agc caa agc ttg      288
Glu Asp Cys Leu Asp Glu Phe Lys Val His Val Glu Ser Gln Ser Leu
                85                  90                  95

gca aag caa cta atg aag ctt ggt gaa cgc cat cga att gct gta cag      336
Ala Lys Gln Leu Met Lys Leu Gly Glu Arg His Arg Ile Ala Val Gln
            100                 105                 110

att cgc aac tta aaa tca aga att gaa gaa gtg agc aac agg aat aca      384
Ile Arg Asn Leu Lys Ser Arg Ile Glu Glu Val Ser Asn Arg Asn Thr
        115                 120                 125
```

-continued

```
cgc tac agc tta atc aag ccc att tcc tct ata acc aca gag gat gag      432
Arg Tyr Ser Leu Ile Lys Pro Ile Ser Ser Ile Thr Thr Glu Asp Glu
    130                 135                 140

agg gat tcc tac cta gaa gat gct cgc aat cga tca ggt agc aac act      480
Arg Asp Ser Tyr Leu Glu Asp Ala Arg Asn Arg Ser Gly Ser Asn Thr
145                 150                 155                 160

gac gag tca gaa ctt gtg ggc ttt gcc aag act aaa gat gag ttg ctt      528
Asp Glu Ser Glu Leu Val Gly Phe Ala Lys Thr Lys Asp Glu Leu Leu
                165                 170                 175

aaa ctg ata gat gtc aat act aat gac ggt cca gct aaa gtg ata tgt      576
Lys Leu Ile Asp Val Asn Thr Asn Asp Gly Pro Ala Lys Val Ile Cys
            180                 185                 190

gtg gtt ggt atg ggt gga tta ggc aag act acc ctt gca agg aag gca      624
Val Val Gly Met Gly Gly Leu Gly Lys Thr Thr Leu Ala Arg Lys Ala
        195                 200                 205

tat gaa aac aag gaa cac atg aag aac ttc tcg tgt tgt gct tgg atc      672
Tyr Glu Asn Lys Glu His Met Lys Asn Phe Ser Cys Cys Ala Trp Ile
    210                 215                 220

act gtg tct cag tca ttt gac agg aaa gaa att ctg aaa caa atg atc      720
Thr Val Ser Gln Ser Phe Asp Arg Lys Glu Ile Leu Lys Gln Met Ile
225                 230                 235                 240

agg caa ctt ctg ggt gct gat tca tta gac aaa ctc ttg aaa gaa ttt      768
Arg Gln Leu Leu Gly Ala Asp Ser Leu Asp Lys Leu Leu Lys Glu Phe
                245                 250                 255

agt gag aag ttg ctc gtg caa gtc cag cat ctc gct gat cac ttg gtt      816
Ser Glu Lys Leu Leu Val Gln Val Gln His Leu Ala Asp His Leu Val
            260                 265                 270

gaa ggg cta aag gag aaa agg tac ttt gtt gtc ctt gat gac cta tgg      864
Glu Gly Leu Lys Glu Lys Arg Tyr Phe Val Val Leu Asp Asp Leu Trp
        275                 280                 285

acc ata gat gca tgg aat tgg att cat gat att gct ttt ccg aag att      912
Thr Ile Asp Ala Trp Asn Trp Ile His Asp Ile Ala Phe Pro Lys Ile
    290                 295                 300

aac aac aga ggt agt cgc ata ata ata aca acg cga gat gct ggc tta      960
Asn Asn Arg Gly Ser Arg Ile Ile Ile Thr Thr Arg Asp Ala Gly Leu
305                 310                 315                 320

gct gga agg tgt acc tct gaa tca ctt att tac cac ctt gaa ccg tta     1008
Ala Gly Arg Cys Thr Ser Glu Ser Leu Ile Tyr His Leu Glu Pro Leu
                325                 330                 335

cat ata gat gat gct ata cac ttg cta cta gca aag aca aac ata aga     1056
His Ile Asp Asp Ala Ile His Leu Leu Leu Ala Lys Thr Asn Ile Arg
            340                 345                 350

ctt gaa gac atg gaa aat gat gag gac ttg ggc agc ata gtt aca aaa     1104
Leu Glu Asp Met Glu Asn Asp Glu Asp Leu Gly Ser Ile Val Thr Lys
        355                 360                 365

ttg gtg aaa agg tgt ggt tat tta ccg ctg gct ata ctc aca ata gga     1152
Leu Val Lys Arg Cys Gly Tyr Leu Pro Leu Ala Ile Leu Thr Ile Gly
    370                 375                 380

ggc att ctt gct act aag aag ata atg gag tgg gga aaa ttt tac aga     1200
Gly Ile Leu Ala Thr Lys Lys Ile Met Glu Trp Gly Lys Phe Tyr Arg
385                 390                 395                 400

gaa ctt cct tca gag ctt gag agc aat cca agc cta gaa gcc atg agg     1248
Glu Leu Pro Ser Glu Leu Glu Ser Asn Pro Ser Leu Glu Ala Met Arg
                405                 410                 415

agg atg gtg acc cta agc tac aat cac tta cca tct cat ctt aaa cca     1296
Arg Met Val Thr Leu Ser Tyr Asn His Leu Pro Ser His Leu Lys Pro
            420                 425                 430

tgc ttt ctt tac cta agt att ttc cct gaa gat ttt gaa att caa aga     1344
Cys Phe Leu Tyr Leu Ser Ile Phe Pro Glu Asp Phe Glu Ile Gln Arg
        435                 440                 445
```

-continued

```
ggg cgc ctg gta gat aga tgg ata gca gag ggt ttt gtc aga gcc aca      1392
Gly Arg Leu Val Asp Arg Trp Ile Ala Glu Gly Phe Val Arg Ala Thr
    450                 455                 460

gat ggg gtg aac att gag gat gtt gga aat agt cac ttt aat gag ctt      1440
Asp Gly Val Asn Ile Glu Asp Val Gly Asn Ser His Phe Asn Glu Leu
465                 470                 475                 480

atc aac aga agt ctg att cag ccc tca aaa gtt agt aca gat gga gtt      1488
Ile Asn Arg Ser Leu Ile Gln Pro Ser Lys Val Ser Thr Asp Gly Val
                485                 490                 495

gtt aag aga tgt cga atc cat gat atc atg cgt gat atc ata gtt tca      1536
Val Lys Arg Cys Arg Ile His Asp Ile Met Arg Asp Ile Ile Val Ser
            500                 505                 510

att tct aga gag gaa aat ttt gtg ctg ttg act agg gag aag atc act      1584
Ile Ser Arg Glu Glu Asn Phe Val Leu Leu Thr Arg Glu Lys Ile Thr
        515                 520                 525

gtt gta gcg gag gag agc atc cgc cat cta gca ttt cat ggg agc aaa      1632
Val Val Ala Glu Glu Ser Ile Arg His Leu Ala Phe His Gly Ser Lys
    530                 535                 540

tgc tca aag ata tgc ttg gag tgg aac cat ctg cgc tca gta act ttg      1680
Cys Ser Lys Ile Cys Leu Glu Trp Asn His Leu Arg Ser Val Thr Leu
545                 550                 555                 560

ttt ggc gac aga cct gtg ggg cga aca cct gca ctt tgt tca cca caa      1728
Phe Gly Asp Arg Pro Val Gly Arg Thr Pro Ala Leu Cys Ser Pro Gln
                565                 570                 575

ttt agg atg ctg aga gtg ttg gat ctg gaa gat gca aaa ttc aaa ttc      1776
Phe Arg Met Leu Arg Val Leu Asp Leu Glu Asp Ala Lys Phe Lys Phe
            580                 585                 590

aca caa aat gat atc aga aat ata ggg ttg ttg cgc cac atg aaa tat      1824
Thr Gln Asn Asp Ile Arg Asn Ile Gly Leu Leu Arg His Met Lys Tyr
        595                 600                 605

ttg aat ttt gca aga gcc tca act att tat aca ctt cca agg tcc ata      1872
Leu Asn Phe Ala Arg Ala Ser Thr Ile Tyr Thr Leu Pro Arg Ser Ile
    610                 615                 620

gga aaa ttg cag tgc ttg caa att ttg aac atg agg gag gca aat atc      1920
Gly Lys Leu Gln Cys Leu Gln Ile Leu Asn Met Arg Glu Ala Asn Ile
625                 630                 635                 640

tca gca cta aca act gag gtg act aaa ctc cag aat ctc cgt agc ctc      1968
Ser Ala Leu Thr Thr Glu Val Thr Lys Leu Gln Asn Leu Arg Ser Leu
                645                 650                 655

cga tgc agc agg agg tct ggt tct ggt tac ttt agc ata ata gat aat      2016
Arg Cys Ser Arg Arg Ser Gly Ser Gly Tyr Phe Ser Ile Ile Asp Asn
            660                 665                 670

ccc aag gaa tgc ttg atg atc acc atg tgc tta ccg atg gtt ttc tta      2064
Pro Lys Glu Cys Leu Met Ile Thr Met Cys Leu Pro Met Val Phe Leu
        675                 680                 685

act tca ata aat ttc agt gac cgt gtg aag tta att cct gag ata tgc      2112
Thr Ser Ile Asn Phe Ser Asp Arg Val Lys Leu Ile Pro Glu Ile Cys
    690                 695                 700

atg tca tgt tct acc cgt tgg tct gat aca aag ggt gtg agg gtg cca      2160
Met Ser Cys Ser Thr Arg Trp Ser Asp Thr Lys Gly Val Arg Val Pro
705                 710                 715                 720

aga gga att gac aac cta aaa gag tta cag att cta gaa gtc gtg gac      2208
Arg Gly Ile Asp Asn Leu Lys Glu Leu Gln Ile Leu Glu Val Val Asp
                725                 730                 735

atc aac aga act agt agg aag gcg att gaa gag ctg ggg gag cta att      2256
Ile Asn Arg Thr Ser Arg Lys Ala Ile Glu Glu Leu Gly Glu Leu Ile
            740                 745                 750

cag tta aga aaa tta agc gtg aca aca aaa ggc gcc aca aat aag aag      2304
Gln Leu Arg Lys Leu Ser Val Thr Thr Lys Gly Ala Thr Asn Lys Lys
```

```
        755                 760                 765

tat cag ata ttt tgt gca gcg att gag aag ctc tct tct ctg caa tct     2352
Tyr Gln Ile Phe Cys Ala Ala Ile Glu Lys Leu Ser Ser Leu Gln Ser
    770                 775                 780

ctc cgt gtg gat gct gag gga ttc tca gat act gga aca ctt gag tgg     2400
Leu Arg Val Asp Ala Glu Gly Phe Ser Asp Thr Gly Thr Leu Glu Trp
785                 790                 795                 800

ctc aat tcg att gca tgt cct cct cca ttc ttg aag aga ctc aag ttg     2448
Leu Asn Ser Ile Ala Cys Pro Pro Pro Phe Leu Lys Arg Leu Lys Leu
                805                 810                 815

aat gga tct ctt gca gat aca cca aac tgg ttt ggg aac ctt aag cag     2496
Asn Gly Ser Leu Ala Asp Thr Pro Asn Trp Phe Gly Asn Leu Lys Gln
            820                 825                 830

ctg gtg aag atg tgc tta tcc aga tgt ggg cta aaa gat ggt aaa act     2544
Leu Val Lys Met Cys Leu Ser Arg Cys Gly Leu Lys Asp Gly Lys Thr
        835                 840                 845

atg gag ata ctt ggg gca ctg ccc aac ctt atg gtt ctt cgt ctt tat     2592
Met Glu Ile Leu Gly Ala Leu Pro Asn Leu Met Val Leu Arg Leu Tyr
    850                 855                 860

cgc aac gca tat gct gac gag aaa atg aca ttc aga agg gga act ttc     2640
Arg Asn Ala Tyr Ala Asp Glu Lys Met Thr Phe Arg Arg Gly Thr Phe
865                 870                 875                 880

cca aat ctc agg tgt ctt gat att tac ttg ctg aag caa ctt aga gag     2688
Pro Asn Leu Arg Cys Leu Asp Ile Tyr Leu Leu Lys Gln Leu Arg Glu
                885                 890                 895

ata aga ttt gag gag ggc acc tcg cca acg atg gaa agt ata gaa att     2736
Ile Arg Phe Glu Glu Gly Thr Ser Pro Thr Met Glu Ser Ile Glu Ile
            900                 905                 910

tat ggt tgc agg ttg gaa tca ggg att att ggt atc aag cac ctt cca     2784
Tyr Gly Cys Arg Leu Glu Ser Gly Ile Ile Gly Ile Lys His Leu Pro
        915                 920                 925

aga ctt aag att att tcg ctt gaa tat gat ggt aaa gtc gcg aag ctt     2832
Arg Leu Lys Ile Ile Ser Leu Glu Tyr Asp Gly Lys Val Ala Lys Leu
    930                 935                 940

gat gtg ctg caa gag gaa gtg aat aca cac ccc aat cat act gaa ttg     2880
Asp Val Leu Gln Glu Glu Val Asn Thr His Pro Asn His Thr Glu Leu
945                 950                 955                 960

caa atg gca gag gat cga agt cat cat gac cta gga ggc ctt gca tct     2928
Gln Met Ala Glu Asp Arg Ser His His Asp Leu Gly Gly Leu Ala Ser
                965                 970                 975

gat ggc gat gat gcc cat gac aat cca gcg ttg cgc tat caa aca tca     2976
Asp Gly Asp Asp Ala His Asp Asn Pro Ala Leu Arg Tyr Gln Thr Ser
            980                 985                 990

tgt tga                                                             2982
Cys


<210> SEQ ID NO 2
<211> LENGTH: 993
<212> TYPE: PRT
<213> ORGANISM: Oryza minuta

<400> SEQUENCE: 2

Met Ala Ala Glu Thr Val Val Ser Met Ala Met Ser Val Leu Gly Ser
1               5                   10                  15

Ala Val Gly Lys Ala Ala Ser Ala Ala Ala Asp Glu Ala Thr Leu Leu
            20                  25                  30

Leu Gly Ile Gln Lys Glu Ile Trp Tyr Ile Lys Asp Glu Leu Lys Thr
        35                  40                  45

Ile Gln Ala Phe Leu Arg Ala Ala Glu Val Thr Lys Lys Lys Asp Asp
```

-continued

```
    50                  55                  60

Leu Leu Lys Val Trp Ala Glu Gln Val Arg Asp Leu Ser Tyr Asn Ile
65                  70                  75                  80

Glu Asp Cys Leu Asp Glu Phe Lys Val His Val Glu Ser Gln Ser Leu
                85                  90                  95

Ala Lys Gln Leu Met Lys Leu Gly Glu Arg His Arg Ile Ala Val Gln
            100                 105                 110

Ile Arg Asn Leu Lys Ser Arg Ile Glu Glu Val Ser Asn Arg Asn Thr
        115                 120                 125

Arg Tyr Ser Leu Ile Lys Pro Ile Ser Ser Ile Thr Thr Glu Asp Glu
    130                 135                 140

Arg Asp Ser Tyr Leu Glu Asp Ala Arg Asn Arg Ser Gly Ser Asn Thr
145                 150                 155                 160

Asp Glu Ser Glu Leu Val Gly Phe Ala Lys Thr Lys Asp Glu Leu Leu
                165                 170                 175

Lys Leu Ile Asp Val Asn Thr Asn Asp Gly Pro Ala Lys Val Ile Cys
            180                 185                 190

Val Val Gly Met Gly Gly Leu Gly Lys Thr Thr Leu Ala Arg Lys Ala
        195                 200                 205

Tyr Glu Asn Lys Glu His Met Lys Asn Phe Ser Cys Cys Ala Trp Ile
    210                 215                 220

Thr Val Ser Gln Ser Phe Asp Arg Lys Glu Ile Leu Lys Gln Met Ile
225                 230                 235                 240

Arg Gln Leu Leu Gly Ala Asp Ser Leu Asp Lys Leu Leu Lys Glu Phe
                245                 250                 255

Ser Glu Lys Leu Leu Val Gln Val Gln His Leu Ala Asp His Leu Val
            260                 265                 270

Glu Gly Leu Lys Glu Lys Arg Tyr Phe Val Val Leu Asp Asp Leu Trp
        275                 280                 285

Thr Ile Asp Ala Trp Asn Trp Ile His Asp Ile Ala Phe Pro Lys Ile
    290                 295                 300

Asn Asn Arg Gly Ser Arg Ile Ile Ile Thr Thr Arg Asp Ala Gly Leu
305                 310                 315                 320

Ala Gly Arg Cys Thr Ser Glu Ser Leu Ile Tyr His Leu Glu Pro Leu
                325                 330                 335

His Ile Asp Asp Ala Ile His Leu Leu Leu Ala Lys Thr Asn Ile Arg
            340                 345                 350

Leu Glu Asp Met Glu Asn Asp Glu Asp Leu Gly Ser Ile Val Thr Lys
        355                 360                 365

Leu Val Lys Arg Cys Gly Tyr Leu Pro Leu Ala Ile Leu Thr Ile Gly
    370                 375                 380

Gly Ile Leu Ala Thr Lys Lys Ile Met Glu Trp Gly Lys Phe Tyr Arg
385                 390                 395                 400

Glu Leu Pro Ser Glu Leu Glu Ser Asn Pro Ser Leu Glu Ala Met Arg
                405                 410                 415

Arg Met Val Thr Leu Ser Tyr Asn His Leu Pro Ser His Leu Lys Pro
            420                 425                 430

Cys Phe Leu Tyr Leu Ser Ile Phe Pro Glu Asp Phe Glu Ile Gln Arg
        435                 440                 445

Gly Arg Leu Val Asp Arg Trp Ile Ala Glu Gly Phe Val Arg Ala Thr
    450                 455                 460

Asp Gly Val Asn Ile Glu Asp Val Gly Asn Ser His Phe Asn Glu Leu
465                 470                 475                 480
```

-continued

```
Ile Asn Arg Ser Leu Ile Gln Pro Ser Lys Val Ser Thr Asp Gly Val
                485                 490                 495

Val Lys Arg Cys Arg Ile His Asp Ile Met Arg Asp Ile Ile Val Ser
            500                 505                 510

Ile Ser Arg Glu Glu Asn Phe Val Leu Leu Thr Arg Glu Lys Ile Thr
        515                 520                 525

Val Val Ala Glu Glu Ser Ile Arg His Leu Ala Phe His Gly Ser Lys
    530                 535                 540

Cys Ser Lys Ile Cys Leu Glu Trp Asn His Leu Arg Ser Val Thr Leu
545                 550                 555                 560

Phe Gly Asp Arg Pro Val Gly Arg Thr Pro Ala Leu Cys Ser Pro Gln
                565                 570                 575

Phe Arg Met Leu Arg Val Leu Asp Leu Glu Asp Ala Lys Phe Lys Phe
            580                 585                 590

Thr Gln Asn Asp Ile Arg Asn Ile Gly Leu Leu Arg His Met Lys Tyr
        595                 600                 605

Leu Asn Phe Ala Arg Ala Ser Thr Ile Tyr Thr Leu Pro Arg Ser Ile
    610                 615                 620

Gly Lys Leu Gln Cys Leu Gln Ile Leu Asn Met Arg Glu Ala Asn Ile
625                 630                 635                 640

Ser Ala Leu Thr Thr Glu Val Thr Lys Leu Gln Asn Leu Arg Ser Leu
                645                 650                 655

Arg Cys Ser Arg Arg Ser Gly Ser Gly Tyr Phe Ser Ile Ile Asp Asn
            660                 665                 670

Pro Lys Glu Cys Leu Met Ile Thr Met Cys Leu Pro Met Val Phe Leu
        675                 680                 685

Thr Ser Ile Asn Phe Ser Asp Arg Val Lys Leu Ile Pro Glu Ile Cys
    690                 695                 700

Met Ser Cys Ser Thr Arg Trp Ser Asp Thr Lys Gly Val Arg Val Pro
705                 710                 715                 720

Arg Gly Ile Asp Asn Leu Lys Glu Leu Gln Ile Leu Glu Val Val Asp
                725                 730                 735

Ile Asn Arg Thr Ser Arg Lys Ala Ile Glu Glu Leu Gly Glu Leu Ile
            740                 745                 750

Gln Leu Arg Lys Leu Ser Val Thr Thr Lys Gly Ala Thr Asn Lys Lys
        755                 760                 765

Tyr Gln Ile Phe Cys Ala Ala Ile Glu Lys Leu Ser Ser Leu Gln Ser
    770                 775                 780

Leu Arg Val Asp Ala Glu Gly Phe Ser Asp Thr Gly Thr Leu Glu Trp
785                 790                 795                 800

Leu Asn Ser Ile Ala Cys Pro Pro Pro Phe Leu Lys Arg Leu Lys Leu
                805                 810                 815

Asn Gly Ser Leu Ala Asp Thr Pro Asn Trp Phe Gly Asn Leu Lys Gln
            820                 825                 830

Leu Val Lys Met Cys Leu Ser Arg Cys Gly Leu Lys Asp Gly Lys Thr
        835                 840                 845

Met Glu Ile Leu Gly Ala Leu Pro Asn Leu Met Val Leu Arg Leu Tyr
    850                 855                 860

Arg Asn Ala Tyr Ala Asp Glu Lys Met Thr Phe Arg Arg Gly Thr Phe
865                 870                 875                 880

Pro Asn Leu Arg Cys Leu Asp Ile Tyr Leu Leu Lys Gln Leu Arg Glu
                885                 890                 895
```

-continued

```
Ile Arg Phe Glu Glu Gly Thr Ser Pro Thr Met Glu Ser Ile Glu Ile
            900                 905                 910

Tyr Gly Cys Arg Leu Glu Ser Gly Ile Ile Gly Ile Lys His Leu Pro
        915                 920                 925

Arg Leu Lys Ile Ile Ser Leu Glu Tyr Asp Gly Lys Val Ala Lys Leu
    930                 935                 940

Asp Val Leu Gln Glu Glu Val Asn Thr His Pro Asn His Thr Glu Leu
945                 950                 955                 960

Gln Met Ala Glu Asp Arg Ser His His Asp Leu Gly Gly Leu Ala Ser
                965                 970                 975

Asp Gly Asp Asp Ala His Asp Asn Pro Ala Leu Arg Tyr Gln Thr Ser
            980                 985                 990

Cys


<210> SEQ ID NO 3
<211> LENGTH: 3099
<212> TYPE: DNA
<213> ORGANISM: Oryza minuta
<220> FEATURE:
<221> NAME/KEY: CDS
<222> LOCATION: (1)...(3099)

<400> SEQUENCE: 3

atg gcg gag acg gtg ctg agc atg gcg agg tcg ctg gtg ggc agt gcc      48
Met Ala Glu Thr Val Leu Ser Met Ala Arg Ser Leu Val Gly Ser Ala
1               5                   10                  15

atc agc aag gcc gcc tct gcc gct gcc aat gag acg agc ctc ctg ctc      96
Ile Ser Lys Ala Ala Ser Ala Ala Ala Asn Glu Thr Ser Leu Leu Leu
            20                  25                  30

ggc gtc gag aag gac atc tgg tat atc aaa gat gag cta aaa aca atg     144
Gly Val Glu Lys Asp Ile Trp Tyr Ile Lys Asp Glu Leu Lys Thr Met
        35                  40                  45

cag gca ttc ctt aga gct gct gaa gtt atg aaa aag aaa gat gaa cta     192
Gln Ala Phe Leu Arg Ala Ala Glu Val Met Lys Lys Lys Asp Glu Leu
    50                  55                  60

tta aag gtt tgg gca gag caa ata cgt gac ctg tcg tat gac att gaa     240
Leu Lys Val Trp Ala Glu Gln Ile Arg Asp Leu Ser Tyr Asp Ile Glu
65                  70                  75                  80

gat tcc ctt gat gaa ttt aaa gtc cat att gaa agc caa acc cta ttt     288
Asp Ser Leu Asp Glu Phe Lys Val His Ile Glu Ser Gln Thr Leu Phe
                85                  90                  95

cgt cag ttg gtg aaa ctt aga gag cgc cac cgg atc gct atc cgt atc     336
Arg Gln Leu Val Lys Leu Arg Glu Arg His Arg Ile Ala Ile Arg Ile
            100                 105                 110

cac aac ctc aaa tca aga gtt gaa gaa gtg agt agc agg aac aca cgc     384
His Asn Leu Lys Ser Arg Val Glu Glu Val Ser Ser Arg Asn Thr Arg
        115                 120                 125

tac aat tta gtc gag cct att tcc tcc ggc aca gag gat gac atg gat     432
Tyr Asn Leu Val Glu Pro Ile Ser Ser Gly Thr Glu Asp Asp Met Asp
    130                 135                 140

tcc tat gca gaa gac att cgc aat caa tca gct cga aat gtg gat gaa     480
Ser Tyr Ala Glu Asp Ile Arg Asn Gln Ser Ala Arg Asn Val Asp Glu
145                 150                 155                 160

gct gag ctt gtt ggg ttt tct gac tcc aag aaa agg ctg ctt gaa atg     528
Ala Glu Leu Val Gly Phe Ser Asp Ser Lys Lys Arg Leu Leu Glu Met
                165                 170                 175

atc gat acc aat gct aat gat ggt ccg gcc aag gta atc tgt gtt gtt     576
Ile Asp Thr Asn Ala Asn Asp Gly Pro Ala Lys Val Ile Cys Val Val
            180                 185                 190
```

-continued

```
ggg atg ggt ggt tta ggc aag aca gct ctt tcg agg aag atc ttt gaa      624
Gly Met Gly Gly Leu Gly Lys Thr Ala Leu Ser Arg Lys Ile Phe Glu
        195                 200                 205

agc gaa gaa gac att agg aag aac ttc cct tgc aat gct tgg att aca      672
Ser Glu Glu Asp Ile Arg Lys Asn Phe Pro Cys Asn Ala Trp Ile Thr
    210                 215                 220

gtg tca caa tca ttt cac agg att gag cta ctt aaa gat atg ata cgc      720
Val Ser Gln Ser Phe His Arg Ile Glu Leu Leu Lys Asp Met Ile Arg
225                 230                 235                 240

caa ctt ctt ggt ccc agt tct ctg gat caa ctc ttg cat gaa ttg caa      768
Gln Leu Leu Gly Pro Ser Ser Leu Asp Gln Leu Leu His Glu Leu Gln
                245                 250                 255

ggg aag gtg gtg gtg caa gta cat cat ctt tct gag tac ctg ata gaa      816
Gly Lys Val Val Val Gln Val His His Leu Ser Glu Tyr Leu Ile Glu
            260                 265                 270

gag ctc aag gag aag agg tac ttt gtt gtt cta gat gat cta tgg att      864
Glu Leu Lys Glu Lys Arg Tyr Phe Val Val Leu Asp Asp Leu Trp Ile
        275                 280                 285

tta cat gat tgg aat tgg ata aat gaa att gca ttt cct aag aac aat      912
Leu His Asp Trp Asn Trp Ile Asn Glu Ile Ala Phe Pro Lys Asn Asn
    290                 295                 300

aag aag ggc agt cga ata gta ata acc act cgg aat gtt gat cta gcg      960
Lys Lys Gly Ser Arg Ile Val Ile Thr Thr Arg Asn Val Asp Leu Ala
305                 310                 315                 320

gag aag tgt gcc aca gcc tca ctg gtg tac cac ctt gat ttc ttg cag     1008
Glu Lys Cys Ala Thr Ala Ser Leu Val Tyr His Leu Asp Phe Leu Gln
                325                 330                 335

atg aac gat gcc att tca ttg cta ctg aga aaa aca aat aaa aat cat     1056
Met Asn Asp Ala Ile Ser Leu Leu Leu Arg Lys Thr Asn Lys Asn His
            340                 345                 350

gaa gac atg gaa tca aat aaa aat atg caa aag atg gtt gaa cga att     1104
Glu Asp Met Glu Ser Asn Lys Asn Met Gln Lys Met Val Glu Arg Ile
        355                 360                 365

gta aat aaa tgt ggt cgt cta cca tta gca ata ctt aca ata gga gct     1152
Val Asn Lys Cys Gly Arg Leu Pro Leu Ala Ile Leu Thr Ile Gly Ala
    370                 375                 380

gtg ctt gca act aaa cag gtg tca gaa tgg gag aaa ttc tat gaa caa     1200
Val Leu Ala Thr Lys Gln Val Ser Glu Trp Glu Lys Phe Tyr Glu Gln
385                 390                 395                 400

ctt cct tca gaa cta gaa ata aac cca agc ctg gaa gct ttg agg aga     1248
Leu Pro Ser Glu Leu Glu Ile Asn Pro Ser Leu Glu Ala Leu Arg Arg
                405                 410                 415

atg gtg acc cta ggt tac aac cac cta cca tcc cat ctg aaa cca tgc     1296
Met Val Thr Leu Gly Tyr Asn His Leu Pro Ser His Leu Lys Pro Cys
            420                 425                 430

ttt ttg tat cta agt atc ttt cct gag gat ttt gaa ata caa agg aat     1344
Phe Leu Tyr Leu Ser Ile Phe Pro Glu Asp Phe Glu Ile Gln Arg Asn
        435                 440                 445

cgt cta gta ggt aga tgg ata gca gaa ggg ttt gtt aga cca aag gtt     1392
Arg Leu Val Gly Arg Trp Ile Ala Glu Gly Phe Val Arg Pro Lys Val
    450                 455                 460

ggg atg acg act aag gat gtc gga gaa agt tac ttt aat gag cta atc     1440
Gly Met Thr Thr Lys Asp Val Gly Glu Ser Tyr Phe Asn Glu Leu Ile
465                 470                 475                 480

aac cga agt atg att caa cga tca aga gtg ggc aca gca gga aaa att     1488
Asn Arg Ser Met Ile Gln Arg Ser Arg Val Gly Thr Ala Gly Lys Ile
                485                 490                 495

aag act tgt cga atc cat gat atc atc cgt gat atc aca gtt tca atc     1536
Lys Thr Cys Arg Ile His Asp Ile Ile Arg Asp Ile Thr Val Ser Ile
            500                 505                 510
```

-continued

```
tcg aga cag gaa aat ttt gta tta tta cca atg gga gat ggc tct gat      1584
Ser Arg Gln Glu Asn Phe Val Leu Leu Pro Met Gly Asp Gly Ser Asp
        515                 520                 525

tta gtt cag gaa aac act cgc cac ata gca ttc cat ggg agt atg tcc      1632
Leu Val Gln Glu Asn Thr Arg His Ile Ala Phe His Gly Ser Met Ser
    530                 535                 540

tgc aaa aca gga ttg gat tgg agc att att cga tca tta gct att ttt      1680
Cys Lys Thr Gly Leu Asp Trp Ser Ile Ile Arg Ser Leu Ala Ile Phe
545                 550                 555                 560

ggt gac aga ccc aag agt cta gca cat gca gtt tgt cca gat caa ttg      1728
Gly Asp Arg Pro Lys Ser Leu Ala His Ala Val Cys Pro Asp Gln Leu
                565                 570                 575

agg atg tta cgg gtc ttg gat ctt gaa gat gtg aca ttc tta atc act      1776
Arg Met Leu Arg Val Leu Asp Leu Glu Asp Val Thr Phe Leu Ile Thr
            580                 585                 590

caa aaa gat ttc gac cgt att gca ttg ttg tgc cac ttg aaa tac ttg      1824
Gln Lys Asp Phe Asp Arg Ile Ala Leu Leu Cys His Leu Lys Tyr Leu
        595                 600                 605

agt att gga tat tcg tca tcc ata tat tca ctt ccc aga tcc att ggt      1872
Ser Ile Gly Tyr Ser Ser Ser Ile Tyr Ser Leu Pro Arg Ser Ile Gly
    610                 615                 620

aaa cta cag ggc cta cag act ttg aac atg tca agc aca tac att gca      1920
Lys Leu Gln Gly Leu Gln Thr Leu Asn Met Ser Ser Thr Tyr Ile Ala
625                 630                 635                 640

gca cta cca agt gag atc agt aaa ctc caa tgt ctg cat act ctt cgt      1968
Ala Leu Pro Ser Glu Ile Ser Lys Leu Gln Cys Leu His Thr Leu Arg
                645                 650                 655

tgt ata aga gag ctt gaa ttt gac aac ttt agt cta aat cac cca atg      2016
Cys Ile Arg Glu Leu Glu Phe Asp Asn Phe Ser Leu Asn His Pro Met
            660                 665                 670

aag tgc ata act aac aca ata tgc ctg cct aaa gta ttc aca cct tta      2064
Lys Cys Ile Thr Asn Thr Ile Cys Leu Pro Lys Val Phe Thr Pro Leu
        675                 680                 685

gtt agt cgc gat aat cgt gca aaa caa att gct gaa ttt cac atg gcc      2112
Val Ser Arg Asp Asn Arg Ala Lys Gln Ile Ala Glu Phe His Met Ala
    690                 695                 700

acc aaa agt ttc tgg tct gaa tca ttc ggt gtg aag gta ccc aaa gga      2160
Thr Lys Ser Phe Trp Ser Glu Ser Phe Gly Val Lys Val Pro Lys Gly
705                 710                 715                 720

ata ggt aag ttg cga gac tta cag gtt cta gag tat gta gat atc agg      2208
Ile Gly Lys Leu Arg Asp Leu Gln Val Leu Glu Tyr Val Asp Ile Arg
                725                 730                 735

cgg acc agt agt aga gca atc aaa gag ctg ggg cag tta agc aag ttg      2256
Arg Thr Ser Ser Arg Ala Ile Lys Glu Leu Gly Gln Leu Ser Lys Leu
            740                 745                 750

agg aaa tta gct gtg ata aca aaa ggc tcg aca aag gaa aaa tgt aag      2304
Arg Lys Leu Ala Val Ile Thr Lys Gly Ser Thr Lys Glu Lys Cys Lys
        755                 760                 765

ata ctt tat gca gcc att gag aag ctc tct tcc ctc caa tct ctc tat      2352
Ile Leu Tyr Ala Ala Ile Glu Lys Leu Ser Ser Leu Gln Ser Leu Tyr
    770                 775                 780

atg aat gct gcg tta tta tca gat att gaa aca ctt gag tgc cta gat      2400
Met Asn Ala Ala Leu Leu Ser Asp Ile Glu Thr Leu Glu Cys Leu Asp
785                 790                 795                 800

tct att tca tct cct cct ccc cta ctg agg aca ctc ggg ttg aat gga      2448
Ser Ile Ser Ser Pro Pro Pro Leu Leu Arg Thr Leu Gly Leu Asn Gly
                805                 810                 815

agt ctt gaa gag atg cct aac tgg att gag cag ctc act cac ctg aag      2496
Ser Leu Glu Glu Met Pro Asn Trp Ile Glu Gln Leu Thr His Leu Lys
```

```
            820                 825                 830

aag ttc aac tta tgg agt agt aaa cta aag gaa ggt aaa aac atg ctg     2544
Lys Phe Asn Leu Trp Ser Ser Lys Leu Lys Glu Gly Lys Asn Met Leu
        835                 840                 845

ata ctt ggg gca ctg ccc aac ctc atg ttc ctt tct ctt tat cat aat     2592
Ile Leu Gly Ala Leu Pro Asn Leu Met Phe Leu Ser Leu Tyr His Asn
    850                 855                 860

tct tat ctt ggg gag aag cta gta ttc aaa acg gga gca ttc cca aat     2640
Ser Tyr Leu Gly Glu Lys Leu Val Phe Lys Thr Gly Ala Phe Pro Asn
865                 870                 875                 880

ctt aga aca ctt gtg att ttc aat ttg gat cag cta aga gag atc aga     2688
Leu Arg Thr Leu Val Ile Phe Asn Leu Asp Gln Leu Arg Glu Ile Arg
                885                 890                 895

ttt gag gac ggc agc tca ccc cag ttg gaa aag ata gaa atc tct tgc     2736
Phe Glu Asp Gly Ser Ser Pro Gln Leu Glu Lys Ile Glu Ile Ser Cys
            900                 905                 910

tgc agg ttg gaa tca ggg att att ggt atc att cac ctt cca agg ctc     2784
Cys Arg Leu Glu Ser Gly Ile Ile Gly Ile Ile His Leu Pro Arg Leu
        915                 920                 925

aag gag att tca ctt gaa tac aaa agt aaa gtg gct agg ctt ggt cag     2832
Lys Glu Ile Ser Leu Glu Tyr Lys Ser Lys Val Ala Arg Leu Gly Gln
    930                 935                 940

ctg aag gga gaa gtg aac aca cac cca aat cgc ccc gtg ctg cga atg     2880
Leu Lys Gly Glu Val Asn Thr His Pro Asn Arg Pro Val Leu Arg Met
945                 950                 955                 960

gac agt gac cga agg gat cac gac ctg ggg gct gaa gcc gaa gga tct     2928
Asp Ser Asp Arg Arg Asp His Asp Leu Gly Ala Glu Ala Glu Gly Ser
                965                 970                 975

tct ata gaa gtg caa aca gca gat cct gtt cct gat gcc caa gga tca     2976
Ser Ile Glu Val Gln Thr Ala Asp Pro Val Pro Asp Ala Gln Gly Ser
            980                 985                 990

gtc act gta gca gtg gaa gca acg gat ccc ctt ccc gag cag gag gga     3024
Val Thr Val Ala Val Glu Ala Thr Asp Pro Leu Pro Glu Gln Glu Gly
        995                 1000                1005

gag agc tcg cag tcg cag gtg atc acg ttg acg acg aat gat agc gaa     3072
Glu Ser Ser Gln Ser Gln Val Ile Thr Leu Thr Thr Asn Asp Ser Glu
    1010                1015                1020

gag ata ggc aca gct caa gct ggc tga                                 3099
Glu Ile Gly Thr Ala Gln Ala Gly
1025                1030


<210> SEQ ID NO 4
<211> LENGTH: 1032
<212> TYPE: PRT
<213> ORGANISM: Oryza minuta

<400> SEQUENCE: 4

Met Ala Glu Thr Val Leu Ser Met Ala Arg Ser Leu Val Gly Ser Ala
1               5                   10                  15

Ile Ser Lys Ala Ala Ser Ala Ala Ala Asn Glu Thr Ser Leu Leu Leu
            20                  25                  30

Gly Val Glu Lys Asp Ile Trp Tyr Ile Lys Asp Glu Leu Lys Thr Met
        35                  40                  45

Gln Ala Phe Leu Arg Ala Ala Glu Val Met Lys Lys Lys Asp Glu Leu
    50                  55                  60

Leu Lys Val Trp Ala Glu Gln Ile Arg Asp Leu Ser Tyr Asp Ile Glu
65                  70                  75                  80

Asp Ser Leu Asp Glu Phe Lys Val His Ile Glu Ser Gln Thr Leu Phe
                85                  90                  95
```

-continued

```
Arg Gln Leu Val Lys Leu Arg Glu Arg His Arg Ile Ala Ile Arg Ile
            100                 105                 110

His Asn Leu Lys Ser Arg Val Glu Glu Val Ser Ser Arg Asn Thr Arg
        115                 120                 125

Tyr Asn Leu Val Glu Pro Ile Ser Ser Gly Thr Glu Asp Asp Met Asp
    130                 135                 140

Ser Tyr Ala Glu Asp Ile Arg Asn Gln Ser Ala Arg Asn Val Asp Glu
145                 150                 155                 160

Ala Glu Leu Val Gly Phe Ser Asp Ser Lys Lys Arg Leu Leu Glu Met
                165                 170                 175

Ile Asp Thr Asn Ala Asn Asp Gly Pro Ala Lys Val Ile Cys Val Val
            180                 185                 190

Gly Met Gly Gly Leu Gly Lys Thr Ala Leu Ser Arg Lys Ile Phe Glu
        195                 200                 205

Ser Glu Glu Asp Ile Arg Lys Asn Phe Pro Cys Asn Ala Trp Ile Thr
    210                 215                 220

Val Ser Gln Ser Phe His Arg Ile Glu Leu Leu Lys Asp Met Ile Arg
225                 230                 235                 240

Gln Leu Leu Gly Pro Ser Ser Leu Asp Gln Leu Leu His Glu Leu Gln
                245                 250                 255

Gly Lys Val Val Val Gln Val His His Leu Ser Glu Tyr Leu Ile Glu
            260                 265                 270

Glu Leu Lys Glu Lys Arg Tyr Phe Val Val Leu Asp Asp Leu Trp Ile
        275                 280                 285

Leu His Asp Trp Asn Trp Ile Asn Glu Ile Ala Phe Pro Lys Asn Asn
    290                 295                 300

Lys Lys Gly Ser Arg Ile Val Ile Thr Thr Arg Asn Val Asp Leu Ala
305                 310                 315                 320

Glu Lys Cys Ala Thr Ala Ser Leu Val Tyr His Leu Asp Phe Leu Gln
                325                 330                 335

Met Asn Asp Ala Ile Ser Leu Leu Leu Arg Lys Thr Asn Lys Asn His
            340                 345                 350

Glu Asp Met Glu Ser Asn Lys Asn Met Gln Lys Met Val Glu Arg Ile
        355                 360                 365

Val Asn Lys Cys Gly Arg Leu Pro Leu Ala Ile Leu Thr Ile Gly Ala
    370                 375                 380

Val Leu Ala Thr Lys Gln Val Ser Glu Trp Glu Lys Phe Tyr Glu Gln
385                 390                 395                 400

Leu Pro Ser Glu Leu Glu Ile Asn Pro Ser Leu Glu Ala Leu Arg Arg
                405                 410                 415

Met Val Thr Leu Gly Tyr Asn His Leu Pro Ser His Leu Lys Pro Cys
            420                 425                 430

Phe Leu Tyr Leu Ser Ile Phe Pro Glu Asp Phe Glu Ile Gln Arg Asn
        435                 440                 445

Arg Leu Val Gly Arg Trp Ile Ala Glu Gly Phe Val Arg Pro Lys Val
    450                 455                 460

Gly Met Thr Thr Lys Asp Val Gly Glu Ser Tyr Phe Asn Glu Leu Ile
465                 470                 475                 480

Asn Arg Ser Met Ile Gln Arg Ser Arg Val Gly Thr Ala Gly Lys Ile
                485                 490                 495

Lys Thr Cys Arg Ile His Asp Ile Ile Arg Asp Ile Thr Val Ser Ile
            500                 505                 510
```

-continued

```
Ser Arg Gln Glu Asn Phe Val Leu Leu Pro Met Gly Asp Gly Ser Asp
        515                 520                 525

Leu Val Gln Glu Asn Thr Arg His Ile Ala Phe His Gly Ser Met Ser
    530                 535                 540

Cys Lys Thr Gly Leu Asp Trp Ser Ile Ile Arg Ser Leu Ala Ile Phe
545                 550                 555                 560

Gly Asp Arg Pro Lys Ser Leu Ala His Ala Val Cys Pro Asp Gln Leu
                565                 570                 575

Arg Met Leu Arg Val Leu Asp Leu Glu Asp Val Thr Phe Leu Ile Thr
            580                 585                 590

Gln Lys Asp Phe Asp Arg Ile Ala Leu Leu Cys His Leu Lys Tyr Leu
        595                 600                 605

Ser Ile Gly Tyr Ser Ser Ser Ile Tyr Ser Leu Pro Arg Ser Ile Gly
    610                 615                 620

Lys Leu Gln Gly Leu Gln Thr Leu Asn Met Ser Ser Thr Tyr Ile Ala
625                 630                 635                 640

Ala Leu Pro Ser Glu Ile Ser Lys Leu Gln Cys Leu His Thr Leu Arg
                645                 650                 655

Cys Ile Arg Glu Leu Glu Phe Asp Asn Phe Ser Leu Asn His Pro Met
            660                 665                 670

Lys Cys Ile Thr Asn Thr Ile Cys Leu Pro Lys Val Phe Thr Pro Leu
        675                 680                 685

Val Ser Arg Asp Asn Arg Ala Lys Gln Ile Ala Glu Phe His Met Ala
    690                 695                 700

Thr Lys Ser Phe Trp Ser Glu Ser Phe Gly Val Lys Val Pro Lys Gly
705                 710                 715                 720

Ile Gly Lys Leu Arg Asp Leu Gln Val Leu Glu Tyr Val Asp Ile Arg
                725                 730                 735

Arg Thr Ser Ser Arg Ala Ile Lys Glu Leu Gly Gln Leu Ser Lys Leu
            740                 745                 750

Arg Lys Leu Ala Val Ile Thr Lys Gly Ser Thr Lys Glu Lys Cys Lys
        755                 760                 765

Ile Leu Tyr Ala Ala Ile Glu Lys Leu Ser Ser Leu Gln Ser Leu Tyr
    770                 775                 780

Met Asn Ala Ala Leu Leu Ser Asp Ile Glu Thr Leu Glu Cys Leu Asp
785                 790                 795                 800

Ser Ile Ser Ser Pro Pro Pro Leu Leu Arg Thr Leu Gly Leu Asn Gly
                805                 810                 815

Ser Leu Glu Glu Met Pro Asn Trp Ile Glu Gln Leu Thr His Leu Lys
            820                 825                 830

Lys Phe Asn Leu Trp Ser Ser Lys Leu Lys Glu Gly Lys Asn Met Leu
        835                 840                 845

Ile Leu Gly Ala Leu Pro Asn Leu Met Phe Leu Ser Leu Tyr His Asn
    850                 855                 860

Ser Tyr Leu Gly Glu Lys Leu Val Phe Lys Thr Gly Ala Phe Pro Asn
865                 870                 875                 880

Leu Arg Thr Leu Val Ile Phe Asn Leu Asp Gln Leu Arg Glu Ile Arg
                885                 890                 895

Phe Glu Asp Gly Ser Ser Pro Gln Leu Glu Lys Ile Glu Ile Ser Cys
            900                 905                 910

Cys Arg Leu Glu Ser Gly Ile Ile Gly Ile Ile His Leu Pro Arg Leu
        915                 920                 925

Lys Glu Ile Ser Leu Glu Tyr Lys Ser Lys Val Ala Arg Leu Gly Gln
```

-continued

```
    930                 935                 940

Leu Lys Gly Glu Val Asn Thr His Pro Asn Arg Pro Val Leu Arg Met
945                 950                 955                 960

Asp Ser Asp Arg Arg Asp His Asp Leu Gly Ala Glu Ala Glu Gly Ser
                965                 970                 975

Ser Ile Glu Val Gln Thr Ala Asp Pro Val Pro Asp Ala Gln Gly Ser
            980                 985                 990

Val Thr Val Ala Val Glu Ala Thr Asp Pro Leu Pro Glu Gln Glu Gly
        995                 1000                1005

Glu Ser Ser Gln Ser Gln Val Ile Thr Leu Thr Thr Asn Asp Ser Glu
    1010                1015                1020

Glu Ile Gly Thr Ala Gln Ala Gly
1025                1030


<210> SEQ ID NO 5
<211> LENGTH: 4147
<212> TYPE: DNA
<213> ORGANISM: Oryza minuta
<220> FEATURE:
<221> NAME/KEY: CDS
<222> LOCATION: (1)...(1983)

<400> SEQUENCE: 5

atg gcg gat aca gta ctc agc att gca aag tcc ctg gtg gga agt gct       48
Met Ala Asp Thr Val Leu Ser Ile Ala Lys Ser Leu Val Gly Ser Ala
1               5                   10                  15

gta agc aag gtt gct tcg gtt gcc gca gac aag atg atc atg ctg ctg       96
Val Ser Lys Val Ala Ser Val Ala Ala Asp Lys Met Ile Met Leu Leu
            20                  25                  30

gga gtg cag aag gag ata tgg ttc atc aaa gat gag cta caa acg ata      144
Gly Val Gln Lys Glu Ile Trp Phe Ile Lys Asp Glu Leu Gln Thr Ile
        35                  40                  45

caa gca ttt ttg att gct gcc gaa gca tca aag aaa agc ata cta ttg      192
Gln Ala Phe Leu Ile Ala Ala Glu Ala Ser Lys Lys Ser Ile Leu Leu
    50                  55                  60

aag gtt tgg gtg cag caa gta agg gat ctt tcc tat gac atc gaa gat      240
Lys Val Trp Val Gln Gln Val Arg Asp Leu Ser Tyr Asp Ile Glu Asp
65                  70                  75                  80

tgc ctt gat gaa ttt aca gtt cat gtg ggc agc caa aac ttg tcg agg      288
Cys Leu Asp Glu Phe Thr Val His Val Gly Ser Gln Asn Leu Ser Arg
                85                  90                  95

cag ttg atg aag cta aag gat cgc cat cgg att gcc atc cag atc cgc      336
Gln Leu Met Lys Leu Lys Asp Arg His Arg Ile Ala Ile Gln Ile Arg
            100                 105                 110

aat ctc agg aca aga att gaa gaa gta agc act agg aac ata cgc tac      384
Asn Leu Arg Thr Arg Ile Glu Glu Val Ser Thr Arg Asn Ile Arg Tyr
        115                 120                 125

aac tta ata gag aat gac ctc acc tgc acc act gat gag agg aat tta      432
Asn Leu Ile Glu Asn Asp Leu Thr Cys Thr Thr Asp Glu Arg Asn Leu
    130                 135                 140

ttt atg gaa gac att cgc aat caa tca gct aac aac atc gag gaa gct      480
Phe Met Glu Asp Ile Arg Asn Gln Ser Ala Asn Asn Ile Glu Glu Ala
145                 150                 155                 160

gat ctt gtg ggt ttt tct gga ccc aaa aga gag ttg ctt gat ctt ata      528
Asp Leu Val Gly Phe Ser Gly Pro Lys Arg Glu Leu Leu Asp Leu Ile
                165                 170                 175

gat gtc cat gcc aag gac gga cct aca aag gtt gta tgt gtt gtc ggt      576
Asp Val His Ala Lys Asp Gly Pro Thr Lys Val Val Cys Val Val Gly
            180                 185                 190
```

-continued

```
atg ggt ggt ttg ggt aag act act att gca agg aaa att tat gaa agc      624
Met Gly Gly Leu Gly Lys Thr Thr Ile Ala Arg Lys Ile Tyr Glu Ser
        195                 200                 205

aaa gag gac att gca aag aat ttt tct tgc tgt gct tgg att act gtt      672
Lys Glu Asp Ile Ala Lys Asn Phe Ser Cys Cys Ala Trp Ile Thr Val
    210                 215                 220

tca cag tcc ttt gtt agg gtg gaa cta ctc aag gat ttg atg gtg aaa      720
Ser Gln Ser Phe Val Arg Val Glu Leu Leu Lys Asp Leu Met Val Lys
225                 230                 235                 240

ctt ttt gga gag gaa gta ctg aag aag cgg ccg aga gaa ctc gaa ggg      768
Leu Phe Gly Glu Glu Val Leu Lys Lys Arg Pro Arg Glu Leu Glu Gly
                245                 250                 255

aag gtt cca caa gta gat gac ctt gcc agc tac ctc agg aca gag tta      816
Lys Val Pro Gln Val Asp Asp Leu Ala Ser Tyr Leu Arg Thr Glu Leu
            260                 265                 270

cat gaa agg agg tac ttt gtt gtg ctt gat gac gtg tgg agt aca gat      864
His Glu Arg Arg Tyr Phe Val Val Leu Asp Asp Val Trp Ser Thr Asp
        275                 280                 285

tca tgg aaa tgg att aat agt att gcc ttc cct aga aat aac aaa aaa      912
Ser Trp Lys Trp Ile Asn Ser Ile Ala Phe Pro Arg Asn Asn Lys Lys
    290                 295                 300

ggg agc cgg gtg ata gta aca aca aga gat gtt ggc tta gct aag aag      960
Gly Ser Arg Val Ile Val Thr Thr Arg Asp Val Gly Leu Ala Lys Lys
305                 310                 315                 320

tgt act tct gaa ttg ctt atc tac cag ctt aaa ccc cta gaa ata aac     1008
Cys Thr Ser Glu Leu Leu Ile Tyr Gln Leu Lys Pro Leu Glu Ile Asn
                325                 330                 335

tat gca aaa gag ttg ctt cta cgg aaa gca aat gaa gca ata gga gat     1056
Tyr Ala Lys Glu Leu Leu Leu Arg Lys Ala Asn Glu Ala Ile Gly Asp
            340                 345                 350

atg gaa agt gat aaa aag atg agt gac att ata act aaa ata gta aag     1104
Met Glu Ser Asp Lys Lys Met Ser Asp Ile Ile Thr Lys Ile Val Lys
        355                 360                 365

aag tgt ggg tat tta ccg ctg gct ata ctc aca ata gga ggc gtg ctt     1152
Lys Cys Gly Tyr Leu Pro Leu Ala Ile Leu Thr Ile Gly Gly Val Leu
    370                 375                 380

tcc acc aaa gag ata aga gag tgg gaa act ttt tat agt cag ata cct     1200
Ser Thr Lys Glu Ile Arg Glu Trp Glu Thr Phe Tyr Ser Gln Ile Pro
385                 390                 395                 400

tca gag ctt gag agc aac cca aac ctt gaa gca atg aga agg ata gtg     1248
Ser Glu Leu Glu Ser Asn Pro Asn Leu Glu Ala Met Arg Arg Ile Val
                405                 410                 415

acc cta agt tac aac tac tta ccg tct cat ctt aag caa tgc ttt ttg     1296
Thr Leu Ser Tyr Asn Tyr Leu Pro Ser His Leu Lys Gln Cys Phe Leu
            420                 425                 430

tat cta agc ata ttt cct gag gat ttt gaa att aat agg aac cgt ctg     1344
Tyr Leu Ser Ile Phe Pro Glu Asp Phe Glu Ile Asn Arg Asn Arg Leu
        435                 440                 445

gta aat aga tgg att gca gag ggg ttt att aaa gct agg act aat atg     1392
Val Asn Arg Trp Ile Ala Glu Gly Phe Ile Lys Ala Arg Thr Asn Met
    450                 455                 460

act att gaa gat gtt ggg aaa agt tac ttt aaa gaa ctt atc aac cgt     1440
Thr Ile Glu Asp Val Gly Lys Ser Tyr Phe Lys Glu Leu Ile Asn Arg
465                 470                 475                 480

agc atg att cag tca tca aga gcg ggt ata cga gga gat ttt aag agc     1488
Ser Met Ile Gln Ser Ser Arg Ala Gly Ile Arg Gly Asp Phe Lys Ser
                485                 490                 495

tgt cga gtc cat gac atc atg cgt gat att aca att tcg att tct aga     1536
Cys Arg Val His Asp Ile Met Arg Asp Ile Thr Ile Ser Ile Ser Arg
            500                 505                 510
```

-continued

```
gaa gaa aat ttc aca ctc tta ccc gat ggc act gac tat gat gta gta     1584
Glu Glu Asn Phe Thr Leu Leu Pro Asp Gly Thr Asp Tyr Asp Val Val
        515                 520                 525

cat ggg aac act cgg cac ata gca ttt cac ggg agt agg tat tgc tct     1632
His Gly Asn Thr Arg His Ile Ala Phe His Gly Ser Arg Tyr Cys Ser
    530                 535                 540

gaa aca agc ttg gac tgg agc att ata cgg tca tta act atg ttt ggt     1680
Glu Thr Ser Leu Asp Trp Ser Ile Ile Arg Ser Leu Thr Met Phe Gly
545                 550                 555                 560

gag agg tcc gta gaa cta gag cat tca gtt tgt tca tct cag ttg agg     1728
Glu Arg Ser Val Glu Leu Glu His Ser Val Cys Ser Ser Gln Leu Arg
                565                 570                 575

atg tta cgg gtc ttg gat cta ata gat gca caa ttt tct atc aca caa     1776
Met Leu Arg Val Leu Asp Leu Ile Asp Ala Gln Phe Ser Ile Thr Gln
            580                 585                 590

aat gat gtc gac aac ata gtg ctc ttg tgc cac ttg aaa tac cta cgc     1824
Asn Asp Val Asp Asn Ile Val Leu Leu Cys His Leu Lys Tyr Leu Arg
        595                 600                 605

att gca aga tac aga tac cgt tca cca tat att tat tca ctt cca caa     1872
Ile Ala Arg Tyr Arg Tyr Arg Ser Pro Tyr Ile Tyr Ser Leu Pro Gln
    610                 615                 620

tcc ata gct aga ctg cat ggt ctg cag aca ttg gac ttg ggt cag acg     1920
Ser Ile Ala Arg Leu His Gly Leu Gln Thr Leu Asp Leu Gly Gln Thr
625                 630                 635                 640

tac att tca aca ctg cca act cag att act aac ttc gga gtc tcc gta     1968
Tyr Ile Ser Thr Leu Pro Thr Gln Ile Thr Asn Phe Gly Val Ser Val
                645                 650                 655

gcc ttc gat gca tga aagaatattt ttcttcttct ttaagaacat atttaactaa     2023
Ala Phe Asp Ala
            660

cacattatgc ctgcccatga tattcacacc tttcgttagt acctcggatc gttctgaaac   2083

aattgctaaa ttgcacatgg ccaccaaagg cttccgttca aaatcaaatg gtgtcaaggt   2143

accaaaagga atatgtaagt tgagagactt acaagaggat tgctacggtc cagcaggttg   2203

taccgggcgg tactggtacc gcgcggtacc aaaacccatc taaccgttga atccgggatg   2263

ggtaggatcg ggagagaaaa gatgagcaag ggtggatgag ggagtacctg tttcgagtcg   2323

tcgttcccgg cggcggcggc gtggagtacc tgtttcgagt cgtcgtcgtt cccggtggcg   2383

gcgcagagca acaagggacg ccggcggcgc gggagaggat aaagtccggc ggcagcgcga   2443

gagagaaaaa agggaacggc gacggtgcgg gagaggaaca agggaaggac ggcggcggcg   2503

gaagaggaac aagtccgacg gcgaggaaga ggaacacggc ggcggcgaaa atcatccagc   2563

gtagctaggg ttcgagccgc ccgatccaaa cccatctatt gcacgcgaag ttactctttt   2623

acccttccaa ctctcttctc catgcggtat cacctaaggg acatttttgg taccgtgcgg   2683

taccacgcaa catcagccgt tggatcaggc cagatccaac ggccagcatt tggtaccgct   2743

cggtacgttg gacagtaaaa aaactcgact tacaaatatt ggaggtagtg gatattagaa   2803

ggactagcag tagagcaatc aaagagttgg ggcagttaag caagctgagg aaattatgtg   2863

tggtaacaaa gggatccaca aaggaaaaat gtgagatact ctatacagct atccagaagc   2923

tctgtttcct acaatctctc catgtgaatg ctgtgggatt ttcaggtatt ggaacacttc   2983

agtgtataga ttctatttca tctcctcctc ccctactgag gacactcagg ttgaatggaa   3043

gtcttgagga gatgcctaac tggattgagc agctcacgca cctgatgaag ttcaacttat   3103

ggaggagcaa actaaaagaa ggtaaaacca tgttggtact tgcggcgttg cccaacctca   3163
```

-continued

```
tggtccttta tcttcattcc aatgcttacc atggggagaa gctagtattc aaaatgggag   3223
cattcccaaa tcttagaaca ttttcgattt acaatttgga gcagctaaga gagattagat   3283
ttgaggacgg cagctcaatc ttgttggaaa agatagaaat attcaggggt tggaatcagg   3343
gattgttggt atcattcacc ttccaaggct caaggagatt tcacttggat acggaagtaa   3403
agtggctagg cttggtcagc tggagggaga agtgcgcaca cacccaaatc accccgtgat   3463
gcgaatgagg gaggaccgaa gtgatcacga ccttgcttgt gacgccgaag gatcccctgt   3523
tgaagtggaa gcaacagatc ctgtgagagc tcgcagttgc aggtgatcac gttgacaacg   3583
aacgacaggt cagtcactcc ctacacggca tcttaatgaa cttgttttat cctcttgtga   3643
gatcgatgat tttaactcac cctttcatct ctctcgtttt cttaacctaa cagcgaagag   3703
ataagcacaa cttaagctgg tttgatcaag tgatgatctc ctcctccatt ggcatctccg   3763
gtcgtccctg cttctgcggc tgcgcacctc gctgctctga ggaggggtgc tgatctaagg   3823
aggcttccac tttcttcaat tgcgtctcat gctctcgatt cttccctctc gggtatgaat   3883
tgttcaatct gatattttct cgcgatctgc tactggttcc agcatgagca tttgaaccag   3943
cagcttagaa ttatcgtttg atcaggtgtt atttatccct tcttacctgg gaactctact   4003
tatccatttc attcagaaca gaaaccatgt ttattacact atagagggga acaacagatc   4063
aggcacgagt tgtggttttg ttatttcctt tttggtgtgc acaccaggtg attgctagaa   4123
tgtctgaaag agcttgtgtg catg                                          4147
```

```
<210> SEQ ID NO 6
<211> LENGTH: 660
<212> TYPE: PRT
<213> ORGANISM: Oryza minuta

<400> SEQUENCE: 6

Met Ala Asp Thr Val Leu Ser Ile Ala Lys Ser Leu Val Gly Ser Ala
1               5                   10                  15

Val Ser Lys Val Ala Ser Val Ala Ala Asp Lys Met Ile Met Leu Leu
            20                  25                  30

Gly Val Gln Lys Glu Ile Trp Phe Ile Lys Asp Glu Leu Gln Thr Ile
        35                  40                  45

Gln Ala Phe Leu Ile Ala Ala Glu Ala Ser Lys Lys Ser Ile Leu Leu
    50                  55                  60

Lys Val Trp Val Gln Gln Val Arg Asp Leu Ser Tyr Asp Ile Glu Asp
65                  70                  75                  80

Cys Leu Asp Glu Phe Thr Val His Val Gly Ser Gln Asn Leu Ser Arg
                85                  90                  95

Gln Leu Met Lys Leu Lys Asp Arg His Arg Ile Ala Ile Gln Ile Arg
            100                 105                 110

Asn Leu Arg Thr Arg Ile Glu Glu Val Ser Thr Arg Asn Ile Arg Tyr
        115                 120                 125

Asn Leu Ile Glu Asn Asp Leu Thr Cys Thr Thr Asp Glu Arg Asn Leu
    130                 135                 140

Phe Met Glu Asp Ile Arg Asn Gln Ser Ala Asn Asn Ile Glu Glu Ala
145                 150                 155                 160

Asp Leu Val Gly Phe Ser Gly Pro Lys Arg Glu Leu Leu Asp Leu Ile
                165                 170                 175

Asp Val His Ala Lys Asp Gly Pro Thr Lys Val Val Cys Val Val Gly
            180                 185                 190

Met Gly Gly Leu Gly Lys Thr Thr Ile Ala Arg Lys Ile Tyr Glu Ser
```

-continued

```
        195                 200                 205

Lys Glu Asp Ile Ala Lys Asn Phe Ser Cys Cys Ala Trp Ile Thr Val
    210                 215                 220

Ser Gln Ser Phe Val Arg Val Glu Leu Leu Lys Asp Leu Met Val Lys
225                 230                 235                 240

Leu Phe Gly Glu Glu Val Leu Lys Lys Arg Pro Arg Glu Leu Glu Gly
                245                 250                 255

Lys Val Pro Gln Val Asp Asp Leu Ala Ser Tyr Leu Arg Thr Glu Leu
            260                 265                 270

His Glu Arg Arg Tyr Phe Val Val Leu Asp Asp Val Trp Ser Thr Asp
        275                 280                 285

Ser Trp Lys Trp Ile Asn Ser Ile Ala Phe Pro Arg Asn Asn Lys Lys
    290                 295                 300

Gly Ser Arg Val Ile Val Thr Thr Arg Asp Val Gly Leu Ala Lys Lys
305                 310                 315                 320

Cys Thr Ser Glu Leu Leu Ile Tyr Gln Leu Lys Pro Leu Glu Ile Asn
                325                 330                 335

Tyr Ala Lys Glu Leu Leu Leu Arg Lys Ala Asn Glu Ala Ile Gly Asp
            340                 345                 350

Met Glu Ser Asp Lys Lys Met Ser Asp Ile Ile Thr Lys Ile Val Lys
        355                 360                 365

Lys Cys Gly Tyr Leu Pro Leu Ala Ile Leu Thr Ile Gly Gly Val Leu
    370                 375                 380

Ser Thr Lys Glu Ile Arg Glu Trp Glu Thr Phe Tyr Ser Gln Ile Pro
385                 390                 395                 400

Ser Glu Leu Glu Ser Asn Pro Asn Leu Glu Ala Met Arg Arg Ile Val
                405                 410                 415

Thr Leu Ser Tyr Asn Tyr Leu Pro Ser His Leu Lys Gln Cys Phe Leu
            420                 425                 430

Tyr Leu Ser Ile Phe Pro Glu Asp Phe Glu Ile Asn Arg Asn Arg Leu
        435                 440                 445

Val Asn Arg Trp Ile Ala Glu Gly Phe Ile Lys Ala Arg Thr Asn Met
    450                 455                 460

Thr Ile Glu Asp Val Gly Lys Ser Tyr Phe Lys Glu Leu Ile Asn Arg
465                 470                 475                 480

Ser Met Ile Gln Ser Ser Arg Ala Gly Ile Arg Gly Asp Phe Lys Ser
                485                 490                 495

Cys Arg Val His Asp Ile Met Arg Asp Ile Thr Ile Ser Ile Ser Arg
            500                 505                 510

Glu Glu Asn Phe Thr Leu Leu Pro Asp Gly Thr Asp Tyr Asp Val Val
        515                 520                 525

His Gly Asn Thr Arg His Ile Ala Phe His Gly Ser Arg Tyr Cys Ser
    530                 535                 540

Glu Thr Ser Leu Asp Trp Ser Ile Ile Arg Ser Leu Thr Met Phe Gly
545                 550                 555                 560

Glu Arg Ser Val Glu Leu Glu His Ser Val Cys Ser Ser Gln Leu Arg
                565                 570                 575

Met Leu Arg Val Leu Asp Leu Ile Asp Ala Gln Phe Ser Ile Thr Gln
            580                 585                 590

Asn Asp Val Asp Asn Ile Val Leu Leu Cys His Leu Lys Tyr Leu Arg
        595                 600                 605

Ile Ala Arg Tyr Arg Tyr Arg Ser Pro Tyr Ile Tyr Ser Leu Pro Gln
    610                 615                 620
```

```
Ser Ile Ala Arg Leu His Gly Leu Gln Thr Leu Asp Leu Gly Gln Thr
625                 630                 635                 640

Tyr Ile Ser Thr Leu Pro Thr Gln Ile Thr Asn Phe Gly Val Ser Val
                645                 650                 655

Ala Phe Asp Ala
            660


<210> SEQ ID NO 7
<211> LENGTH: 3099
<212> TYPE: DNA
<213> ORGANISM: Oryza minuta
<220> FEATURE:
<221> NAME/KEY: CDS
<222> LOCATION: (1)...(3099)

<400> SEQUENCE: 7

atg gcg gag acg gtg ctg agc atg gcg agg tcg ctg gtg ggc agc gcc       48
Met Ala Glu Thr Val Leu Ser Met Ala Arg Ser Leu Val Gly Ser Ala
1               5                   10                  15

atc agc aag gcc gcc tcc gct gct gcc gac gag acc agc ctc ctg ctg       96
Ile Ser Lys Ala Ala Ser Ala Ala Ala Asp Glu Thr Ser Leu Leu Leu
            20                  25                  30

ggc gtc gag aaa gac atc tgg tat atc aaa gat gag cta aaa acg atg      144
Gly Val Glu Lys Asp Ile Trp Tyr Ile Lys Asp Glu Leu Lys Thr Met
        35                  40                  45

caa gca ttc ctt aga gct gct gaa ctt atg aaa aag aaa gat gaa cta      192
Gln Ala Phe Leu Arg Ala Ala Glu Leu Met Lys Lys Lys Asp Glu Leu
    50                  55                  60

tta aag gtt tgg gca gag caa ata cgt gac ctg tca tat gac att gaa      240
Leu Lys Val Trp Ala Glu Gln Ile Arg Asp Leu Ser Tyr Asp Ile Glu
65                  70                  75                  80

gat tcc ctt gat gaa ttt aag gtc cat att gaa agc caa acc cta ttt      288
Asp Ser Leu Asp Glu Phe Lys Val His Ile Glu Ser Gln Thr Leu Phe
                85                  90                  95

cgt cag ttg gtg aaa ctc aga gaa cgc cac cga att gct atc cgt atc      336
Arg Gln Leu Val Lys Leu Arg Glu Arg His Arg Ile Ala Ile Arg Ile
            100                 105                 110

cac aac ctt aaa tca aga gtt gaa gaa gtg agt agc agg aac aca cgc      384
His Asn Leu Lys Ser Arg Val Glu Glu Val Ser Ser Arg Asn Thr Arg
        115                 120                 125

tac agt tta gtc aag cct att tcc tct ggc aca gag att gac atg gat      432
Tyr Ser Leu Val Lys Pro Ile Ser Ser Gly Thr Glu Ile Asp Met Asp
    130                 135                 140

tcc tat gca gaa gac att cgt aat cag tca gct cgc aat gtg gat gag      480
Ser Tyr Ala Glu Asp Ile Arg Asn Gln Ser Ala Arg Asn Val Asp Glu
145                 150                 155                 160

gct gag ctt gtt ggg ttt tct gac tcc aag aaa agg ctg ctt gaa atg      528
Ala Glu Leu Val Gly Phe Ser Asp Ser Lys Lys Arg Leu Leu Glu Met
                165                 170                 175

atc gat acc aat gct aat gat ggt ccg gcc aag gta atc tgt gtt gtt      576
Ile Asp Thr Asn Ala Asn Asp Gly Pro Ala Lys Val Ile Cys Val Val
            180                 185                 190

ggg atg ggt ggt tta ggc aag aca gct ctt tcg agg aag atc ttt gaa      624
Gly Met Gly Gly Leu Gly Lys Thr Ala Leu Ser Arg Lys Ile Phe Glu
        195                 200                 205

agc gaa gaa gac att agg aag aac ttc cct tgc aat gct tgg att aca      672
Ser Glu Glu Asp Ile Arg Lys Asn Phe Pro Cys Asn Ala Trp Ile Thr
    210                 215                 220

gtg tca caa tca ttt cac agg att gag cta ctt aaa gat atg ata cgc      720
Val Ser Gln Ser Phe His Arg Ile Glu Leu Leu Lys Asp Met Ile Arg
```

-continued

```
225                 230                 235                 240

caa ctt ctt ggc ccc agt tct ctg gat caa ctc ttg caa gaa ttg caa      768
Gln Leu Leu Gly Pro Ser Ser Leu Asp Gln Leu Leu Gln Glu Leu Gln
                245                 250                 255

ggg aag gtg gtg gtg caa gta cat cat ctt tct gag tac ctg ata gaa      816
Gly Lys Val Val Val Gln Val His His Leu Ser Glu Tyr Leu Ile Glu
            260                 265                 270

gag ctc aag gag aag agg tac ttt gtt gtt cta gat gat cta tgg att      864
Glu Leu Lys Glu Lys Arg Tyr Phe Val Val Leu Asp Asp Leu Trp Ile
        275                 280                 285

tta cat gat tgg aat tgg ata aat gaa att gca ttt cct aag aac aat      912
Leu His Asp Trp Asn Trp Ile Asn Glu Ile Ala Phe Pro Lys Asn Asn
    290                 295                 300

aag aag ggc agt cga ata gta ata acc act cgg aat gtt gat ctt gcg      960
Lys Lys Gly Ser Arg Ile Val Ile Thr Thr Arg Asn Val Asp Leu Ala
305                 310                 315                 320

gag aag tgt gcc aca gcc tca ctg gtg tac cac ctt gat ttc ttg cag     1008
Glu Lys Cys Ala Thr Ala Ser Leu Val Tyr His Leu Asp Phe Leu Gln
                325                 330                 335

atg aac gat gcc ata aca ttg cta ctg aga aaa aca aat aaa aat cat     1056
Met Asn Asp Ala Ile Thr Leu Leu Leu Arg Lys Thr Asn Lys Asn His
            340                 345                 350

gaa gac atg gaa tca aat aaa aat atg caa aag atg gtt gaa cga att     1104
Glu Asp Met Glu Ser Asn Lys Asn Met Gln Lys Met Val Glu Arg Ile
        355                 360                 365

gta aat aaa tgt ggt cgt cta cca tta gca ata ctt aca ata gga gct     1152
Val Asn Lys Cys Gly Arg Leu Pro Leu Ala Ile Leu Thr Ile Gly Ala
    370                 375                 380

gtg ctt gca act aaa cag gtg tca gaa tgg gag aaa ttc tat gaa cac     1200
Val Leu Ala Thr Lys Gln Val Ser Glu Trp Glu Lys Phe Tyr Glu His
385                 390                 395                 400

ctt cct tca gaa cta gaa ata aac cca agc ctg gaa gct ttg agg aga     1248
Leu Pro Ser Glu Leu Glu Ile Asn Pro Ser Leu Glu Ala Leu Arg Arg
                405                 410                 415

atg gtg acc cta ggt tac aac cac cta cca tcc cat ttg aaa cca tgc     1296
Met Val Thr Leu Gly Tyr Asn His Leu Pro Ser His Leu Lys Pro Cys
            420                 425                 430

ttt ttg tat cta agt atc ttt cct gag gat ttt gaa atc aaa agg aat     1344
Phe Leu Tyr Leu Ser Ile Phe Pro Glu Asp Phe Glu Ile Lys Arg Asn
        435                 440                 445

cgt cta gta ggt aga tgg ata gca gaa ggg ttt gtt aga cca aag gtt     1392
Arg Leu Val Gly Arg Trp Ile Ala Glu Gly Phe Val Arg Pro Lys Val
    450                 455                 460

ggg atg acg act aag gat gtc gga gaa agt tac ttt aat gag cta atc     1440
Gly Met Thr Thr Lys Asp Val Gly Glu Ser Tyr Phe Asn Glu Leu Ile
465                 470                 475                 480

aac cga agt atg att caa cga tca aga gtg ggc ata gca gga aaa att     1488
Asn Arg Ser Met Ile Gln Arg Ser Arg Val Gly Ile Ala Gly Lys Ile
                485                 490                 495

aag act tgt cga att cat gat atc atc cgt gat atc aca gtt tca atc     1536
Lys Thr Cys Arg Ile His Asp Ile Ile Arg Asp Ile Thr Val Ser Ile
            500                 505                 510

tcg aga cag gaa aat ttt gta tta tta cca atg gga gat ggc tct gat     1584
Ser Arg Gln Glu Asn Phe Val Leu Leu Pro Met Gly Asp Gly Ser Asp
        515                 520                 525

tta gtt cag gaa aac act cgc cac ata gca ttc cat ggg agt atg tcc     1632
Leu Val Gln Glu Asn Thr Arg His Ile Ala Phe His Gly Ser Met Ser
    530                 535                 540

tgc aaa act gga ttg gat tgg agc att att cga tca tta gct att ttt     1680
```

-continued

```
Cys Lys Thr Gly Leu Asp Trp Ser Ile Ile Arg Ser Leu Ala Ile Phe
545                 550                 555                 560

ggt gac aga ccc aag agt cta gca cat gca gtt tgt cca gat caa ttg      1728
Gly Asp Arg Pro Lys Ser Leu Ala His Ala Val Cys Pro Asp Gln Leu
                565                 570                 575

agg atg tta cgg gtc ttg gat ctt gaa gat gtg aca ttc tta atc act      1776
Arg Met Leu Arg Val Leu Asp Leu Glu Asp Val Thr Phe Leu Ile Thr
            580                 585                 590

caa aaa gat ttc gac cgt att gca ttg ttg tgc cac ttg aaa tac ttg      1824
Gln Lys Asp Phe Asp Arg Ile Ala Leu Leu Cys His Leu Lys Tyr Leu
        595                 600                 605

agt att gga tat tcg tca tcc ata tat tca ctt ccc aga tcc att ggt      1872
Ser Ile Gly Tyr Ser Ser Ser Ile Tyr Ser Leu Pro Arg Ser Ile Gly
    610                 615                 620

aaa cta cag ggc cta caa act ttg aac atg ccg agc aca tac att gca      1920
Lys Leu Gln Gly Leu Gln Thr Leu Asn Met Pro Ser Thr Tyr Ile Ala
625                 630                 635                 640

gca cta cca agt gag atc agt aaa ctc caa tgt ctg cat act ctt cgt      1968
Ala Leu Pro Ser Glu Ile Ser Lys Leu Gln Cys Leu His Thr Leu Arg
                645                 650                 655

tgt ata gga cag ttt cat tat gac aac ttt agt cta aac cac cca atg      2016
Cys Ile Gly Gln Phe His Tyr Asp Asn Phe Ser Leu Asn His Pro Met
            660                 665                 670

aag tgc ata act aac aca ata tgc ctg cct aaa gta ttc aca cct tta      2064
Lys Cys Ile Thr Asn Thr Ile Cys Leu Pro Lys Val Phe Thr Pro Leu
        675                 680                 685

gtt agt cgc gat gat cgt gca aaa caa att gct gaa ttg cac atg gcc      2112
Val Ser Arg Asp Asp Arg Ala Lys Gln Ile Ala Glu Leu His Met Ala
    690                 695                 700

acc aaa agt tgc tgg tct gaa tca atc ggt gtg aag gta ccc aaa gga      2160
Thr Lys Ser Cys Trp Ser Glu Ser Ile Gly Val Lys Val Pro Lys Gly
705                 710                 715                 720

ata ggt aag ttg cga gac ttg cag gtt cta gag tat gta gat atc agg      2208
Ile Gly Lys Leu Arg Asp Leu Gln Val Leu Glu Tyr Val Asp Ile Arg
                725                 730                 735

cgg acc agt agt aga gca atc aaa gag ctg ggg cag tta agc aag ctg      2256
Arg Thr Ser Ser Arg Ala Ile Lys Glu Leu Gly Gln Leu Ser Lys Leu
            740                 745                 750

agg aaa tta ggt gtg aca aca aac ggg tcg aca aag gaa aaa tgt aag      2304
Arg Lys Leu Gly Val Thr Thr Asn Gly Ser Thr Lys Glu Lys Cys Lys
        755                 760                 765

ata ctt tat gca gcc att gag aag ctc tct tcc ctc caa tct ctc cat      2352
Ile Leu Tyr Ala Ala Ile Glu Lys Leu Ser Ser Leu Gln Ser Leu His
    770                 775                 780

gtg gat gct gca gga atc tca gat ggt gga aca ctt gag tgc cta gat      2400
Val Asp Ala Ala Gly Ile Ser Asp Gly Gly Thr Leu Glu Cys Leu Asp
785                 790                 795                 800

tct att tca tct cct cct ccc cta ctg agg aca ctc gtg ttg gat gga      2448
Ser Ile Ser Ser Pro Pro Pro Leu Leu Arg Thr Leu Val Leu Asp Gly
                805                 810                 815

att ctt gag gag atg cct aac tgg att gag cag ctc act cac ctg aag      2496
Ile Leu Glu Glu Met Pro Asn Trp Ile Glu Gln Leu Thr His Leu Lys
            820                 825                 830

aag atc tac tta ttg agg agc aaa cta aag gaa ggt aaa acc atg ctg      2544
Lys Ile Tyr Leu Leu Arg Ser Lys Leu Lys Glu Gly Lys Thr Met Leu
        835                 840                 845

ata ctt ggg gca ctg ccc aac ctc atg gtc ctt cat ctt tat cgg aat      2592
Ile Leu Gly Ala Leu Pro Asn Leu Met Val Leu His Leu Tyr Arg Asn
    850                 855                 860
```

-continued

```
gct tac ctt ggg gag aag cta gta ttc aaa aca gga gca ttc cca aat      2640
Ala Tyr Leu Gly Glu Lys Leu Val Phe Lys Thr Gly Ala Phe Pro Asn
865                 870                 875                 880

ctt aga aca ctt tgg att tat gaa ttg gat cag cta aga gag atc aga      2688
Leu Arg Thr Leu Trp Ile Tyr Glu Leu Asp Gln Leu Arg Glu Ile Arg
                885                 890                 895

ttt gag gac ggc agc tca ccc ctg ttg gaa aag ata gaa ata ggc gag      2736
Phe Glu Asp Gly Ser Ser Pro Leu Leu Glu Lys Ile Glu Ile Gly Glu
            900                 905                 910

tgc agg ttg gaa tct ggg att act ggt atc att cac ctt cca aag ctc      2784
Cys Arg Leu Glu Ser Gly Ile Thr Gly Ile Ile His Leu Pro Lys Leu
        915                 920                 925

aag gag att cca att aga tac gga agt aaa gtg gct ggg ctt ggt cag      2832
Lys Glu Ile Pro Ile Arg Tyr Gly Ser Lys Val Ala Gly Leu Gly Gln
    930                 935                 940

ctg gag gga gaa gtg aac gca cac cca aat cgc ccc gtg ctg cta atg      2880
Leu Glu Gly Glu Val Asn Ala His Pro Asn Arg Pro Val Leu Leu Met
945                 950                 955                 960

tac agt gac cga agg tat cac gac ctg ggg gct gaa gcc gaa gga tct      2928
Tyr Ser Asp Arg Arg Tyr His Asp Leu Gly Ala Glu Ala Glu Gly Ser
                965                 970                 975

tct ata gaa gtg caa aca gca gat cct gtt cct gat gcc gaa gga tca      2976
Ser Ile Glu Val Gln Thr Ala Asp Pro Val Pro Asp Ala Glu Gly Ser
            980                 985                 990

gtc act gta gca gtg gaa gca acg gat ccc ctt ccc gag cag gag gga      3024
Val Thr Val Ala Val Glu Ala Thr Asp Pro Leu Pro Glu Gln Glu Gly
        995                 1000                1005

gag agc tcg cag tcg cag gtg atc acg ttg acg acg aat gat agc gaa      3072
Glu Ser Ser Gln Ser Gln Val Ile Thr Leu Thr Thr Asn Asp Ser Glu
    1010                1015                1020

gag ata ggc aca gct caa gct ggc tga                                  3099
Glu Ile Gly Thr Ala Gln Ala Gly
1025                1030


<210> SEQ ID NO 8
<211> LENGTH: 1032
<212> TYPE: PRT
<213> ORGANISM: Oryza minuta

<400> SEQUENCE: 8

Met Ala Glu Thr Val Leu Ser Met Ala Arg Ser Leu Val Gly Ser Ala
1               5                   10                  15

Ile Ser Lys Ala Ala Ser Ala Ala Ala Asp Glu Thr Ser Leu Leu Leu
            20                  25                  30

Gly Val Glu Lys Asp Ile Trp Tyr Ile Lys Asp Glu Leu Lys Thr Met
        35                  40                  45

Gln Ala Phe Leu Arg Ala Ala Glu Leu Met Lys Lys Lys Asp Glu Leu
    50                  55                  60

Leu Lys Val Trp Ala Glu Gln Ile Arg Asp Leu Ser Tyr Asp Ile Glu
65                  70                  75                  80

Asp Ser Leu Asp Glu Phe Lys Val His Ile Glu Ser Gln Thr Leu Phe
                85                  90                  95

Arg Gln Leu Val Lys Leu Arg Glu Arg His Arg Ile Ala Ile Arg Ile
            100                 105                 110

His Asn Leu Lys Ser Arg Val Glu Glu Val Ser Ser Arg Asn Thr Arg
        115                 120                 125

Tyr Ser Leu Val Lys Pro Ile Ser Ser Gly Thr Glu Ile Asp Met Asp
    130                 135                 140
```

-continued

```
Ser Tyr Ala Glu Asp Ile Arg Asn Gln Ser Ala Arg Asn Val Asp Glu
145                 150                 155                 160

Ala Glu Leu Val Gly Phe Ser Asp Ser Lys Lys Arg Leu Leu Glu Met
                165                 170                 175

Ile Asp Thr Asn Ala Asn Asp Gly Pro Ala Lys Val Ile Cys Val Val
            180                 185                 190

Gly Met Gly Gly Leu Gly Lys Thr Ala Leu Ser Arg Lys Ile Phe Glu
        195                 200                 205

Ser Glu Glu Asp Ile Arg Lys Asn Phe Pro Cys Asn Ala Trp Ile Thr
    210                 215                 220

Val Ser Gln Ser Phe His Arg Ile Glu Leu Leu Lys Asp Met Ile Arg
225                 230                 235                 240

Gln Leu Leu Gly Pro Ser Ser Leu Asp Gln Leu Leu Gln Glu Leu Gln
                245                 250                 255

Gly Lys Val Val Val Gln Val His His Leu Ser Glu Tyr Leu Ile Glu
            260                 265                 270

Glu Leu Lys Glu Lys Arg Tyr Phe Val Val Leu Asp Asp Leu Trp Ile
        275                 280                 285

Leu His Asp Trp Asn Trp Ile Asn Glu Ile Ala Phe Pro Lys Asn Asn
    290                 295                 300

Lys Lys Gly Ser Arg Ile Val Ile Thr Thr Arg Asn Val Asp Leu Ala
305                 310                 315                 320

Glu Lys Cys Ala Thr Ala Ser Leu Val Tyr His Leu Asp Phe Leu Gln
                325                 330                 335

Met Asn Asp Ala Ile Thr Leu Leu Leu Arg Lys Thr Asn Lys Asn His
            340                 345                 350

Glu Asp Met Glu Ser Asn Lys Asn Met Gln Lys Met Val Glu Arg Ile
        355                 360                 365

Val Asn Lys Cys Gly Arg Leu Pro Leu Ala Ile Leu Thr Ile Gly Ala
    370                 375                 380

Val Leu Ala Thr Lys Gln Val Ser Glu Trp Glu Lys Phe Tyr Glu His
385                 390                 395                 400

Leu Pro Ser Glu Leu Glu Ile Asn Pro Ser Leu Glu Ala Leu Arg Arg
                405                 410                 415

Met Val Thr Leu Gly Tyr Asn His Leu Pro Ser His Leu Lys Pro Cys
            420                 425                 430

Phe Leu Tyr Leu Ser Ile Phe Pro Glu Asp Phe Glu Ile Lys Arg Asn
        435                 440                 445

Arg Leu Val Gly Arg Trp Ile Ala Glu Gly Phe Val Arg Pro Lys Val
    450                 455                 460

Gly Met Thr Thr Lys Asp Val Gly Glu Ser Tyr Phe Asn Glu Leu Ile
465                 470                 475                 480

Asn Arg Ser Met Ile Gln Arg Ser Arg Val Gly Ile Ala Gly Lys Ile
                485                 490                 495

Lys Thr Cys Arg Ile His Asp Ile Ile Arg Asp Ile Thr Val Ser Ile
            500                 505                 510

Ser Arg Gln Glu Asn Phe Val Leu Leu Pro Met Gly Asp Gly Ser Asp
        515                 520                 525

Leu Val Gln Glu Asn Thr Arg His Ile Ala Phe His Gly Ser Met Ser
    530                 535                 540

Cys Lys Thr Gly Leu Asp Trp Ser Ile Ile Arg Ser Leu Ala Ile Phe
545                 550                 555                 560

Gly Asp Arg Pro Lys Ser Leu Ala His Ala Val Cys Pro Asp Gln Leu
```

-continued

```
                565                 570                 575

Arg Met Leu Arg Val Leu Asp Leu Glu Asp Val Thr Phe Leu Ile Thr
            580                 585                 590

Gln Lys Asp Phe Asp Arg Ile Ala Leu Leu Cys His Leu Lys Tyr Leu
        595                 600                 605

Ser Ile Gly Tyr Ser Ser Ser Ile Tyr Ser Leu Pro Arg Ser Ile Gly
    610                 615                 620

Lys Leu Gln Gly Leu Gln Thr Leu Asn Met Pro Ser Thr Tyr Ile Ala
625                 630                 635                 640

Ala Leu Pro Ser Glu Ile Ser Lys Leu Gln Cys Leu His Thr Leu Arg
                645                 650                 655

Cys Ile Gly Gln Phe His Tyr Asp Asn Phe Ser Leu Asn His Pro Met
            660                 665                 670

Lys Cys Ile Thr Asn Thr Ile Cys Leu Pro Lys Val Phe Thr Pro Leu
        675                 680                 685

Val Ser Arg Asp Asp Arg Ala Lys Gln Ile Ala Glu Leu His Met Ala
    690                 695                 700

Thr Lys Ser Cys Trp Ser Glu Ser Ile Gly Val Lys Val Pro Lys Gly
705                 710                 715                 720

Ile Gly Lys Leu Arg Asp Leu Gln Val Leu Glu Tyr Val Asp Ile Arg
                725                 730                 735

Arg Thr Ser Ser Arg Ala Ile Lys Glu Leu Gly Gln Leu Ser Lys Leu
            740                 745                 750

Arg Lys Leu Gly Val Thr Thr Asn Gly Ser Thr Lys Glu Lys Cys Lys
        755                 760                 765

Ile Leu Tyr Ala Ala Ile Glu Lys Leu Ser Ser Leu Gln Ser Leu His
    770                 775                 780

Val Asp Ala Ala Gly Ile Ser Asp Gly Gly Thr Leu Glu Cys Leu Asp
785                 790                 795                 800

Ser Ile Ser Ser Pro Pro Pro Leu Leu Arg Thr Leu Val Leu Asp Gly
                805                 810                 815

Ile Leu Glu Glu Met Pro Asn Trp Ile Glu Gln Leu Thr His Leu Lys
            820                 825                 830

Lys Ile Tyr Leu Leu Arg Ser Lys Leu Lys Glu Gly Lys Thr Met Leu
        835                 840                 845

Ile Leu Gly Ala Leu Pro Asn Leu Met Val Leu His Leu Tyr Arg Asn
    850                 855                 860

Ala Tyr Leu Gly Glu Lys Leu Val Phe Lys Thr Gly Ala Phe Pro Asn
865                 870                 875                 880

Leu Arg Thr Leu Trp Ile Tyr Glu Leu Asp Gln Leu Arg Glu Ile Arg
                885                 890                 895

Phe Glu Asp Gly Ser Ser Pro Leu Leu Glu Lys Ile Glu Ile Gly Glu
            900                 905                 910

Cys Arg Leu Glu Ser Gly Ile Thr Gly Ile Ile His Leu Pro Lys Leu
        915                 920                 925

Lys Glu Ile Pro Ile Arg Tyr Gly Ser Lys Val Ala Gly Leu Gly Gln
    930                 935                 940

Leu Glu Gly Glu Val Asn Ala His Pro Asn Arg Pro Val Leu Leu Met
945                 950                 955                 960

Tyr Ser Asp Arg Arg Tyr His Asp Leu Gly Ala Glu Ala Glu Gly Ser
                965                 970                 975

Ser Ile Glu Val Gln Thr Ala Asp Pro Val Pro Asp Ala Glu Gly Ser
            980                 985                 990
```

```
Val Thr Val Ala Val Glu Ala Thr Asp Pro Leu Pro Glu Gln Glu Gly
        995                 1000                1005

Glu Ser Ser Gln Ser Gln Val Ile Thr Leu Thr Thr Asn Asp Ser Glu
    1010                1015                1020

Glu Ile Gly Thr Ala Gln Ala Gly
1025                1030


<210> SEQ ID NO 9
<211> LENGTH: 1389
<212> TYPE: DNA
<213> ORGANISM: Oryza minuta
<220> FEATURE:
<221> NAME/KEY: CDS
<222> LOCATION: (322)...(471)

<400> SEQUENCE: 9

ggaaaagata gaactctctt ggtgaaggtt ggaatcaggg attattggta tcattcacct     60

tccaaagctc aaggaaattt cacttgaata cagaagtaaa gtagctaggc ttggtcagct    120

ggagggagaa gtgggcgcac atccaaagca tccagtgctg caaatgatgg aggatcgaag    180

ctatcgcgac ctaggaggtg atgccgaagt atctgctgta caagtgcaag caggatcccc    240

tccctgagca agagggagag agcacgcagg aaaaatattc gccatgtagc gtaccatgac    300

agcaagtgtt ctattatagg c atg gac tgg agc cat gta cgg tcg tta act      351
                        Met Asp Trp Ser His Val Arg Ser Leu Thr
                        1               5                   10

ttg ttt ggc gat gag aga ccc aaa gag ctc tca cct cca ttc tgt tct      399
Leu Phe Gly Asp Glu Arg Pro Lys Glu Leu Ser Pro Pro Phe Cys Ser
                15                  20                  25

ccc caa ttg aaa atg cta agg gtg ctg gat cta cta gat att ata ttt      447
Pro Gln Leu Lys Met Leu Arg Val Leu Asp Leu Leu Asp Ile Ile Phe
            30                  35                  40

gga cta gca aaa aga tat gga taa aatatggttg ttgcgtcact tgaaatatgt     501
Gly Leu Ala Lys Arg Tyr Gly
        45

caatattagg tgttccaatg aatgctcaag catttatgca cttcctagtt ccataagaaa    561

attacaagag ttacacactg gacatatctg acacttatat tacaatgcta ccaaatgaga    621

ttagtaaatt gcagtctatg tgtcctccgt ggtagaagac aaggatccta ctatgacctt    681

gatacatata atcgtaagga atgtgtactt attttatcac gtattccttt gattatggct    741

ttaagtgatt ctgataacca tagaagacta attaccgatc tacacacggg ttgttcaagt    801

cattggcata taattaaaga tggtgcaagg gtaccaagtg gaatcaagaa tttgaagaga    861

ttgaaagtac tagagatagt ggatatcgcg gtaactgaca gcagagcaat tcaagagttg    921

ggggaactta accagctaag aaaactaagt gtcatgacaa aagggtcgaa caagaaaaag    981

tgcaaaatac tttgtgcagc catcgaaaag ctcacttcct tcaaatctct ctatgtggat   1041

ggtcatggat actcacttga tggaacactt gagtggcttg attctatttc ccatcctcct   1101

tccctcaaga gccttagatt gaaggggtgt attaaggaga cacccaactg gtttagggag   1161

ctcaaacact tggtgaagat ttacttatat aaaagtcgcc taaatggaga taccatggag   1221

atactcgggg aactacataa tctcatggat cttcactttc gttggtatgc atacgttggg   1281

gagaagctag tgttcattga gggagcattc caaaatctcc ggaagcttgt tgttgaaact   1341

gaggataaac taagagaggt gaggtttgag gagggcacct caccccag                1389


<210> SEQ ID NO 10
```

<211> LENGTH: 49
<212> TYPE: PRT
<213> ORGANISM: Oryza minuta

<400> SEQUENCE: 10

```
Met Asp Trp Ser His Val Arg Ser Leu Thr Leu Phe Gly Asp Glu Arg
1               5                   10                  15

Pro Lys Glu Leu Ser Pro Pro Phe Cys Ser Pro Gln Leu Lys Met Leu
            20                  25                  30

Arg Val Leu Asp Leu Leu Asp Ile Ile Phe Gly Leu Ala Lys Arg Tyr
        35                  40                  45

Gly
```

<210> SEQ ID NO 11
<211> LENGTH: 2997
<212> TYPE: DNA
<213> ORGANISM: Oryza minuta
<220> FEATURE:
<221> NAME/KEY: CDS
<222> LOCATION: (1)...(2997)

<400> SEQUENCE: 11

```
atg gcg gag acg gtg ctg agc atg gcg agg tcg ctg gtg ggg agc gcc       48
Met Ala Glu Thr Val Leu Ser Met Ala Arg Ser Leu Val Gly Ser Ala
1               5                   10                  15

atc agc aag gcc gcc tcc gcc gct gcc gac gag acc agc ctc ctg ctc       96
Ile Ser Lys Ala Ala Ser Ala Ala Ala Asp Glu Thr Ser Leu Leu Leu
            20                  25                  30

ggc gtc gag aaa gac atc tgg tac ttg ttt aga cat ggt gtt gga cgg      144
Gly Val Glu Lys Asp Ile Trp Tyr Leu Phe Arg His Gly Val Gly Arg
        35                  40                  45

tcg aat ggt ggg cct gtt gta ggt atg gtg gca tct ggc aac cag tca      192
Ser Asn Gly Gly Pro Val Val Gly Met Val Ala Ser Gly Asn Gln Ser
    50                  55                  60

tgc tta gca ata gat tcc tat gca gaa gac att cgc aat caa tca gct      240
Cys Leu Ala Ile Asp Ser Tyr Ala Glu Asp Ile Arg Asn Gln Ser Ala
65                  70                  75                  80

cga aat gtg gat gaa gct gag ctt gtt ggg ttt tct gac tcc aag aaa      288
Arg Asn Val Asp Glu Ala Glu Leu Val Gly Phe Ser Asp Ser Lys Lys
                85                  90                  95

agg ctg ctt gaa atg atc gat acc aat gct aat gat ggt ccg gcc aag      336
Arg Leu Leu Glu Met Ile Asp Thr Asn Ala Asn Asp Gly Pro Ala Lys
            100                 105                 110

gta atc tgt gtt gtt ggg atg ggt ggt tta ggc aag aca gct ctt tcg      384
Val Ile Cys Val Val Gly Met Gly Gly Leu Gly Lys Thr Ala Leu Ser
        115                 120                 125

agg aag atc ttt gaa agc gaa gaa gac att agg aag aac ttc cct tgc      432
Arg Lys Ile Phe Glu Ser Glu Glu Asp Ile Arg Lys Asn Phe Pro Cys
    130                 135                 140

aat gct tgg att aca gtg tca caa tca ttt cac agg att gag cta ctt      480
Asn Ala Trp Ile Thr Val Ser Gln Ser Phe His Arg Ile Glu Leu Leu
145                 150                 155                 160

aaa gat atg ata cgc caa ctt ctt ggc ccc agt tct ctg gat caa ctc      528
Lys Asp Met Ile Arg Gln Leu Leu Gly Pro Ser Ser Leu Asp Gln Leu
                165                 170                 175

ttg caa gaa ttg caa ggg aag gtg gtg gtg caa gta cat cat ctt tct      576
Leu Gln Glu Leu Gln Gly Lys Val Val Val Gln Val His His Leu Ser
            180                 185                 190

gag tac ctg ata gaa gag ctc aag gag aag agg tac ttt gtt gtt cta      624
Glu Tyr Leu Ile Glu Glu Leu Lys Glu Lys Arg Tyr Phe Val Val Leu
        195                 200                 205
```

-continued

```
gat gat cta tgg att tta cat gat tgg aat tgg ata aat gaa att gca      672
Asp Asp Leu Trp Ile Leu His Asp Trp Asn Trp Ile Asn Glu Ile Ala
    210                 215                 220

ttt cct aag aac aat aag aag ggc agt caa ata gta ata acc act tgg      720
Phe Pro Lys Asn Asn Lys Lys Gly Ser Gln Ile Val Ile Thr Thr Trp
225                 230                 235                 240

aat gtt gat ctt gcg gag aag tgt gcc aca gcc tca ctg gtg tac cac      768
Asn Val Asp Leu Ala Glu Lys Cys Ala Thr Ala Ser Leu Val Tyr His
                245                 250                 255

ctt gat ttc ttg cag atg aac gat gcc ata aca ttg cta ctg aga aaa      816
Leu Asp Phe Leu Gln Met Asn Asp Ala Ile Thr Leu Leu Leu Arg Lys
            260                 265                 270

aca aat aaa aat cat gaa gac atg gaa tca aat aaa aat atg caa aag      864
Thr Asn Lys Asn His Glu Asp Met Glu Ser Asn Lys Asn Met Gln Lys
        275                 280                 285

atg gtt gaa cga att gta aat aaa tgt ggt cgt cta cca tta gca ata      912
Met Val Glu Arg Ile Val Asn Lys Cys Gly Arg Leu Pro Leu Ala Ile
    290                 295                 300

ctt aca ata gga gct gtg ctt gca act aaa cag gtg tca gaa tgg gag      960
Leu Thr Ile Gly Ala Val Leu Ala Thr Lys Gln Val Ser Glu Trp Glu
305                 310                 315                 320

aaa ttc tat gaa cac ctt cct tca gaa cta gaa ata aac cca agc ctg     1008
Lys Phe Tyr Glu His Leu Pro Ser Glu Leu Glu Ile Asn Pro Ser Leu
                325                 330                 335

gaa gct ttg agg aga atg gtg acc cta ggt tac aac cac cta cca tcc     1056
Glu Ala Leu Arg Arg Met Val Thr Leu Gly Tyr Asn His Leu Pro Ser
            340                 345                 350

cat ctg aaa cca tgc ttt ttg tat cta agt atc ttt cct gag gat ttt     1104
His Leu Lys Pro Cys Phe Leu Tyr Leu Ser Ile Phe Pro Glu Asp Phe
        355                 360                 365

gaa atc aaa agg aat cgt cta gta ggt aga tgg ata gca gaa ggg ttt     1152
Glu Ile Lys Arg Asn Arg Leu Val Gly Arg Trp Ile Ala Glu Gly Phe
    370                 375                 380

gtt aga cca aag gtt ggg atg acg act aag gat gtc gga gaa agt tac     1200
Val Arg Pro Lys Val Gly Met Thr Thr Lys Asp Val Gly Glu Ser Tyr
385                 390                 395                 400

ttt aat gag cta atc aac cga agt atg att caa cga tca aga gtg ggc     1248
Phe Asn Glu Leu Ile Asn Arg Ser Met Ile Gln Arg Ser Arg Val Gly
                405                 410                 415

ata gca gga aaa att aag act tgt cga att cat gat atc atc cgt gat     1296
Ile Ala Gly Lys Ile Lys Thr Cys Arg Ile His Asp Ile Ile Arg Asp
            420                 425                 430

atc aca gtt tca atc tcg aga cag gaa aat ttt gta ttg tta cca atg     1344
Ile Thr Val Ser Ile Ser Arg Gln Glu Asn Phe Val Leu Leu Pro Met
        435                 440                 445

gga gat ggc tct gat tta gtt cag gaa aac act cgc cac ata gca ttc     1392
Gly Asp Gly Ser Asp Leu Val Gln Glu Asn Thr Arg His Ile Ala Phe
    450                 455                 460

cat ggg agt atg tcc tgc aaa aca gga ttg gat tgg agc att att cga     1440
His Gly Ser Met Ser Cys Lys Thr Gly Leu Asp Trp Ser Ile Ile Arg
465                 470                 475                 480

tca tta gct att ttt ggt gac aga ccc aag agt cta gca cat gca gtt     1488
Ser Leu Ala Ile Phe Gly Asp Arg Pro Lys Ser Leu Ala His Ala Val
                485                 490                 495

tgt cca gat caa ttg agg atg tta cgg gtc ttg gat ctt gaa gat gtg     1536
Cys Pro Asp Gln Leu Arg Met Leu Arg Val Leu Asp Leu Glu Asp Val
            500                 505                 510

aca ttc tta atc act caa aaa gat ttc gac cgt att gca ttg ttg tgc     1584
Thr Phe Leu Ile Thr Gln Lys Asp Phe Asp Arg Ile Ala Leu Leu Cys
```

-continued

```
        515                 520                 525

cac ttg aaa tac ttg agt att gga tat tcg tca tcc ata tat tca ctt      1632
His Leu Lys Tyr Leu Ser Ile Gly Tyr Ser Ser Ser Ile Tyr Ser Leu
    530                 535                 540

ccc aga tcc att ggt aaa cta cag ggc cta caa act ttg aac atg ccg      1680
Pro Arg Ser Ile Gly Lys Leu Gln Gly Leu Gln Thr Leu Asn Met Pro
545                 550                 555                 560

agc aca tac att gca gca cta cca agt gag atc agt aaa ctc caa tgt      1728
Ser Thr Tyr Ile Ala Ala Leu Pro Ser Glu Ile Ser Lys Leu Gln Cys
                565                 570                 575

ctg cat act ctt cgt tgt agt aga aag ttt gtt tct gac aac ttt agt      1776
Leu His Thr Leu Arg Cys Ser Arg Lys Phe Val Ser Asp Asn Phe Ser
            580                 585                 590

cta aac cac cca atg aag tgc ata act aac aca ata tgc ctg cct aaa      1824
Leu Asn His Pro Met Lys Cys Ile Thr Asn Thr Ile Cys Leu Pro Lys
        595                 600                 605

gta ttc aca cct tta gtt agt cgc gat gat cgt gca ata caa att gct      1872
Val Phe Thr Pro Leu Val Ser Arg Asp Asp Arg Ala Ile Gln Ile Ala
    610                 615                 620

gaa ttg cac atg gcc acc aaa agt tgc tgg tat aaa tca ttc ggt gtg      1920
Glu Leu His Met Ala Thr Lys Ser Cys Trp Tyr Lys Ser Phe Gly Val
625                 630                 635                 640

aag gta ccc aaa gga ata ggt aag ttg cga gac tta cag gtt cta gag      1968
Lys Val Pro Lys Gly Ile Gly Lys Leu Arg Asp Leu Gln Val Leu Glu
                645                 650                 655

tat gta gat atc agg cgg acc agt agt aga gca atc aaa gag ctg ggg      2016
Tyr Val Asp Ile Arg Arg Thr Ser Ser Arg Ala Ile Lys Glu Leu Gly
            660                 665                 670

cag tta agc aag ctg agg aaa tta ggt gtg atg aca aat ggc tcg aca      2064
Gln Leu Ser Lys Leu Arg Lys Leu Gly Val Met Thr Asn Gly Ser Thr
        675                 680                 685

aag gaa aaa tgt aag ata ctt tgt gca gcc att gag aag ctc tct tcc      2112
Lys Glu Lys Cys Lys Ile Leu Cys Ala Ala Ile Glu Lys Leu Ser Ser
    690                 695                 700

ctc caa tat ctc tat gtg aat gct gca gga atc tca gat ggt gga aca      2160
Leu Gln Tyr Leu Tyr Val Asn Ala Ala Gly Ile Ser Asp Gly Gly Thr
705                 710                 715                 720

ctt gag tgc cta gat tct att tcc tct cct cct ccc cta ctg agg aca      2208
Leu Glu Cys Leu Asp Ser Ile Ser Ser Pro Pro Pro Leu Leu Arg Thr
                725                 730                 735

ctc gtg ttg tat gga agt ctt gaa gag atg cct aac tgg att gag cag      2256
Leu Val Leu Tyr Gly Ser Leu Glu Glu Met Pro Asn Trp Ile Glu Gln
            740                 745                 750

ctc act cac ctg aag aag atc tac tta ttg agg agc aaa cta aag gaa      2304
Leu Thr His Leu Lys Lys Ile Tyr Leu Leu Arg Ser Lys Leu Lys Glu
        755                 760                 765

ggt aaa acc atg ctg ata ctt ggg gca ttg ccc aac ctc atg gtc ctt      2352
Gly Lys Thr Met Leu Ile Leu Gly Ala Leu Pro Asn Leu Met Val Leu
    770                 775                 780

gat ctt tat cgg aaa gct tac ctt ggg gag aag cta gta ttc aaa aca      2400
Asp Leu Tyr Arg Lys Ala Tyr Leu Gly Glu Lys Leu Val Phe Lys Thr
785                 790                 795                 800

gga gca ttc cca aat ctt aga aca ctt tcg att tac gat ttg gat cag      2448
Gly Ala Phe Pro Asn Leu Arg Thr Leu Ser Ile Tyr Asp Leu Asp Gln
                805                 810                 815

cta aga gag att aga ttt gag gac ggc agc tcg ccc cag ttg gaa aag      2496
Leu Arg Glu Ile Arg Phe Glu Asp Gly Ser Ser Pro Gln Leu Glu Lys
            820                 825                 830

ata gaa atc aga ttc tgc agg ttg gaa tca ggg att att ggt att atc      2544
```

```
Ile Glu Ile Arg Phe Cys Arg Leu Glu Ser Gly Ile Ile Gly Ile Ile
        835                 840                 845

cac ctt cca agg ctc aag gag att tca ctt gga tac gaa agt aaa gtg      2592
His Leu Pro Arg Leu Lys Glu Ile Ser Leu Gly Tyr Glu Ser Lys Val
    850                 855                 860

gct ggg ctt gct cag ctg gag gga gaa gtg cgc aca cac cca aat cac      2640
Ala Gly Leu Ala Gln Leu Glu Gly Glu Val Arg Thr His Pro Asn His
865                 870                 875                 880

ccc gtg ctg cga aag agg gag gac cga agt gat cac gac ctt gct tgt      2688
Pro Val Leu Arg Lys Arg Glu Asp Arg Ser Asp His Asp Leu Ala Cys
                885                 890                 895

gac gcc gaa gga tcc cct gtt gaa gtg gaa gca acg gat ccc ctc cca      2736
Asp Ala Glu Gly Ser Pro Val Glu Val Glu Ala Thr Asp Pro Leu Pro
            900                 905                 910

gag cag gag gga gag agc tcg cag cga aga gat aag cac agc tca agc      2784
Glu Gln Glu Gly Glu Ser Ser Gln Arg Arg Asp Lys His Ser Ser Ser
        915                 920                 925

tgg ttt tat caa gtg atg atc tcc tcc tcc att ggc atc tcc ggt cgt      2832
Trp Phe Tyr Gln Val Met Ile Ser Ser Ser Ile Gly Ile Ser Gly Arg
    930                 935                 940

ccc tgc ttc tgc ggc tgc gca cac ctc gct gtt ccg agg agg ggt gct      2880
Pro Cys Phe Cys Gly Cys Ala His Leu Ala Val Pro Arg Arg Gly Ala
945                 950                 955                 960

gat cta agg agg ctt cca ctt tct tca att gcg tct cac gct ctc gat      2928
Asp Leu Arg Arg Leu Pro Leu Ser Ser Ile Ala Ser His Ala Leu Asp
                965                 970                 975

tct tcc ctc tcg ggt atg aat tgt ttc aat ctg acc ttt tct cgt gat      2976
Ser Ser Leu Ser Gly Met Asn Cys Phe Asn Leu Thr Phe Ser Arg Asp
            980                 985                 990

atg cta ctg gtt cca gca tga                                          2997
Met Leu Leu Val Pro Ala
        995


<210> SEQ ID NO 12
<211> LENGTH: 998
<212> TYPE: PRT
<213> ORGANISM: Oryza minuta

<400> SEQUENCE: 12

Met Ala Glu Thr Val Leu Ser Met Ala Arg Ser Leu Val Gly Ser Ala
1               5                   10                  15

Ile Ser Lys Ala Ala Ser Ala Ala Ala Asp Glu Thr Ser Leu Leu Leu
            20                  25                  30

Gly Val Glu Lys Asp Ile Trp Tyr Leu Phe Arg His Gly Val Gly Arg
        35                  40                  45

Ser Asn Gly Gly Pro Val Val Gly Met Val Ala Ser Gly Asn Gln Ser
    50                  55                  60

Cys Leu Ala Ile Asp Ser Tyr Ala Glu Asp Ile Arg Asn Gln Ser Ala
65                  70                  75                  80

Arg Asn Val Asp Glu Ala Glu Leu Val Gly Phe Ser Asp Ser Lys Lys
                85                  90                  95

Arg Leu Leu Glu Met Ile Asp Thr Asn Ala Asn Asp Gly Pro Ala Lys
            100                 105                 110

Val Ile Cys Val Val Gly Met Gly Gly Leu Gly Lys Thr Ala Leu Ser
        115                 120                 125

Arg Lys Ile Phe Glu Ser Glu Glu Asp Ile Arg Lys Asn Phe Pro Cys
    130                 135                 140

Asn Ala Trp Ile Thr Val Ser Gln Ser Phe His Arg Ile Glu Leu Leu
```

-continued

```
145                 150                 155                 160

Lys Asp Met Ile Arg Gln Leu Leu Gly Pro Ser Ser Leu Asp Gln Leu
                165                 170                 175

Leu Gln Glu Leu Gln Gly Lys Val Val Val Gln Val His His Leu Ser
            180                 185                 190

Glu Tyr Leu Ile Glu Glu Leu Lys Glu Lys Arg Tyr Phe Val Val Leu
        195                 200                 205

Asp Asp Leu Trp Ile Leu His Asp Trp Asn Trp Ile Asn Glu Ile Ala
    210                 215                 220

Phe Pro Lys Asn Asn Lys Lys Gly Ser Gln Ile Val Ile Thr Thr Trp
225                 230                 235                 240

Asn Val Asp Leu Ala Glu Lys Cys Ala Thr Ala Ser Leu Val Tyr His
                245                 250                 255

Leu Asp Phe Leu Gln Met Asn Asp Ala Ile Thr Leu Leu Leu Arg Lys
            260                 265                 270

Thr Asn Lys Asn His Glu Asp Met Glu Ser Asn Lys Asn Met Gln Lys
        275                 280                 285

Met Val Glu Arg Ile Val Asn Lys Cys Gly Arg Leu Pro Leu Ala Ile
    290                 295                 300

Leu Thr Ile Gly Ala Val Leu Ala Thr Lys Gln Val Ser Glu Trp Glu
305                 310                 315                 320

Lys Phe Tyr Glu His Leu Pro Ser Glu Leu Glu Ile Asn Pro Ser Leu
                325                 330                 335

Glu Ala Leu Arg Arg Met Val Thr Leu Gly Tyr Asn His Leu Pro Ser
            340                 345                 350

His Leu Lys Pro Cys Phe Leu Tyr Leu Ser Ile Phe Pro Glu Asp Phe
        355                 360                 365

Glu Ile Lys Arg Asn Arg Leu Val Gly Arg Trp Ile Ala Glu Gly Phe
    370                 375                 380

Val Arg Pro Lys Val Gly Met Thr Thr Lys Asp Val Gly Glu Ser Tyr
385                 390                 395                 400

Phe Asn Glu Leu Ile Asn Arg Ser Met Ile Gln Arg Ser Arg Val Gly
                405                 410                 415

Ile Ala Gly Lys Ile Lys Thr Cys Arg Ile His Asp Ile Ile Arg Asp
            420                 425                 430

Ile Thr Val Ser Ile Ser Arg Gln Glu Asn Phe Val Leu Leu Pro Met
        435                 440                 445

Gly Asp Gly Ser Asp Leu Val Gln Glu Asn Thr Arg His Ile Ala Phe
    450                 455                 460

His Gly Ser Met Ser Cys Lys Thr Gly Leu Asp Trp Ser Ile Ile Arg
465                 470                 475                 480

Ser Leu Ala Ile Phe Gly Asp Arg Pro Lys Ser Leu Ala His Ala Val
                485                 490                 495

Cys Pro Asp Gln Leu Arg Met Leu Arg Val Leu Asp Leu Glu Asp Val
            500                 505                 510

Thr Phe Leu Ile Thr Gln Lys Asp Phe Asp Arg Ile Ala Leu Leu Cys
        515                 520                 525

His Leu Lys Tyr Leu Ser Ile Gly Tyr Ser Ser Ser Ile Tyr Ser Leu
    530                 535                 540

Pro Arg Ser Ile Gly Lys Leu Gln Gly Leu Gln Thr Leu Asn Met Pro
545                 550                 555                 560

Ser Thr Tyr Ile Ala Ala Leu Pro Ser Glu Ile Ser Lys Leu Gln Cys
                565                 570                 575
```

-continued

```
Leu His Thr Leu Arg Cys Ser Arg Lys Phe Val Ser Asp Asn Phe Ser
            580                 585                 590

Leu Asn His Pro Met Lys Cys Ile Thr Asn Thr Ile Cys Leu Pro Lys
        595                 600                 605

Val Phe Thr Pro Leu Val Ser Arg Asp Asp Arg Ala Ile Gln Ile Ala
    610                 615                 620

Glu Leu His Met Ala Thr Lys Ser Cys Trp Tyr Lys Ser Phe Gly Val
625                 630                 635                 640

Lys Val Pro Lys Gly Ile Gly Lys Leu Arg Asp Leu Gln Val Leu Glu
                645                 650                 655

Tyr Val Asp Ile Arg Arg Thr Ser Ser Arg Ala Ile Lys Glu Leu Gly
            660                 665                 670

Gln Leu Ser Lys Leu Arg Lys Leu Gly Val Met Thr Asn Gly Ser Thr
        675                 680                 685

Lys Glu Lys Cys Lys Ile Leu Cys Ala Ala Ile Glu Lys Leu Ser Ser
    690                 695                 700

Leu Gln Tyr Leu Tyr Val Asn Ala Ala Gly Ile Ser Asp Gly Gly Thr
705                 710                 715                 720

Leu Glu Cys Leu Asp Ser Ile Ser Ser Pro Pro Pro Leu Leu Arg Thr
                725                 730                 735

Leu Val Leu Tyr Gly Ser Leu Glu Glu Met Pro Asn Trp Ile Glu Gln
            740                 745                 750

Leu Thr His Leu Lys Lys Ile Tyr Leu Leu Arg Ser Lys Leu Lys Glu
        755                 760                 765

Gly Lys Thr Met Leu Ile Leu Gly Ala Leu Pro Asn Leu Met Val Leu
    770                 775                 780

Asp Leu Tyr Arg Lys Ala Tyr Leu Gly Glu Lys Leu Val Phe Lys Thr
785                 790                 795                 800

Gly Ala Phe Pro Asn Leu Arg Thr Leu Ser Ile Tyr Asp Leu Asp Gln
                805                 810                 815

Leu Arg Glu Ile Arg Phe Glu Asp Gly Ser Ser Pro Gln Leu Glu Lys
            820                 825                 830

Ile Glu Ile Arg Phe Cys Arg Leu Glu Ser Gly Ile Ile Gly Ile Ile
        835                 840                 845

His Leu Pro Arg Leu Lys Glu Ile Ser Leu Gly Tyr Glu Ser Lys Val
    850                 855                 860

Ala Gly Leu Ala Gln Leu Glu Gly Glu Val Arg Thr His Pro Asn His
865                 870                 875                 880

Pro Val Leu Arg Lys Arg Glu Asp Arg Ser Asp His Asp Leu Ala Cys
                885                 890                 895

Asp Ala Glu Gly Ser Pro Val Glu Val Glu Ala Thr Asp Pro Leu Pro
            900                 905                 910

Glu Gln Glu Gly Glu Ser Ser Gln Arg Arg Asp Lys His Ser Ser Ser
        915                 920                 925

Trp Phe Tyr Gln Val Met Ile Ser Ser Ser Ile Gly Ile Ser Gly Arg
    930                 935                 940

Pro Cys Phe Cys Gly Cys Ala His Leu Ala Val Pro Arg Arg Gly Ala
945                 950                 955                 960

Asp Leu Arg Arg Leu Pro Leu Ser Ser Ile Ala Ser His Ala Leu Asp
                965                 970                 975

Ser Ser Leu Ser Gly Met Asn Cys Phe Asn Leu Thr Phe Ser Arg Asp
            980                 985                 990
```

```
Met Leu Leu Val Pro Ala
        995


<210> SEQ ID NO 13
<211> LENGTH: 99090
<212> TYPE: DNA
<213> ORGANISM: Oryza minuta
<220> FEATURE:
<221> NAME/KEY: misc_feature
<222> LOCATION: 23216
<223> OTHER INFORMATION: n = A,T,C or G

<400> SEQUENCE: 13

aagcttggct ttctcttcat gaacaagctg tcgattggtt tggattgtag cctcgatgtc     60

cttgcattcc cggagatcgg ctaacctctg cctggctttc tccagtttga attgatgctg    120

ctcgaggtag acagctggag taagagcatc gactaattcg tccggaagag aggcttggat    180

atctgcaaat cttgcccgga tcgagccaca gttggtcacc aggttatcta gtgatgctcc    240

tagccgatgg gatatgtctt cgagtgtttt cttcacatca tcagacagga gagctgttgc    300

tttactggtg gtgtcttctt ctatttcatc gaggtaatct ttgatgtcaa aggagaatag    360

atcggctaag acctgcaaga gacaatatca tggatgatta aggatcaaga tatgattggc    420

cgatctcaag tttatgttaa taaaacttac tggaatagta ggtgcagcta attgttcctc    480

ctcttcaaca tgatgactac ctgcagccga tggagtgcgg ccgcctgatt ctacctgcat    540

aagaggggaa gaaggaggag gaggctgcca aagggataaa tgttagatat aatcagccca    600

agtcagttaa tgagatgata gaagtatctt actggtggag ctagtttagg ggttggagta    660

accgatttct tcctcacggc aattttcttt ctctatattt attaaaattg tgaggaattg    720

gctataaagt aaatgactgc aaaagtggac agagaaagtt gcttaccctt gccaattgag    780

ctggagcaga agggaatgga ggagcctgct taggtgaagc cgatggtgtt ttttcagtat    840

cgcttatttc ggctgcagct tggtcgatgt cttcctcgat ttcttcttca tccagagctt    900

gttcgatgga tggatctagg gcaggtagat cgtcagctgg cttagctttc tgtcttagcc    960

ttcttcttcg gagccggggc tgaagtatct gcagccgatg atctggttct ccgcttcttg   1020

ccggcatcgg ctggttctct gatgagtcct cggagaagtg ctgaggtctt tggggcattg   1080

tagccgatgg cagaaggaga tggcccacct ccattgggaa tcaagcttgg ggcatattca   1140

atttctttac cactattact ccggcgagga ggagaagatt ctgttgtctg cagatcagaa   1200

gaaaaggtta atcaaggttt aaatcggctg ttggttattt aagtaagagt gataaagtga   1260

agacttacct gaggaatggt atcagggaat aggtccgtca tatacatgga ggccaattgg   1320

tggaacaggt gcagtttcca ttcaccccac tatctgtcaa atgccctact cctgaacctt   1380

gccagcttta tgttctcgat gctgcccaac ggaggtccgg ggatgttcaa cagccgatcc   1440

atcattaaag ttgaggagat gtcgcttctg cattggatct tgtcggcaaa gtacaggcca   1500

attggcaatt gtcccattcc aaattgtttg gccaatgaca tcggatgata aaactcgtag   1560

gagacttgga tatttctccc ttgatggatg ccgactggga ggatacatgg gctgatagca   1620

gtagtaaaga tttctctgga ttgctgaaac ttttcatgat taatatcctc gaacctgaaa   1680

tcggctggca gttcgaaatc cattgagtcg gcatagaaga accaaactca ggcatttttt   1740

tggactccgt cataaaagct gaagaacaag tccttcagaa gttcaaccga taattttgtt   1800

cctgcatcag ctggtgtaga tgcatactct ccgtatgaca tacatctgcg atgggtgcgt   1860

tcttctccat catcttctac aatcggctcc aaccttggaa attcagcttc tgtcacatat   1920
```

-continued

```
ggccgattga caactttcat tactaccagg ttcagccaag attgcaagag ccaccatggt   1980

ccacctgttc taaccactga gccgataatt atcttggccg atgcgttgtt taacatctgg   2040

tatagatagc cgagaaggat tttgcctaag ggaaattgtt tcttcgttac tagggcctcg   2100

gctaagaatt gccagttggt tgtaggaccg cagcttgatc cgcataaaag gaattttacc   2160

aaccacatca gcagaaaagc tacttgttct ttaggagtga ctggcccttt gcccatatat   2220

gctgtgatat atcctgacca acccccaatg ctcttagttt tgaactcaaa agtgttcttg   2280

gtgtttaggc tcatggggtt agccgatgag gttacatcta ggccagtgag catgataata   2340

tccagcagcg ttggggtcat cagcccttga ttgaaaagaa aggcattgag agtgttggac   2400

cagaaataag ttgcagccgc caacaggggt tcatctttgg ccgaatttgc tactgtaagg   2460

gctagggctt ggctgattcc gatctcatcc caatgggctt gcttgctatc cgatatccgc   2520

ttataccata caggccagct ttctccagaa gaaggccagg atttgaaggt gtttttccaa   2580

tggcttgtgt ttggattggc cgacctaaaa ggagttctat tggtttaggc tatgataaat   2640

tcagtagggt ctagattgcc gattggaccg agaaagtatt gttggtcatg caacagactg   2700

ggaaccacaa caagattgga aagatgctac aagaatagag aaggagaaaa cgggataagg   2760

cgagcgaaaa ccggtctaat gaacggaaaa gggatctagc cgatggggac ttaccttagc   2820

gtattcggct gatgatgcgg cggtcggact ggtggaggtc gacatcgtcg cgggtggaga   2880

tctggccggg agtggaatcg tctggaaatc gccctgcgcg tcgaggaggt cgccggagaa   2940

agaagacggg atctgcttga gcggtgaaaa cggagaccat ggcgtgaaga ttctctgggg   3000

cgacgattag tatttaaagc agagcgataa cggtcgggaa aatggcaagt gcgagtttct   3060

ctcggagtcg gtatatggca aatccgaaac attatccaat attccggact tggggggcat   3120

gtgttaacga ccaaatttgg taaattctat cactattagc atcggagatg aaaatcagat   3180

cgaagtggaa tccaagatga agatcgttgc ggagacagag taaaaatcgg ctgcagtcta   3240

aatcggctaa ggtcaggatc ggcagagtcc gagttggacg gggctagccg atacaaccga   3300

ttccgataat atgacccggt gaacgtcatt gggtgattcc gatgagcttc aaggtgattg   3360

ccatgcttgg atagagtcct gggaaggcga ttgtatctat taattaggat attctatgta   3420

atttccttag agatatgttt gggcaaaagt ctgccgtaaa gacttatggt atcttagagt   3480

ttgttagaga taatagtcgt gtccgttatg gacgtatctt gtaatcctcg ggtataaata   3540

gacccgagcc ctatgtaaaa aaaaaggaca acacatccaa tacaatctcg gcgcatcgcc   3600

accctttgc tttactttta tttcgacgag ttcgtgctct cgggttgagc tgcatcggtt   3660

tcgatcttca acaagaggta aaacttgtca tgacgactta tgttcttagg atttgtgctt   3720

ccatctttat gacactctaa tcttgtctat ataattcgtc gagttatcat atatctcaca   3780

tagtcttcga taatatcttt atctaaccta taatcggcta acatctgcta atggaaggca   3840

gctgattagg ttagataatg acattaactt agattatgtg atatatctac cactctatga   3900

aactttcagc ggcttgattg tctagatatt gttcttcttt tcatacttaa tgctgcatca   3960

gttgagtttg atctattaag tcgtgcttag aattgcaatc tctagcctgc tttctggttg   4020

ccgattaggg tagtatcgga gtttcagccg atcttatctg atttaactac ttttattcta   4080

tatgcttgat tgacacgtta aatccaccct ttatgttagg attttattgc atctaagtat   4140

attaagctta tgtttggtat attctacttg ctttaatatc ttagtataga gtggtatcgg   4200

agtattagcc gatacatgct agatctacct gatcagctat gttttgaatg tatataaccc   4260

tactattaat atatatttcg atctaagtga tttatactgt ctcggcaagg caaccgatct   4320
```

-continued

```
atcccaatca cttgatttaa gtatataccg atataaggat tatatatcat taatgtgtac   4380
agttgatcga gtagatttag ttctgaattg cttgttgata tttgccgatc gatgtacgca   4440
tgacatcggc ttgaaataaa tgatatgtca tcggcatcta gccgatcggc tatcatttat   4500
gggattaatt gcggtttctt tgttctatct cttgttgatt gcaggatcaa atcaactggc   4560
acgctcatac atccgaaggc gagttttgga cctgcactgg agttaagcag atctcccagg   4620
cctcgtgttt tctgtcaaca taattatata agaaatctta ccaaaatttt agcaagttaa   4680
taaaattttg gcaactatgc taaaattttg gcaatgccaa attttggtaa ggtttttttt   4740
agcatcaaag tgaacaggcc ctggataagg gaatacgtac ttttatcttt gctgattcat   4800
ccaccgcagt gtccgtcttc ttgtactgtt tacgtattgt ttgaatccgt cttcgtgaca   4860
cacaaccttc cccttcaccg ttcgcgagat gatggcctcg cggtcgcggc tccgcctcgc   4920
cgccgccggc gagaacccta tcccacactc caagtccggc ggggagggag gaacggagag   4980
gaagccggag gaggcgctgc ggcgggaggt gacggacctg ggcggcggca gcgaggtggt   5040
gcacgtgccg cggttcgtgc cccgggaggc ggcgtggggg tggttcgact acctcgacaa   5100
gcgcatccca tggacacgcc ccaccatccg cgtattcggc cgctccgccg tccaggtaca   5160
gagaggtcac cgccgccgcc cgcgcctctc attgaaccct tcattttaat ctttgtgggg   5220
cttccctaat cggtcgcaat tttgctctg ttgttcattt gataaatttc tactagtgct    5280
aagatttcgc tataggttgg tgcattatcg ttgattcttg gaggaaaaac catagtacta   5340
tcttgcttgg tgagattctg aatatggtgc tgaggttgtg gtacttcggt gagtctgaag   5400
aatggttact gcaggcagtg ttgcttacga tttagctgtg gcccttcggc ctggggctta   5460
caaatttaca ctaggcattt gcgtttcccc ggtaaaagct ggttgaattc ataggaaatt   5520
ggcataatga tagtgactgc agctgatccg gatcctaaga aatcatagtc ggcagaaata   5580
gcatcgtgca tgtaattgca gtattggtga gttgttctct ttaacgtctg agctgaagtg   5640
taatttgtgg gcagaaataa actatataag tacatataca ttagtgggat ataaacaaac   5700
tgataggtac accagtggct ctgataaata ttactccctc catcccaaaa tataacaact   5760
tttgggtaga tgagacatat tctagtacta tgaatttgga taggggttat gtccagatcc   5820
atggtactat gatacgttcc atccacccta aaatcgttat attttatgac ggagggagta   5880
actgctaagt ttctgatgtc ttatgtccca aacgatggta gctcctaagc tctgtaatac   5940
cattgtcttt ccagaaaacc acggttacca ttgtcttcca attggagaca cattgatagt   6000
gtaactgttg tgaaagattc tagctcaagt atcccattct cttactgttc tgcagccgag   6060
agatacatgc tatgtcgcgg acgaagggct aacagatttg agatatagtg gccatcagcc   6120
tcatgcacat tcttgggatg aattccctgt gctcaaggat atcctgaagg cggtgagagc   6180
tttgccatga ttattctttg caatgctata tatgatttgc agttaatttc aagcattagt   6240
attctaaata gtatcaacta gtttgtattt gatgatgggc atctcaaagc tctcattcta   6300
tctagtgatt tgctgattaa tgtatgttca ataggttcat gaagccctcc ctgggagcca   6360
ttttaacagc ttgctcctaa acagatacaa gactggttca gattacgtct catggcatgc   6420
tgatgacgag ccgctgtatg gacctacccc agagatagca tctgtcaccc tcggatgcga   6480
acgagagttc ttacttagaa agaagccgac gaaatcgcaa ggtaagcggt gcacacacta   6540
ggaaaatttt tggactggca gcctcactat catttgtaga ttttggagtt tagatcacat   6600
caactccgaa atcgatccct attatttccg tcgaagaaaa gattgatccc ttttaatcta   6660
```

-continued

```
ccatccagct tcacttggat ctggggaagt tgcgccgaag cggctcaagg tcagtgctcc   6720
tcagcagcat tctttcctcc tgaagcatgg gtcgctgctt gtgatgagag gctataccca   6780
acgggactgg cagcactcgg tcccgaaacg agctaaagca agctcaccga ggatcaatct   6840
gactttccgg cgagtgctgt agcatctttg tgtacagcgt cggaggcagc ttccgggcag   6900
gtcgggcggc tgcctgggct ccatcgctgg cgcgtacact agagactatc tataacatgt   6960
atataaaaat taatagatca caggaaaaca ctattagtca cacaggagcg atggtgtttg   7020
ccactgtttg catggtagcg atcttatctt tgcctccctc gatcttttgc aattgtgcaa   7080
acttatcacg gacattgttt tggggagact tgatgtttgt gttctgcaac tctgttagtg   7140
catcatacat tctggcatca tgttgtactt gtatcagcta gtccgtactg tgtgcaccct   7200
agtatgcgca gaccttagga tttggtcaaa ataacagatt tagagagatt tttcgttagt   7260
actagttact gccctgtttg cgtctagttt tgtgtgaacc ctgtaacaaa tttgacagta   7320
atacacggct aatgctgtgt ttctggaaaa ttttaaaatg tactggttca agtttcaatg   7380
attcatacat ctgaactcag ttgaactttg tacagatggt tacactggag tcaaaactct   7440
taggacagaa tatcattatt atgctcaaac ttaacatcat aacaccaaac ctaggctgcg   7500
ttcggtagta gtagtaccca atccatctct ctctttttca cgcgtacgct tttcaaactg   7560
ctaaacagta tgttttttat aaaaaatttc tatacaaaag ttactttaaa aaatcatatt   7620
aatccatttt aaaaaaaaat agcaaatact caattaatca tgtaataata gacttcattt   7680
tgcgtgccgg ggaggactcc tcccgaacag agccctaata taggatctac cgatttactc   7740
atcagtccca aaatataaga aattttgtac ggatggaaca ctccagattc gttacactag   7800
gaaatgtccc ctccgtccaa aactccttat attttgggac ggatgaagta agtgctaacc   7860
agttcagaaa acagaaataa tgttcaacac aagcatatgc tgtgatacag catctgaagt   7920
atcaactcac atgtcacatt ctacatgcaa aatctgctgc ttcagaataa ggcaccccaa   7980
aattgggatg cccattctag ttgtacagta caatccaaga accattgttt attgtttaca   8040
acatttctac atgagtttta acacataatc actattcctg caaaataatg ctaaacggat   8100
atgttacatg acctgtggcc ctctcaagga tacgtataca atgaaattcc agggcacaat   8160
gccatagcta attaagttgg aaacaagttc tagcatctag taacattaga agcaaatcct   8220
attccactgc tcttctatac taaacctgtt gctattgcaa agaacatttt ctacatcaca   8280
actgtcaatt ccaaggtcaa ttaaatgaga tatccacatc cccatccgct gcccgtgaaa   8340
tctgcatcct acgaagaata atcaaccgag aaagcaaagc ctatgttgct ttagctgtgc   8400
gtttttcca gacactctgc acatttaaca caaacagtaa aagaactgta acagtaagaa   8460
tgaggaagac tggtacaata ggttcagagc acaggcgatt ttcttacaag agtctcgttg   8520
tcagattcct ccttgctgtt taaattatgg tcatcaggtt cctcctcttt tggctcatca   8580
cctttgccag acactttctc agcttttgct ttcttggcta ctactacttc tttctcattg   8640
cgtccatctg agataacaga acaattgtgc tctcaacttc cttgcaagaa acagcatgca   8700
gattatgggt aaacagtgaa ccgtaaaatc aaccccaaat tatcatacca gatttttttat   8760
cattatcaga atctgagtgt gcgagagaac ttgatgaatc cgaatcaata ttcgcatcac   8820
cggcagcatc aacagaactt ttaccccta tctttctgcg tttgtttttc ggcagtcctt   8880
ttggtttgcc tttcctcttt gggggtgagg gcctgcaaga taggggtaag accaattgca   8940
ccaaggtttt caagtctaat cattttatat gggcttacct cttttttgac ttctcttgtt   9000
caggcggcgg agtttgcttg ctgctggtaa tgcttttatc ctgagctctg caagttcaga   9060
```

-continued

```
ttacatatca aacaaactga tgtctatgac acacgtatca gtatgaaata attagaggtc   9120
ttaaatatgg aggagctagt tcaggtggca taagacatcg tttgttcctc ttggttacat   9180
gaggattcta gaatcatctt attctatgat aaaatgcaag atgtagtcag gagatagcac   9240
tttttgttta gttgttgaac taattactgt tcaggatgcc taattcccca gtgctgtaca   9300
ggacattttc ccagatgctc cagtgaagtt tattatgcag tgcactatat gcaagaggaa   9360
aatccagctt accgtccttg gtttctccct gaatgatcct tttttcgggc ctgcaataat   9420
ttgtaaacaa caataaacaa aaaaaaaact atgacctaat ttaaagagag tttttatgac   9480
acaatttacc atgctatacc tttacaggcg ggtcatcact tgcaacaatt tcccactttt   9540
ctttagctag gttaagcact tcaacatctc catcatcata tagcacctat gtagagaagc   9600
agtcttttaa atatatctgg tatatggtgc attacaactt agaattatat tccagtttga   9660
actagaatta taaatcatac aactgttgca tgttgtttat gtgctcatag tggttgacac   9720
tactgtagcc tgaaggataa cctggtggca tcggctgcta gtgatgagag gactataagt   9780
tgggggtgaa gaacttgagg gagagattta tagattgaaa ttcattgctc aattccacta   9840
gaccagacaa attcctgaat gtctcttata tataggccag cacctaacca tccaatctaa   9900
tagatagcca actactctaa ataaatcata tctctaagga aacctcctcc tcctctacac   9960
gtgtctcccc ggccatgacc ttatttggtc cgactgtgga ccgtggccct tggcctaatg  10020
cccatgacaa tagtggctga gcaccaagca ttctactatc ttcatataga attgacaaaa  10080
tgaaaaggtg caaagcaatt cattgctttc catacttata tttgtgacaa taaaatggat  10140
caaatagata caacatgtcg ataatttaat gcaccatttg agggaacata ccgtgtgtct  10200
tctttttgat gaatcaaaag attccacaac accttcataa aatctggtaa agaaaaaagc  10260
aattaaaatc taggccatct tcagaaatta gatagcacat gaagaataac acagatagag  10320
aactcacttc ttatccaacg gccaccaaac ttttattctc tttccaatca ggtcctcact  10380
gcctgtgtca tgtgttgtgc actgcaggca ttaattggtt cttagtaatg atgtttgaat  10440
gaaattttca ctggagttga acaaagtgaa taccattggc acacatactt tattctagtg  10500
attttaattg aaatattgca tgaaatttct cgacatgtca gaatttctta cagaacaaaa  10560
gaaaacaata gagacaacct ttgctagacc agaaaccaat tttggcttct gccttttgat  10620
cgacccattt aaacttcccg aatcaacagt tcgcttacta ctgcctgcct catcagactt  10680
ctgcaagagt tcaacaaaaa tcaatgaatc agaacctgat tttcacctgt agatccaata  10740
gatacagcca tacagatgga aagaaattac ctttggacta ctactcaaga tttcagcgtg  10800
gggcttctta gcaccctttt tccctttgga tacaggggtt ttaacactag caggcgatgt  10860
taccaactca gtatcaaccg agtcatctct ttttttggcc ccctcaacct tattttcaaa  10920
tgagttgata gtttcatctg ggtcaacaga ctgcagtaga agctcatcac tgtttttgtt  10980
gcctttcgtt gaatgtggtc tactcttaga aactgatctc ttgcgttttg gtgttgaaaa  11040
atctacaggc ttgtcattac tctcttttgc atccatccgc tttttctttg gtttgctctt  11100
ttctgattcc cccaaatttt cttgattgtc caagtttatt tctctaacca gtcccaagac  11160
atcatcatct ttttccatgt ttattgaacc agattttgtc ttctgctttc tcccagcctt  11220
ttttgctcct tgagatttta aaattttcac aatttttcct agaggaactt cattaccaaa  11280
ttcatcagtc tcatctataa gcatcttatc cttgggagat tcaacctgga cggagagaaa  11340
gatctaacgt caaaggccag cagacaattg atgctgagac acagtatgga cagaaaaata  11400
```

-continued

```
agcattatgt acctcagcag actttgctgt cataagagcc tcaaaatggg ccaacacatt  11460
ctcgcaaccc ggccatatct gctcatcact ctcctacaaa atatcatata atgtcaaaat  11520
aagaagccta gaagagaaaa ggcaagaaag tgacacaaac tgtaaagcaa gtcttaaatg  11580
aatgggttgt ttcatgcttt gtcacaggct taacaagcat atatgacata ccacagaatt  11640
ttcattctga tccttctgaa ctggcgcata aagttgactg ggcagtgaaa ctgtttgagc  11700
ttctgatata tttatctgct cttgacataa tttctttcca ataaggatac caagatcaca  11760
aatagcatgc agtgtctgca aacaacatac ttcaaatcta agtcatacca aatagcaagc  11820
aagatgtatt acagtggatc agcacaaatt taaaacaaat gaactcatta attaaaacat  11880
tttcacacct tggtcttgtt aacatcaacc acatcttggg aatatttgat acttttaaat  11940
atagatacta ttgttgtgaa gctctccttt ttcatgcctg gtacactgtg ctgcaaaccc  12000
tcttccccca ggaggatcaa aagaagcaga tgcaatcgcc tggaaagagc tttttgataa  12060
gcatatatat gcaagtacag caacaatttc agctacaaga atttacgagg gtattgcatt  12120
cgatttatta ttctcaaaat tcaacaatca cagaacaaac tagagtctgc caagagacca  12180
taatttaaca gccataagtg tgattttgaa ttgagctaat tgacattttt tactggaata  12240
aagttgggct ctaattgact tttctcataa caaatccatc ccaaatgtta tttgcacctt  12300
tagggttagc aatctgatgt ttcacacgca aacttagaat tgaaagtgga attagttaca  12360
gcagcataca cttgtatgta cagtgtattt gagcagtgat caagtggtac tatgaagaaa  12420
aacgcaacgc cattacaatg atatcgttga agaaataaaa tcatctgatc tctttcagaa  12480
gatagcagat aattgaccaa cgatttaaaa gtctcatatt tccatgagtt gagggcatca  12540
attaaacaac attactagag ttgcttctac ccccaagtga ttataaccct gagtgattat  12600
aaagcatgat ttaatgatgg acggaaatta gttctctata agttacatgg gtaaaaaatt  12660
caatagacag attaaaacag aggcactatg tgaatgaact ggtcattatg tttggagctt  12720
aaagtattct tttcctccaa gcatgaccgt ggctattctt tttaatagat cagcaaggag  12780
aagggtccca aagtcaatat gttgggaaga gtctcataag ttgttgagta gcagggtagt  12840
gttggtgcca aggcttgtgt attgatgtgg ttttgcttgg gtgagtgtta tgttgcccct  12900
tttcttcgtt tgttctcttg gatgggtata gtgtgactaa ttctattttc cactcaagga  12960
tgaataaaca gagccccagc catctgttcc caaagaaaga aaagaacaag caaactaatg  13020
gtaaattggt aataagcatt agaaaaaaaa actttgagcc attattagat accagtaaat  13080
tggaccaaat gcttcaacat cctcatgctc ttcaatgtta ggacatgatg gatcatgaga  13140
gagggcatga accaaatagg aaatcatata ttctggataa gcagtgagca catttgtttc  13200
cgcttggaca gaaagttggc gcatcttaac ttgctggcat atctgcgcaa cctcaattat  13260
gttgtgctta aactgagaag ggaaagaaaa caaaagaatt aaagaaacat attagaatga  13320
gtacagtggt ggaaatcaat taatttttcg agtttagagt atgaacctct tcatactgtg  13380
gggcatgata atcatccata gctaacaaga aagcacaagc atattttgca tccaaggccc  13440
tttccttaat atattgatgt actttactaa gaaataattt cctcacctga ggaacatcat  13500
cctggtaata aaagaaacca taaatctcca aagaagatac aagtgaatca tgtgaaagga  13560
acagtaagag tatgctaagc tgtattatgc acaacgcata cctgtgaaat cctgagagtc  13620
aaatagaata catcaacagg cactttgtgg tcccattgtc ttgataagcg gagaacagct  13680
tttgctgccg ccagcctcaa atgggcctta tcaatagtgc tgcaagtaat ggagtagtga  13740
gaaataacca aacacacaga caaagagaga gagaagaatg gcacattaaa aagcatatct  13800
```

-continued

```
gttggtagtt tgctaccttg aaatcatatt tgcagaaata tcaccatatg taaggatatt  13860
cttaaggatg cccattaatt tttcaattcc cggatgtgct tgagcatctt tgcaaggttg  13920
acagctcttc accaaagttt taatgccata aatctaggaa gaaaatacaa aacaacatgt  13980
agaggtcaat taactttgat ggatggattg aagtgagacc tataaaacca taatttcact  14040
aaccttcaat aaacaacttt gagtactatc actccattca gatttatgag cagaaacgtc  14100
gcccgaatcc tggtgatgca ctccgaattg caataaaaat ggaaataaaa tggagaagga  14160
aaggagaaat ttaaagagcg taagtcttac atcattgcag tcaagaattt ttttagttat  14220
aaaatttatt atctcttctc cccttgtttc aaaaattggc attgctatct gagctataca  14280
ccccaaggat tgtaagatgg atggcaaatg cactttcttt tcctccaaca agtccacaag  14340
cctctgcaag gttacgaatg tagagcataa catgttagaa atctcaaata tatgatccaa  14400
gaagaaacag ctaacaacaa atttgaacct tgtaaagaac agatagagac atcaggccat  14460
catcttttgt tatagcagcc aaagcatgaa cagagtattt tgcctgcttc cgtgttcctt  14520
ccaaacatag ccgctctagt agaagagtaa tggaactgaa acagaaggca cagcatctta  14580
gttctatact cttatatcct tattaagtag tgaaaagaat aatgtctcat tcatttcaca  14640
aaagttgcac cttgatgaag ctagttgttc acgaatgttg ccaccagcct tcgacagaac  14700
atgagcaata ccctctttaa gtagttcatt atcctccttc aggagctcaa tgatatcttc  14760
ttcaagtcca gacaaaagtg aagggaagaa actagatact gcctgcaatg tgtaaaacaa  14820
gaagtaatgg gaactgtcct gctgaagcat gataaagcaa atacacacaa gggatataga  14880
agagataaac ttgctcagga agaaaaatat cgggcattca taaacataag taatctagta  14940
acggttactt gctagctagc ctgacaatgg tctttcaaca gcaatgctcc ttgctagcta  15000
gcctaacaat ggaattacca cacaacccca cgcaggcaac tcctgaacta gttgttgcat  15060
gcttccttca tggcaggaaa ggatgaccaa aacgtttcaa caaatcatac cgttaaaaga  15120
tccatgcatg atgacataag ttttgtattc ccagtagatt tttggtcaga agcttcagaa  15180
aggatctctt tgacatattc cttgttcaca agtaaatatg agcatctcat cgacaacgtg  15240
ctcacaaaat catgtaatgc atgtttttca ccaagtttcg ttagcaaatc aacctgcaga  15300
ttacaaataa tattcaaata tagcagcata caagtaaatc aaattaggta actgaaaagc  15360
aataaaaaaa gtcaagtata caccctttttt ttcatatgaa gagttcatat tggtcaagaa  15420
taatgcagaa aatacaataa aataactatt atagaggcaa ctatacctga ctacatgcag  15480
cactggatga gataaatgga accacaaaga agaaaagcta gtgttgcaaa caagctaaaa  15540
gaattctttt tcttaacata tactgctctt ttttctattt catattgcaa gccaaacaaa  15600
ataatcatct gtaatctgta aatcaaatgg agtagcaggt acccgaagag accaatcttc  15660
gttgaatgtt gttgaacaat caagcaagct tgtgaatata ttccagatgt tggcatcttt  15720
tatctgatga agcatgttca agtactcctc agactttgta tgatcattga acaaacgaga  15780
catgctccgg aaacacccca ggatcttttt tttcatatca ggggtatctt cctgcttgca  15840
aaaggaactg ataagatagt gatagaacag acagtaattc tgtagtgcat ttgactattc  15900
aagattcacc aacctggctt gtctgtcgaa gggacatgta cttcagcatt tcttgttgta  15960
gcctgaaatt gaagaagcaa caatatatca gagagagaga caatttatca aactaaacga  16020
tctctagaaa gtaaaaatag tgccagacct ctgtttttgc agaaaaattt gctcgagagc  16080
tttcatctca actttgtcga aatgtgtgac agcagttacc caatgtttca ctctttcctt  16140
```

-continued

```
tgttggatac tctggtggga acaatgaacc acataaaatt gattcaattg actctggtct  16200
gcatcaaata aatcaaacaa atcaatgggc atcacctaac cacaatatct tgccacagaa  16260
agaaaaggtg atgttatgga attcttgtct gatgtgttgg tgaaagagca atgtgaaatg  16320
ctattaagaa aatatcatgg aaagagtacc ataggaagca tgaaacatta tagatggagt  16380
agtacataga gcatatctta gaggtaagca aagaacagca agatatcttg catgtacaat  16440
ggggattgag gaagcatgac atctgatcat aaatattgag cagtttacag gtttgtatat  16500
aaagcataat acaaatcgcc acaaggatat taagtaccct tacctaaaat ctttgtcata  16560
gaggcatctt aatatttttc caggaatcca ctcaaaatca tcagaattta ctgagctatc  16620
agaaccactc tggcaataga acttgtagat gtcagccaat ctctccatgg tatagcactt  16680
cacagaaacc tgattttttt aaaaaaccaa ttatacacca tgcattcaag tgaatcgtac  16740
agattatatt catcaaacat aaatattgaa agatgcagca aggggcaaac agaactaact  16800
gatttatcac ggacacgctc cgcaacttgt ttgatagttt caactgggac tgcaccaagt  16860
gaatggcaag ctacatcaca aatagcagct accacttgct ttctcacatt ttcctcataa  16920
tccaacaatc tgtcacaaag tgcctctgcc aaggagacaa ccatcagtac aagcacaaat  16980
gatggcacat tcagattata ttatcagcta ttcagcaaat agctacttac tgataatctc  17040
ttgagcttca ggacgggaat ggtttgacat cagacatttt ttcaaatgct caattacaga  17100
aacacgaatt tctacagctc ggtcagtcaa tctcttcagg aactcatcga aaagagattt  17160
aaatgattcc aagataggga ttccaggtaa agagaaaagt tcgccaagta tttcaactgc  17220
tttagaccga gtttcaactt catctgccta gaaaatgcca attacaaact ctaattaaca  17280
aagacaaacc aaaatttggt cacttaaatt aagatatatg gatttttttt ccggaagatg  17340
gaagattatt ttctgttccc caggcaataa ttatttcata ttgcacagta ttgctttaag  17400
tatataagta aggttctaca taccagcagt tccccagtta tataaggtac caccacttta  17460
agaacctttg gagcacactg gtacaaatca aatatgactt cgtgatggtc aatgctatta  17520
ttggtagaag taccatcccc atccaaggat gatgtcagaa tcttccttat gtatggttca  17580
agttttcctg cagagtgctc tataacatgg cgagcaagct tgcgtgcagg caaagaaaca  17640
ccctagagat taaaaaaaaa attgcacatt aagacttatt gaaggaataa gtaaaggaaa  17700
aggacaaaat aatagagaag cagtttctct aacaaatcac agaataggtc caaaaaaaga  17760
tttaaaaatg gaaggcactc acagtttttt tccggcctaa agttgataga agtacattga  17820
gaaggctttc ctctatatcc tcgctttcat ctataattag ggccattact gattgcattg  17880
aatttacaat atttggctca tgattgtcac tgcatcaatt caaaacacaa tgagtaaaat  17940
atttaagcta tcaactagca gcaatattgc gtgtatgtca cttggtagca ttaatagtct  18000
tatagtcaat aatttctggt tgtgtgcttc tgatttagta caatagaatg aaatatttta  18060
catgtcaaat aacttggctc catgaaacag catactataa ctacactcgt gatggaatga  18120
ggagagatgg ttgatgcggt gttctaagtt gaggttgtta gcatatatgg gcttcctaaa  18180
ctgcaagagt tcaaagaaat caatgtttaa aacatataga gcagcacccc atatatcaaa  18240
actgcatgtt aacctgcatg agtgtaaatg tgggcatcca ctcattaact tctctttgga  18300
aattgaaggg tcgatagctg tatcatgact tctcaaaaaa tgccttaata ctgatcaaat  18360
aggtatgtca ttcaaatgcc agtaaatatg gtcctctaga tttgaattta caaacaagtc  18420
ctttacgcag tgcatatatt gaaaatgagt aagtacacat cttagtcctc aaacagaagt  18480
taaaacagca cttcgtgaac tcatacttga attctattga acattttttt aaaaataatt  18540
```

-continued

```
agaaacaagc atgataaaat aagtcatgtg caacaatgaa caaaatgtgg aaactagtcc  18600
atgtgcggtg aagtatataa aaccaacaac attacatcca aatggataca gaagtattac  18660
ctgataattt ctaaaaaaga tcggaacatg tctgcaatta gatcattgca ttcaaggtct  18720
aacatgacaa cacatgctcg gtatctcgca actgtttcca gaatagcaac tctcctgcca  18780
aaggatttac cattaacatc attgagtcca ctaaatgtat ccacaatcag atgaaacatg  18840
tcctgcaaat gaaattaaca ataatcctca aatgttgaat aaatatagta aaccgagtca  18900
aatataatta gtatattgct ttctggaagg atgcttgatg ataaatgata ataataccct  18960
taagacatca tcactgtatg gagcttcagg agcagttatt cttgtaattt cacagaagca  19020
tgttgccaat agtactttga catcttcatc gtggtgtttc aagaattcat ctctggcaac  19080
agcctttaga catggttgga tagtttccat cactgaggga cctggtgact gctctactcc  19140
atgtaggcat tctgcagctt gctgcagtac gatcagcatt aatagcatat ccagagctta  19200
cttaagcaag gaggaagcat ttcaagcata cagttagtat tgctacagat gcaagccagt  19260
caggctgtcc aaccaattga ccatattaat tcttttgttt gacaaattag tatacacagt  19320
caggcatgta tacaacaaaa atgatatcct ttaaatgtca agtgaaccat caatgagttg  19380
gaccaattaa taggcaatca aatatagtcg gtactgtact actgctatta ctccctgtga  19440
cccgttctag gaacagtact acatagcaga taaccatatt cttaagaatc aactttcttc  19500
agtcattaat accaacaaaa tttcagtgcc ccttataaaa aaaagtgtat tttttagatt  19560
tttaaccaag cttaaagcct atctgcttca gctaaacaaa ccaaaatggc tgattactaa  19620
gggggaagtt tcacatgcaa actacttgtt tctggagtac aatagttgca gtcgaatgaa  19680
tccaggtaac agtgtaacac ctaagcaagt tcaaaagata tgatccctcc taactatttc  19740
aaatcgggcg ctagctgaaa ggttccatac caaggcaaag agaacaagga aagaacaatg  19800
acctgattca ctctaaacaa tagcagaacc acagtaaaca caagagcaat tcagatgaac  19860
tggcattacg gattccaaac ctaaaaatag gtgtgcctaa acctaccaaa atggcctagt  19920
taatatatag gtgtcaatca aatcacccaa gtgcatttcc acaagtatca ttactgccta  19980
aaaatttcat ttacagataa agtagctgat gatccttcaa taaagatagt ggctgtctct  20040
aactgcaaac tcgataatcc gatctacatc acaatatcca atagcataga gttattggca  20100
ccagcacata caatacattg gtcaaaaatt taaactaggg tacaatgttg gccaactgcc  20160
atttttccta gctgattagc tataaacaaa agaacaaaac agaagtaatc taagagcata  20220
cagttagaaa agcactcaat gttacccccca caacagacaa gtgtcgggat acaaagagtc  20280
caccagtttc agattttggg atctaaaaag taggattcga atgagaacct accaagtaac  20340
tttattctaa gaacattgct gagaaataat accatgtgac catagaaatc aatgtactgc  20400
tagccgacaa aattgccata taaacattat cataggtcta gaagtgcttt ttgcatttcc  20460
gcttaactac tgaacaccat ccactacaat gttaagcttt aatatactaa gatcccaaaa  20520
ccctaacgat aagcgattaa gcacacaaaa caagccaaaa atacacatgg gtcccaccac  20580
tgcacaattg agcacccaaa accttaacat agttaaagtt cactatgttc ttagtcccta  20640
tagaaaatct aatcagccaa aagaagcaaa gagacaccta gaaggaaatc actaagtaca  20700
acagaaacac agcttccgaa ccattaactc cgaattaccc aacgcatttt ttattttggg  20760
aagcccacaa ctatcattca agctaaacca tcaactccag cagcaaaacc ctaatttgaa  20820
aaacacctac cttctaaaat cttgtacctt aaattggctg aataagcaag attcattata  20880
```

-continued

```
ttaactcaaa tgagctggtg tctgaatagt tcagaccata aaatttttttg acaagataaa  20940
caaattaaat ttattctaaa aaaattatct ataaaattat gaagacagaa atgtggtatc  21000
aacaggacat aaaatactta tagatatgaa ggcaaaactc taatatgtaa tatgtcctag  21060
gtctataagt ttccacatga acatgaaatt aatttactta aaagtcagct cactgaccaa  21120
aaatcagatt tttctcttct tcagtacaaa atgtcaatcc accacagaac caacctacaa  21180
aagtgaagaa cttgcaatag taaaaccgca acagcacgcc acgaaactag cgtctttcac  21240
cactaaaacc ccataaaccc taatctggca cgacaaaact gaacctccct aatccagcac  21300
gacaaaaagc tccaaatcgc agcattgcaa ttcatcaccc aaaacctcta acacgccaag  21360
ctccagcaga aaatgccttg cctcccgagt agtcccacca aacacagaac gggaacaata  21420
ctacaagcaa aacgcaccac gtacaccgcc aattccagca gaaacgcggc ctcccaaatc  21480
tcacccaaaa aaacaaacct tcgtctccta attacccggc acctgcacat aaaccgtgcc  21540
ttggacaccc tcccgagtcc caaacagcta atttcaagct aaagcaacca aattccatca  21600
ccaaaaaccc taattcgaac ccaaaacccc accacaatcc cccaccgccc taaaccctaa  21660
acctgccgaa ttcgcccaca gatccaccca aaacccgcaa cctcacaccc ccctcccctc  21720
ctccacaacg ccaaagcaaa agcaaccaac caacccaacc caagcaccga acctcccaaa  21780
gagcagtaac aagtcctcac ctcgagcagc ttggcgaggt cgtcggccgg gtccggcggc  21840
gccgcctcca gcttctcccc gagctccttc agctgctcct ccgctgcccc catccccggg  21900
ccagatcggc cgccaattca cgcacctccc tctctctctc tctctccctc tctctctctc  21960
tctctcgctg gggtttctaa tctgagagga ggaggagcgc cttgtctttt tggctctcgc  22020
tgtttcgaaa attggtgagg aggagagagg cggagagctc gtgaacggaa tgccccagtt  22080
cgggatcggg tttgggtctc tctctctctc tctctctctc tctctctctc tctctctctt  22140
ctctctctcc tgctgctacc gtttggaagt catcatgcgt cgggcacggc gccgcgtgtt  22200
ccgcgggttg ttctccgggg gttgtggctg acgcgtgggg ccaggaggag gggcgggccc  22260
gcgtgtcggt gggggggacg gtgagggggt tctcgggtgg gtttaggagt ttttttagga  22320
cagcgttttt tgttttttat tttggtttgg tttgggcctg cggggtggga tactgggatg  22380
ggagagagat gcgtgcgacg atggggcggt ggattcgggg ttaaactgaa gtgccggagt  22440
gcagtttgcg tttagggaaa tccggtgatc tacggtgtgt gagtgctgag tacagtacta  22500
ctagtttttt ccctccactt tgtattacgg tgttcaaaaa tagttgtttt tttttgccaa  22560
ttatgtcctt attaggaatg ttaattcgcg cacgtgttat ttatcacatg gattctaata  22620
aacctagggt ttatcgggac atgtacgagc agcgtcactg cggcccaagt ggtcgagcct  22680
cgaaaggatc gaggttccac agtgggcgtg ggatggaggg ggcaactagc ggaagagaga  22740
agtgggagtg tgcttagagg gatggtctga gaagcgcccg accgacggtc aatggtggtg  22800
acggcgaggc agggggtggc gcccactagc catgggttgg gagaaggcgg tggagtgggg  22860
tcggcggtgg gagaaacaag tgtcaaccag ttaggttggg tgcgcgcgga ggacagcagc  22920
aagcaggtat tactctgtca aaaaaacaaa ctctagctac gaatatggac acgtatgtgt  22980
ctagatttgt aattaggatt tgaccttttt tagacggagg agataggctg caacaatggt  23040
gtgcaaatgc gggagatagg agtggcatct tagaggagat tgagtgggag aggataaggc  23100
ggagagggaa atgagccgtg ggccagcatg ggtgggtcgg tgtatgcata ctagccttcc  23160
cctgcctcat tggttaaggt atgagttata agccaagaaa aacaaatgaa gcaaancgat  23220
attctattct aaaataataa aatgttctta gctgtccaga agctaaagct aaaaacaata  23280
```

-continued

```
gaaaaaccaa catcaaatct gaataccctc ttgagcggtt gtcggttttc acaataatag  23340
gcttgaaaca aggaaaactt tggatatttt tctgaaaatt aaaaattatg tttgaatttc  23400
ttgaatttgg tggtatatat gctaagcggt tccttagttg ttaacttcct tgagatggcc  23460
cataattact ataatcaaat ggttatgtcg acttttggaa ccttgtttca caaagattaa  23520
cataattgaa tgatttttac aaatatgcat gtgccagttg gagaaacccg agactactag  23580
tatggaagtc atcttttttt taaaaaaaat tttgaggttt caagtaaaaa attttcttgg  23640
ttcatgtaga aagttaggat tttaatttga agttgtagag ttttgagttg aaagttagtg  23700
gacctcccat aaaactatct atatatttca atttaaagtt tgactctaat gtagaaagat  23760
tcgagacttg ggttgaaagt tcaaggccac aagtaaaaaa gtttgaaaat ctgagtaaga  23820
agtatgaaat ctaggtcgaa gtttatttca tgagttgaaa gtttctttta tttttttcc  23880
aaggctatgt gtggagacct ctaaagagaa gggcatgcca tacggcgcat ggtacccata  23940
tgggaaaact ttgaaataca ataaccacca accattttgc ttaatatgtg atcgctctga  24000
tttataaatg attaatcaaa tacaaaccaa agggagaagt tgattaggag ctcttacccc  24060
acataacttg cccaagtcac atgttccaaa ttgcaatcca tgcagaaacc ttttaaagca  24120
ccacatcact tgcacttgtg tttacttagg taaccaacta ttcgatgttg attttgtatg  24180
gaagtttttt gtttttatag tataatgttt tatgtctaga atttctggca ctaggcagtt  24240
gccaaccgaa tattatacac cagtgttgtg aatattgttt aaaaaagcat atatcatgaa  24300
aaggagggtt atcgtacttg gttcctagta atattgaaat tggtcagaca tctagggttt  24360
ttaagctatc aatatagtaa attgcacaag tgatatacga acttgtaagg ttagtgcaat  24420
ctagtataaa acttgtaaaa tacttgttca tgtgcatgac ttgagtagta catgcaaaca  24480
aaggcaaaaa cgtcacacta tgtctaatct tgctgatgtg gatgttgatt aggatgctgc  24540
actcacacgc gacaagagcg ctaggcatgt tatgtttgga agtagccgta tatactggat  24600
tacttggttt ctattttgtt ttccttttct aacctgcatc cttctttcgt ttataaacaa  24660
cgcctttctc aacacaatta atgtgccttt gggtggacta acatgtataa acccatgtgg  24720
catcctaatc aacatccaag ttagcaaaat taacgtacta ggcatgtagg ccattttgac  24780
cttggttcgt agtaactacg caagttcgta cacaagttag ctataagatt cacacacgtc  24840
tcaatttcat atactacaaa tacaatttag taagaaaaaa aactattgta tctagaaaag  24900
ttatgtattt aaaacacagc atggtatgat tcctaattat cgatacatgc atggagactt  24960
gtcatattta gaatctttat cattacaata gtaaaataca gggacttctc aagatgaact  25020
tatccacaaa agacttctct ccatttattt atttcctacg aaagagttac cagattgctc  25080
gttgcataat ggctcatctg atgcagaatc ccagaatgag gttgtaaatt agaactattg  25140
tctctgattt caagtataga taattttaga ggtgtgcaca agagttgatg acctttatcc  25200
tacagctata ttatacattg aaaaatgatg tctcatttat atataggaga gatgccattt  25260
gtgccgtttc acacaatcaa atatttttct ctttatggct ccaaaggaga aatgcaccac  25320
tgcctttata ttagagatgg caacagttaa ttcactgtcg gggtcatct ccgcgtcccc  25380
gtcaccgagg tgataaaatt tcaccgtccc tgcccccgtc aaccacgacg gcgctatatt  25440
ttcaccagcc ctgatcacca cgcggtgaac ttttgccccg tggttacccc gtccccggtt  25500
aaagaaacac aaatcaaatc agcacttgag tagttaaaca caaatcagca cttgagcagt  25560
taaacacaaa tcaaatcagc gctggcggca agcttcgggc agctcccggt ggcgcggcga  25620
```

-continued

```
tggctgcagg ctcccggctg cacgacgaca actcccgcgc ccgcgtcgac cgctgcaggc  25680
gacaggtagc gcgacgctcc tggcggcgtg tcgatagagg gggcgggaca gtagcggcgc  25740
gcgcgagagg aggcgacggc gcgcaaggtg gctggtggtg gtggagtggt ggtggacagc  25800
ggtgcgccgt gcgcctggtg gtggtggttg tgtgggcgac cgcgtgtggc tgcagcggag  25860
agccgctgga ggagaggcgc tcgactcgat ctggaggagt ttgaccaaag actagggtta  25920
gcttttatat atacctgtta attgggcatt agtattatgg gccaaaacgt ttaaaaagtc  25980
tagatttagt catctataca gtaaagtcgg gtcaccgcgg ggggcgggga cggtgaatgg  26040
tgcaccatcc ccaccccgt catccccgat ggtgctaact ttggaaccat tttattcacc  26100
attgtggata gatattaacc atcccagtca cctaaaaggt gaattcaccg cgggaaaacg  26160
gtgaacgggg ccccattgcc atctcttctt tatatgtaca tgaaagctag ggttggagca  26220
tattgctcat gcctaaatcc aaagatacaa agcctatcca aaatggctcc atattcctct  26280
gcattctcca tccatctctc taaatttagc tccatatttt tttaatgacc catgactctg  26340
ttttcaccta aattggctaa atacttgtct tacttttagt tatttatgaa tataaatatgt  26400
taattactct taattattat ttttataaat tagttgctct taatgtatat atatccaact  26460
actataagat agggagtgag tttggatccc aagatttaaa aaggaagagg gggggggggg  26520
gatggacaca gagtaggata agatagggag tgggttaggg atatggatag agggggattt  26580
ttgggtgttt ctcttaaaga gaaaagtcta tatttagtta tgcaactatg gctttggtat  26640
gtgtctaagg ctctgttcat ttctggaagt tcccaacctc cacctcccat ttcccgccgc  26700
atgcttttta aactgttaaa cgatgtattt ttaaaaaata tttaggaaag ttgttttaaa  26760
aaaatcatat taattcataa gttttttat ctaatactta cttaacaatg cgttaattac  26820
cgttttgttt tccgtgcgtg gaggattagt tccaacccac cttgaagaac atagcctaag  26880
gcggagtttg tttcagcttt taggctgaaa ttttgtgatg ctacgtgaaa ttttgatgag  26940
ataagtcatt agcacgtgac taattgaatc ttaattatta caaaattaaa aatatatatt  27000
tatacatagt aattttattg aatgaaacgt accgtttagc ggttgggatg cgtgctcata  27060
gagaaccatg aagtagctat tccaaaacat tgcttagaac gcaccctaaa aaagaccatg  27120
gctttggtcc actttttgatt tctaaatcat gaactcattt acttttggtc catgaactct  27180
caaaaccgtt cgcatttcac cccataagtt caaaccagga ttgttttcaa tgatgtaacg  27240
tcaacatgga gttgaccagg gtgatgatga taataataaa caatagcaaa ataaagaaaa  27300
aaaatactgt gacctacata tgtcaaactt gcttcctttc cttctctctc cataatccta  27360
tatatgttat ttactttaaa ttgctaccta aaatgacaca tgatgccatg tccttaaaaa  27420
ccctaccgtg attatgtcaa ggtttgaaat atgaggcggt tataagagtt gaggggctaa  27480
cagttacagg gtttcatagt taagtgaact ttttttcttc ttaaaaaaca taacagagag  27540
tgcaaaacag aataggaagt gtgatataga ggtggattgt attgcctcta ctaaacgaat  27600
ctggaatttt acattgtaga ccttttaaaa acttatgtta caaatagatg gctagaaaaa  27660
tttatttcta gaatgagccc tttttgcagc accaacgcca ttattactat ggtccaacat  27720
gatagcacca atgacattat tgccatctcc cttgcccctt aaatggaagc taagggctag  27780
tttggttcgt ggccttaatt ggccttgcca atatttgtca atttcaatag tgtttagtgt  27840
ctatttggtt agaagccaaa ttttgacatg cctaaagaaa tagaccattt caatagtgaa  27900
attaggctgt tttgcttcaa tccaaacaca actttatctt gccaagatta gccatgccaa  27960
aacttactaa aatttgatat tgacaaaaat tggtaaggtc aatttaggtc acaaagcaaa  28020
```

-continued

```
ccagccctaa gtctcggatg tgaaggggtt acgttcagaa cctatttgta aaaaaattcc  28080
aaaatactaa aatataaatt atgtttctta catataggtg tttaatgtta aatgtaaccg  28140
aggacctatt tataattttt tttataaact attcattctt ttgaatttct tttataaata  28200
gattctcgac gcaagtgtta ttaccgttga cgcccttcat attagtgact tagcttttac  28260
ggtgaagagg tacaaggaca attatgctag ccccgcgaaa atgatctatt tctagaataa  28320
gtttttttaa aaatctattt gtaaaataat ttttcgaaaa taacaaaagt aaaaactgct  28380
aaacgaagag ttcctgcatt tcaaacaata ataaactatt aggaaaaaca cgtgatccgg  28440
tgacaacact agtttactcc tctgtgcacg tgggtccagg caccggttac cgtttggtgt  28500
tgtcctgttc cggttcctcg gtgtccagta gttccactgg gtggttggat ggtccgctga  28560
gcgcttgggg cccacgcgta gccttgttct ctggataaga aaactgcact tccatttctc  28620
gtgaaaatgt ctactggtag aacagagtat gggccggccc actaacttag cctaagtaac  28680
atacctcaat gggctctcat agcccaatac cccactgctg atttttttttc ttagggcatg  28740
tttaaaatgc tggcaaaata aacctttcga aaaaaaaatt aagtcgataa cattgtcaag  28800
ttttgatagg gtaagttttt ttttgggatg tgtttaattt ggtgcccaca tataggggtg  28860
gaaaaaaaaa agctcgaagc tcacgactcg aatttcaggc tcagcttgga tcgactcgag  28920
ttcggagtct taacgagtcg agccgagaca gctgttttgc tcgttaagct aacgagctga  28980
tcccgagcca gctcgcgagt cactttgtag gctcgttaaa ctctcatagc ccaagaatcc  29040
tacaggccac agcccaatca ggtggccgaa cccagtaaaa actccctccc cgactccctg  29100
tcttctctaa accctatcct atccgccacc tccaccaaat cgcaggctcg caggcggcga  29160
ctcgcaacca ccaccaacac caagcaggct gttatcgtcg ccttctcctt gtgccgtcgg  29220
agcgcgccca ccggctgctc ctcccgcagc cgcagggcca cgctgacgac gccgctcctc  29280
ccgcagccgt agcaccacgc cgaccacgcc actcctccca cagctgcaag gccactcgct  29340
acctcctagt ccctggaggc ttgaaccctg ctggtctgct tcatggatca ggagcgccgg  29400
ttggcaagca tggaatccaa gaaccgtagc aaggggaaga aattgtcaag agcttctccc  29460
tctagtttga ctccagccgg cagccacctc gcctctgttc agaagccacc aagatagaga  29520
cctaaagcaa atccaccaac ctcacatcaa gcaagtgtcg catcaatatt tttcacaatt  29580
tgtagcaatt ttttttccta attttgtcac tgattgaacc attcaacttg tgatgcacaa  29640
tctgtagtaa gtgttctata ggtttgtttt cttattctgt ggtgcactga tgatggacat  29700
agttatatat tgaattggat tatacaagga cctaatggag ggttcattca gttaacgagc  29760
taaacaagct caatgagcca gctcgagcaa gctcgctgag ttgagttgag tcagcatttc  29820
agctcgttaa gcctaacgag ccgagccgag ccgagatggc tttttaaggt agcgagccaa  29880
accgagcgag tcgagctgcc tcgatatcca cccctaccca catataggcc atcaaagttt  29940
ggcaacattt ggaggttatg atattttatt gtgacgttga taaattcctg tgagcattac  30000
caacgtttgt ttacaaacta aatgtattaa tatatcattt tcctaaaaaa aatgttacga  30060
ttttaaatgc catcaatatg aataaagccc ttaatctctc atcctactgg ctgccgtggc  30120
acctaatagc acatggcatg tccacgttgg caacgagcgc gccacgtaag tatgtgatgc  30180
tgcgaaaagg acaaggccag acagagtcac agagctagct gcgtccagct aagcctcgtg  30240
cacgtaccga ttccaatgcc ttctcctgga ggtaagtatt tttgttccac ttgattatat  30300
ttctttggca gatgacgtgg acgctgccac ctggatgctc tggaatccag cgaagtcagc  30360
```

-continued

```
agtcaaatta acaggtattt tacaattttt tttctgaatt attgtggtcg tgttgcatcg  30420
gtaagagtaa caccaagctt aactttcctt gatcgatgct gcttttactc aaacctggaa  30480
gagatggtaa tattttaatt aatcagtgag aaaagaaaaa ctgatgtgaa cgggacaatt  30540
tgcacgatgg gggaataata atattatttg ggttgggttt tgttaaatac tcctacttgc  30600
tttgtctttt ttctcgacca catgaccaaa tcgagctgtc acaactcgca cgtccataaa  30660
ttaagaatat tatgctaatg cagttgacat tcgacggcag ctagcaagac ggagtagctc  30720
accaaatact attgctatat atctaattca accagcttgg ataaatggtg agctgaatgc  30780
ttgctcaaac actcagactc accaaccata ttatcatgtg gctgtctatc cagattgtca  30840
agattttggt catgtgatat atgatatctc tataatgcat gcatgccttt ttaatgaata  30900
gttcaatttc ttacttttgc aggccaattt gttgtttgtg agtggtcaat ctaaaattaa  30960
atctaagata actttgatag gatggatgag tagatttttt ttaactaaaa tgtgaaattg  31020
atgtcaaatt tgcatgataa gttgccgttc caacgaatag cactagtaaa acacaatatt  31080
tcgtgaatgc atgatgtttg aaaatgatga aggtaaaaat taagttgacg cacgtaaaac  31140
aagaaagtca ttagtgtata attaattaag ttttaattat tataaatttg ataaatggat  31200
atatatgata ttttaaagta agttctataa tataaagttt ttgcacggaa tgtacatata  31260
gtagttttga taagtgctaa tgataaccga gctaaactct ataatcttaa tcatagaaac  31320
tcatgtgcta ttcagccagt ttagtcctac cacgttcgtt tggagaacaa aggagtgagt  31380
ttttttcgtt ttccgcgcgc acgctttccg agctattaaa cggtgcgttt tttacaaaaa  31440
ttttctatag aaaaattact ttaaaaatca tattaatcta tttttgaagt ttaaaatagt  31500
taatactcaa ttaatcatgc gctaatggct cacatcgttt tacgtatctt cccaatcttc  31560
tcctcactca caaataaaaa accaaaacat gaagttagta tacctcaact aattaggttc  31620
ctgatagtga aacccatcca tccagattta agttttaaaa ttagcacggg tgcttgtatt  31680
tacgagtagt tattctacca accaagttgt agacttgata cagtcgagtt ctacacttcg  31740
catatcttaa gatatgtcgg attagtcttc gaaagtactt atagaggtag ggtgtcttag  31800
acatatatcc gtctagtctt tgaaaatgtt tatagggatg gagtgtgtat atgtgtacat  31860
tcataagagt gagagtacgc gtgtttatat cagctgcgac tgtactatat tttaaaaaaa  31920
ctaatgcatc ctcatctaac gaactaaacc taccagagag gggaggagga atggtaggaa  31980
cactaaaaac cgaaaacttt tagcggaatt aaaagttacc ttcgaagctg atggagatcg  32040
gtctgaccgg cttgattgcc ctagtttgac cgcgccttgt tgccaatcta accggtgtag  32100
atcgaggtct gaccgccctt cgcgccatcg acgcttgttg ccgccatata actgccggtg  32160
tgaccgagca gttgcctctg gtctgatcgc tggtgatcta tcggtgtgat cgttgcattt  32220
gagcaaaaca caaattaaaa gatgtcttga aagtacgtag attgaatttt attgcttata  32280
ttcgtgttac aaagtacaac aacaacactt ctctcacaaa attcgactaa actcgaaacc  32340
ttaacttttc tctaaattaa actctcccaa aatcaataca aggatatctc aactccctct  32400
ctatttatac ccaaggcaag cagcctaagt cacgaatcta atttgtacaa gaagttctaa  32460
ttcactagaa aaccttcccg tacaagaaac aaacttatct catcataatt cgaatttcaa  32520
tcctcccaaa tttagactcc ttccaagttt gactccgctt ttcatacgca cacaatctcc  32580
cattgaaacg gtcaattagg cctagagggg gggtgaatgg gctaatttaa aaacttaagt  32640
aaatgcagaa gcagggtttt tcagaaattc tgaaaatgct ttacgaaaat tctgaaaatc  32700
acagaatatg cacaagtgaa agtaaattct agatctagct acatacaaca atgaaatata  32760
```

```
agcacaaaca acaactagac ttataacggt acaaacaagc aaagctagag gagggagaga  32820

ggtatatcac cgaggttgtt gcaataagag ttgttcccga agtttgaatc cttaagggga  32880

ttatactttc cgttgaggag ctcacaacga gctgggtctt tgctaaccct tttctcaagg  32940

ggttgcccaa agcactcctc cttccactag tggtatctag gggtaaaaac aattggaaac  33000

gatcggaatc gttagcatct cttcggaaac gatgctcgat cggctggtta gtcctcacat  33060

atactcaaac gaaaatgtta gtcctctcta atcatattgt tattaatcac taaaatcatt  33120

aggggcctag atgcactttc acccatttta tgcgacaaag aatcatcata aaacaatgtg  33180

cattgttctt tagactaagc atcccgtatg atattctgat tgtccagaca tcatcttctc  33240

ccaagttgac tctcgatcca tcaccgacaa cgctctcctg aggcatcaag acacacttac  33300

acaggaatca aaacaagaaa ccatatccga gcacaagttc tttcctaact tgactcgaca  33360

ttagcaaaca acaatattac acacatatag aaataatcta gaagtcataa ttatgagata  33420

aacacgagta tccaaataaa caactcaaaa ccaaccctaa tcaagatcca gccggtcttc  33480

ctgcacatac cacaccggtc tgcccggcct tactggtaca gtctgatcga cttcacacaa  33540

aaaaaacact tcaccaataa tcaccaaata ctaaattaat tatatatcat gccaattgtt  33600

catcacaaat taataataaa aacacacttt gatttcaaca attagttaac tgacagtcat  33660

atcgatatat agcaaatatc ggcaataatt gcacaagctc cctacatcta ttctcttagg  33720

ttctcctaga tcgatcacac tggtctactc ctttcatccc ataaaataca aacgttatcc  33780

caaatgttag acaccgtaat actacaaatc tggagaggcg tgattaataa tttctcatca  33840

accatagggg taataataat ccaaggctgt gtttagttcc acgtaaaaat tgaaagtttg  33900

aagaaattgg aacgatgtga agaaaaagtt agaagtttgt gtgtgtaaaa aagttcaatg  33960

tgacgaaaaa gttgaaattt tgaagaaaaa agtttgacta aacaaggctt agtcatggtg  34020

atggtaagtc agcccctaag ctttcacttt gacctattct actctcacac tgacgttgac  34080

attgtatcac agggcaccac ccatcccctc cttaattttt gtttgactat agtaaccata  34140

tcaatcaaat aggtgtgaaa gctaacctag attatttctg atcacactga tcacattctc  34200

actagctatt ctacactttc taccttcaca taggacgaca agtgtaccaa cctactgata  34260

aattatcaag cctcattttt cttataagtt atggccaaaa ttaaaatttt aaaaattagt  34320

tttaaattat tttgatgttg tttcatcacc tttttctagc tttagctaaa atgatataat  34380

tatagagaaa ataaaagtca taacctaaaa ataaatttta gctcattttt tatagcttat  34440

tagccgcaga ctattcaact cgaccctccg tgttttctca tataagccca taccatggct  34500

acgtttgaaa ctacaactct acaagttctc atattttatt ttcttatttt tcacaagtac  34560

gtttttgaaa ctgtaaaacg acgtgtgttt ctaaaatttt ctatagaaaa attactttaa  34620

aacatcatat aaatttattt taattttttt aactaatact acctctatcc tagaaagact  34680

gcagttttgc actattcata tccaacgttt gaccgtccgt tttatttgaa agttttttat  34740

aattagtatt tttattgata ttaaatgata aattatgaat aatactttat gtgtgactat  34800

tttttatttt tttaataaat tttcaaacaa gacggacgtg gttagtattt ttgttgttat  34860

tagatgataa attatgaata atactttatg tgtgactatt ttttttaaat ttttttataa  34920

attttcaaat aagacagaca gacaaacgtt gcacaccaaa atttataatt cataactaca  34980

gtcaaaatgg gacggaggta gtaattaatt aaccttgtgc taataaacct ctttttgtag  35040

aagaaatgag aagttcgaac acaacccgca cacccaaacc aagggggtgt ttagattgag  35100
```

-continued

```
gggtgtaaag ttttggcgtg tcacattgga tattatatat gatgttgcat agggtgttcg  35160
gacactaata aaaaaaatct aattacataa tccgtcagta aaccgtgaga cggacttatt  35220
aagcctaatt aatccgtcat tagcacatgt ttactgtaac accgtattat caaatcatgt  35280
agcaattagg cttaaaaaat tcgactcgca aattagtaac aatttataca attagctatt  35340
ttttagccta tatttaatat attatacaga tgtccaaact ttcaacacga tctaaaattt  35400
tcgggtaggc tcatcgaaag caaacaaaac gaacccccgc acacgaacgg tcacacgctg  35460
atcttttatc caaacccaaa aaagaaaaga aaatcagaaa aagtcccgcc actacctcta  35520
ctactgccgg ccctaccccc acagattcca ggcgccagct aagcacacac cgacgtgcac  35580
ccctcccctc ccgcatgcgt ttccactctg tctccgctcc acacccgagc ccggtcaaac  35640
ccaaccccgc cgcgccgtca ctccgcaccc gactcactgg cccccaccac ccaccaccgc  35700
cgctgccccg tgggccccgc ccccacccgc cgacgcgtgg gcccccacac gccgccggcc  35760
gcggcgggtc acatgcgcgt agtccaaact ccgaggcgcg cacgaaaaag agagagacaa  35820
aaaaaaaaga aaagagaaat tctttttagg cgctctaggt ataaaaatct actcctactc  35880
atcacctact tttccacttc gattcctctc cccttccccc tcctcttcct cctccgcttc  35940
ctccctctcc tctcctctcc tctccgccgc tgccgctgct gctgcgtgct cctctcatcc  36000
ccgtctcttc cccctccgcg cgccgcccac tcgctgggag gaggaggaag aggagacctt  36060
ccccggaatt cgtgctcgcc ggatcgggct cgccgcaatc catgtcggtg agtggtgctg  36120
ttgatgtgtt tcttttttct actgatttta gagttggtga ttggttgcgc tgtctagatc  36180
gagctgaccc gcctgcgcgt tggattgtat tgattagagg aagggaggct gattagcacg  36240
aggtgtggga aaaattagtt gtaaaaaaaa ttggaggggt taatagatgg gcgtttgtta  36300
agtgacgtaa ggcgaaagtg atgttatgct gttctgggtt agtaaggttc ttggcaatca  36360
gttttggtca aatcttactg gttcataggt gttttggtcg aatttcagct tcagatgaag  36420
tttgtccctc gtttccagga ttattggcgg tcagttcttc atcgttaggc ttttaattgg  36480
ttgaacagga aattggggtc atggtagaat gcgaagtttc tgaaaacata agtagagaac  36540
aaaagtagga gaattttgtc aattaggtac gatggaaggt caccgtcagc ttgttcaact  36600
actgttaggt tcaaactttg atcgtgcttg agatttcttt gctaaaataa ggggatatgt  36660
ggcaaaggga gaataaacca tgatatgatt tttgttactg actatagtgg ctgtaaatga  36720
gaacttgtgg aatcacagaa agttccaaaa aacaatgcag aaattgtatc ctttttttgtg  36780
ctttgcctag tccattttct gacttctgag atgaggtccc cgcatcacat agaactgcaa  36840
ttgcaattca atgcattcat gcaacaaaca gacagactac tgtcctataa catgagttat  36900
gacttacgag tagccttgca tattgtacat gcataagcca aagctgcttg tttattgtaa  36960
accagatgct ctgtaccata aaaaccataa tccattaagt tttcttgttt actttgttga  37020
acattatact agatacctat ggtgttgact gttacataac attctgttca ccatttggca  37080
attttccccc cttagtgaca ttcattcttt tgagatttca gtcatgcctt ccacatgaca  37140
aaatgttcca ttcaactatg atgtttggaa ttgggaaacg gtacacatac ttaatgtttc  37200
ttttactaat tctgattgaa agaatgcaac acatctttta atccacatgt acatacatca  37260
atcaatgctt tggagagagt gcatcatgga tcaatcatat tgatggtttt tagtaaacat  37320
tttacagcaa ttatttgtgc acatggccct catacaattt ttgttgggca ttcaaccctt  37380
gttttgaggt gttaaataaa ttattttttta ttatgttgtc aaattgcctg acctttgtat  37440
tggtggttgg gcatctagct gtgcactgtc aataactcct ggcggtgctc ctcttttttcc  37500
```

-continued

```
tggctgttga acttccaatc tgaccattca ttatgttcat atcttgtaca catgtggtga  37560
gatgtcaatt gctgtccatt gtatgttact atattttact tagcattgtt caactgtaat  37620
agacagtgat atatcataca tgtcaaatga aaccaacaca gacaaagcat atgctgtgtt  37680
gtcatcttct tatttcttgt actgttctgt tctgtcttga aggttagctg tgttagtcat  37740
ggcccactat ggattctcaa aaggcatcct ttatgttcat tagtttcatc tttttctatt  37800
ttccaatttt attagatggc tatactcgac tttgttcaca cataatctct aattatcaat  37860
cgtctggtca tgcttggcag gcctcaatca aatgccagcc cacccacggg aaatgggcca  37920
ggattgaggc ctgctgaaca aggtgtagag gtagatacac cctttaatgt ggatcatggt  37980
tcctttctag gaggaagcag gtcgtccctt gcccaagttt ggtgaatggg atgtcaacga  38040
cccagcgtcc gctgatggat tcacagtgat attcaacaaa gccagagatg agaaaaaggg  38100
tgggaatggg caagatactg attcaccctg caaagaaact aggactgaga gggtggaatc  38160
atatgccccc aagacaaact cggtatgtct attacattac tcacgcttat tataatatca  38220
gaatttcaat ttctccctga ttaatataac gatattcctt ttctcttgaa ctacataact  38280
agctagatgt cattaatctc attgttttca tgtgcagaag aaatggtttt gctgcgtgac  38340
atccagtcct acacaatctt gatgaaaacg agttccatgg gttgcaaaat tactatcctt  38400
taattttgct atatacatac tatccataag accttgtaga gatgcccaga ctctactgcg  38460
gtgctagatt gggcatctct taaaactttg aggtgtgtgt atgtatgtgt gagggttatc  38520
agatgcacat tcggataaat gaacttctga ttgtaattct agccttccgt cctgtgacat  38580
tctgtgatgt agtcgttatt cagtgatata atgaatctca cctatttata taactgcaca  38640
ctgtttctct tgctttccga ggaaacaaac actgttttac caaagttggc tgtgctccaa  38700
aagaggatta aattccatat gattctcata ttgcaattgc aattttgatt ctctcaccta  38760
ctaatatgcg attttggaat tttcctcacg tgccaaattt gcatattgca attttgataa  38820
aggatacaag cacagtatag ctcaatctcc ttggcgatgg aagttttctt aatattgtag  38880
gcaccacatt tctagctgat aatgcaacta tcgtggagat cataaagagg aggaattttg  38940
tggaagaagg acctggaggt tgggagtctt cggcctctac tcagtcaaat acaagaaaat  39000
attcctcaaa acttaatgca tgtgatgtag attcaaaaag aggtgaatca actagctgat  39060
aaggtagcaa aggatgtgag atcgcgacag ctaaatcctt caggtttatg attgtcaaaa  39120
tatcttgagt cttgctcatc ctagaaacct ttgttatgtt agagatttga agaaccattt  39180
cagagcaacg aattgtatta caactttaca agtcatgtgc tctgtttctg aaatggaaat  39240
aaaactgatg agttctaaaa aaaaaagatc catacattca tgcctgtaca cggacagcaa  39300
atctacatgt caaagtggat atcgccaaat tggtttcaga atttcatcat tgtgctcatg  39360
cccaatattt tttaattttc ggtgaggaac agatgagcat ctttcgtgct agctgcagac  39420
tcgggtgcac taggaatttc actggtttat ttcacacgat ttatttcagt tccactgaaa  39480
tttgtttgga attcatttgg ttcgagaaga ggcgtgagat acgagacttt gggagaggga  39540
aagggcagtt caatacctga tacttttgct cacttggagc ttgaccggag agaggggagg  39600
gagagtagtg aggggggagc agtcgatggc ggcggagacg gtggtgagca tggcgatgtc  39660
ggtgctgggc agcgccgtcg ggaaggccgc ctccgccgcc gccgacgagg ccaccctcct  39720
gctcggcatc cagaaggaga tctggtatgt gtgcgcacgc ttctgtaact ccataccaca  39780
tcggtgactc tccatggccc ctccgcggcg gcgtgtcggc gacctcggct tccatggccg  39840
```

-continued

```
ccgccgccgc cgcctcacag ccctgcttcg ccgcaatttc ttttttggtc ttttggtgat  39900
tccaacggat tcaggatcaa aaatgaaaca atccggagag cctattcacg cttcgcattt  39960
cactacccca aacttgtgga ttgtgaccat gcaaaccaaa attccttcag tttcatactt  40020
tcatatgctc aaatttccgt tgttttcata gaaacaaggt tatttatccc acttacatct  40080
tgcaaaaacc aaagtacagt tactcttatc gattttcatc tatacacatg ctagacgaat  40140
gcattgtagt ccaattcaaa tttctgatat attagttact aaccaagatg ctcccatgcc  40200
atgagcgcaa gttccattga caaggaaaaa cactttttta tgatttgagc aagttccacg  40260
ctggcgtcct cgttggcaca ccacgtaagc taaagtggca aaaaaaaaaa gaatttttct  40320
ctctacagtg agtcagtgac aaaaacttaa gtgcaaaatt aaaatgggta tttggataat  40380
cgccaaatct aaaagtggca aatagttaaa ttccccttt atatttctct cttcagtggc  40440
aaaaacttaa gtgcaaaact aaaatgggta tttggataat cgccaaatct aacagtggca  40500
aaaagttaaa ttccccttt atattagtcc ttgaggagct acggcaatgt ttgctagcac  40560
cggacaagat catccaataa aaacttagag attatacata acagtgtcac tgttactagc  40620
aaaattttcc atcctattgc atggttagta cattttttt ttgtgagaaa tatatggtca  40680
atgccatttg caatatacct ccaggctcta gtcaatataa gactacatac atatgcgatc  40740
tacattttgt actaggtctc taccaaaaga aggggtttgt atccttctgt tctcttaaat  40800
taatgagacg atttgtagga tctttctttt tcaagggatt gtgggagttc tgactctcat  40860
ggctaacgag gcgctctgaa tactagtagt ttatttccat ccatctattt atttatttta  40920
ataaatttta ttgcttttga atttatattt gtaggtacat caaggacgag ctgaaaacta  40980
ttcaggcatt cttaagagct gctgaagtaa caaagaagaa agatgacttg ctaaaggtat  41040
gggcagagca agtacgagat ctgtcatata acattgaaga ttgcctagac gaattcaagg  41100
ttcatgttga gagccaaagc ttggcaaagc aactaatgaa gcttggtgaa cgccatcgaa  41160
ttgctgtaca gattcgcaac ttaaaatcaa gaattgaaga agtgagcaac aggaatacac  41220
gctacagctt aatcaagccc atttcctcta taaccacaga ggatgagagg gattcctacc  41280
tagaagatgc tcgcaatcga tcaggtagca acactgacga gtcagaactt gtgggctttg  41340
ccaagactaa agatgagttg cttaaactga tagatgtcaa tactaatgac ggtccagcta  41400
aagtgatatg tgtggttggt atgggtggat taggcaagac taccctttgca aggaaggcat  41460
atgaaaacaa ggaacacatg aagaacttct cgtgttgtgc ttggatcact gtgtctcagt  41520
catttgacag gaaagaaatt ctgaaacaaa tgatcaggca acttctgggt gctgattcat  41580
tagacaaact cttgaaagaa tttagtgaga agttgctcgt gcaagtccag catctcgctg  41640
atcacttggt tgaagggcta aaggagaaaa ggtactttgt tgtccttgat gacctatgga  41700
ccatagatgc atggaattgg attcatgata ttgcttttcc gaagattaac aacagaggta  41760
gtcgcataat aataacaacg cgagatgctg gcttagctgg aaggtgtacc tctgaatcac  41820
ttatttacca ccttgaaccg ttacatatag atgatgctat acacttgcta ctagcaaaga  41880
caaacataag acttgaagac atggaaaatg atgaggactt gggcagcata gttacaaaat  41940
tggtgaaaag gtgtggttat ttaccgctgg ctatactcac aataggaggc attcttgcta  42000
ctaagaagat aatggagtgg ggaaaatttt acagagaact tccttcagag cttgagagca  42060
atccaagcct agaagccatg aggaggatgg tgaccctaag ctacaatcac ttaccatctc  42120
atcttaaacc atgctttctt tacctaagta ttttccctga agattttgaa attcaaagag  42180
ggcgcctggt agatagatgg atagcagagg gttttgtcag agccacagat ggggtgaaca  42240
```

-continued

```
ttgaggatgt tggaaatagt cactttaatg agcttatcaa cagaagtctg attcagccct  42300
caaaagttag tacagatgga gttgttaaga gatgtcgaat ccatgatatc atgcgtgata  42360
tcatagtttc aatttctaga gaggaaaatt ttgtgctgtt gactagggag aagatcactg  42420
ttgtagcgga ggagagcatc cgccatctag catttcatgg gagcaaatgc tcaaagatat  42480
gcttggagtg gaaccatctg cgctcagtaa ctttgtttgg cgacagacct gtggggcgaa  42540
cacctgcact ttgttcacca caatttagga tgctgagagt gttggatctg gaagatgcaa  42600
aattcaaatt cacacaaaat gatatcagaa atatagggtt gttgcgccac atgaaatatt  42660
tgaattttgc aagagcctca actatttata cacttccaag gtccatagga aaattgcagt  42720
gcttgcaaat tttgaacatg agggaggcaa atatctcagc actaacaact gaggtgacta  42780
aactccagaa tctccgtagc ctccgatgca gcaggaggtc tggttctggt tactttagca  42840
taatagataa tcccaaggaa tgcttgatga tcaccatgtg cttaccgatg gttttcttaa  42900
cttcaataaa tttcagtgac cgtgtgaagt taattcctga gatatgcatg tcatgttcta  42960
cccgttggtc tgatacaaag ggtgtgaggg tgccaagagg aattgacaac ctaaaagagt  43020
tacagattct agaagtcgtg gacatcaaca gaactagtag gaaggcgatt gaagagctgg  43080
gggagctaat tcagttaaga aaattaagcg tgacaacaaa aggcgccaca aataagaagt  43140
atcagatatt ttgtgcagcg attgagaagc tctcttctct gcaatctctc cgtgtggatg  43200
ctgagggatt ctcagatact ggaacacttg agtggctcaa ttcgattgca tgtcctcctc  43260
cattcttgaa gagactcaag ttgaatggat ctcttgcaga tacaccaaac tggtttggga  43320
accttaagca gctggtgaag atgtgcttat ccagatgtgg gctaaaagat ggtaaaacta  43380
tggagatact tggggcactg cccaacctta tggttcttcg tctttatcgc aacgcatatg  43440
ctgacgagaa aatgacattc agaaggggaa ctttcccaaa tctcaggtgt cttgatattt  43500
acttgctgaa gcaacttaga gagataagat ttgaggaggg cacctcgcca acgatggaaa  43560
gtatagaaat ttatggttgc aggttggaat cagggattat tggtatcaag caccttccaa  43620
gacttaagat tatttcgctt gaatatgatg gtaaagtcgc gaagcttgat gtgctgcaag  43680
aggaagtgaa tacacacccc aatcatactg aattgcaaat ggcagaggat cgaagtcatc  43740
atgacctagg aggtatataa ggatctaata tagtatgtga gcaatgaaaa tcgcatattg  43800
agcttgccat tgacagatca tggtcctgac caggccttgc atctgatggc gatgatgccc  43860
atgacaatcc agcgttgcgc tatcaaacat catgttgaca acaaagagtt cagtcttgca  43920
cttgagaacc taccctgtta ttatgtaatg acacgtttat atgcattgag atgaaaaata  43980
gacttaaata accatataat gcaacaccca aagagaagag aaatacaata tagacttatt  44040
ttccagccat ttgaacacag cccacaatga gggatggaaa atatacttat tctgtggaga  44100
agtacgatgg gctatcgtgc ctttgggtcg gcccgagtcg tattagccgt gcctgggccg  44160
tgtgtgcagc atgttggtcg ggccgtgccg gcccgactaa ccttggccca ggtacgactg  44220
ggcttgggcc gtgccatgcc gggcagccca tttggctaac tatactacac tatatggtac  44280
tccctccgtt tcatattata aatcatttgt cttttttcat agtcaaactt atttaaattt  44340
gatcaagttt ataacaaaat atagtaatat tttcaacaca aaacaaatat tgtatcaaaa  44400
tatattcaat gttaaatcta atgaaactaa tttggtgtcg tgaatgttgc taatttttttc  44460
tataaatttg gttaaacata aataatttta actataaaaa agtcaaatga cttgtaatat  44520
aaaatggaag gagtagtagc tactcgtctg ttaaaaaaaa aagtttcctc ctaacataag  44580
```

-continued

```
agcaaattgg ctcgacacaa ttcacctgct atttatctgt ctttcgcctt gtaaggtagt  44640
ggtgcaggac tgcaggtgca gcatgcgtac acaattgatc tgtttttact tcttgcaatg  44700
agataagatg gagaacgttg tgtcagtcac tacatcttaa actgcctgat gctcatccaa  44760
aatgagaaag atgttccaaa ttacacattg tgcattccga tatgaatgat ttctcactct  44820
atatatactc tagatgttca gatttttact aagaattgag gtggttagtt gaatggagat  44880
atttttctag ttcggtgctt tagatatgtt ttgcttttgc ctaatgacta tttttttttgt  44940
tttattaagc tatgctatac tacttacggt tataacggtt atagatgaat atagttcttg  45000
tttattatag ctcttctgaa aagtgcagtg tacaactagt tgtgttattg ttaactgata  45060
aaacatagaa atgttgattt aatgagctac attgatctct tcttcgttga tatgagaagc  45120
ttggtttgag ttgtttttat attctaataa atatttgtta ctggaatcgc tccattttcg  45180
tatttgaaaa tatttgatta tgttttttat gtggggtttc tgattccaat taaaaaaatg  45240
aaaataaaaa tggtatgatg gtttccgttc gttatgcatg cgcggaacaa tggatctcac  45300
taatcaagtc gcacgcagtt ctttatatct tgttgattat ggcttgtgaa gcatagattc  45360
accgaattaa ttgggatgct aaattagtca catgcatacc caagcttgca tatgacgtta  45420
tgtagataga gatggccaat ataatgcgct ggaaagtcca aagtgaggat gcaaaacatc  45480
ttatagtggg tagtggagcc atgcaaggac ctggtctaaa gcgcacctaa accgtcatgt  45540
ggactgccat tatagttaaa gttaggggga atatgattct cttcatgtgc acctaaactt  45600
taatatgcag tgaaacgaac gctatgatat gatgataagc ttaattcctc tctctgctca  45660
gactgttcag tgcaaaagct accaacgagc ttgtctcctt gtgcggtcgt gagcttgctt  45720
gtgctaagct tgaagggaga gtcgaacgaa tccatggcgg agacggtgct gagcatggcg  45780
aggtcgctgg tgggcagtgc catcagcaag gccgcctctg ccgctgccaa tgagacgagc  45840
ctcctgctcg gcgtcgagaa ggacatctgg tacgtactgc actgcgctct cgtttatcct  45900
agctcggttg tatcgacttc cagcttaatc tttttaataa tgaataaaaa cccggacttg  45960
ttatccataa gtggatatac acagtcaaaa cacgcgacaa gttcttaggc tcttaattaa  46020
tctcgaaatt gaggaacacc atgaaacact aaaagagagc tcgaagacta ggaaagaaaa  46080
ctagaagact aagctttgaa agtcttctaa atccaagcat ctcgacattg atcatccttg  46140
tgcaacatca acccttccta ttgcttcacc agaatcggcg tcccttgtgg agatctctgt  46200
tgtaacgtca aggggaaaat cggagaagca gaactagtcc gcgctgcctt cgctacgcca  46260
tctccgcctt agaggatctc atccacgaaa catccaccat ccaaacggga aacagtttta  46320
aacactcgtg gacgttcacc cgttcatcta aatggttatg aaaaattttc aaaaaaaata  46380
acatgatagg ttaacatgta atatatcatc ttataaatat gcaagttcaa atttgatttc  46440
tacaagttgt aacaaaaata acaaatttta ctgtgaatat acgtaaacta gttaaagttt  46500
aatttgttat ttttgttaca acttgtagaa gtcgaattta aatctgtatg tttgtgaaat  46560
gagatattac atattaacct atcttataat tttttttaga aattttttag aattatttag  46620
gtggcataca agaaacggat ggacatccac aaagagatta gtatccatct ccacatccaa  46680
acccgttgtt gcaccatctg tcgaatctgt cgaatccggc tgtggacgct cggaggcaag  46740
agctagctca cccgtcccac acacacaccc aacgacgtca caagcgcctc cgaacaacgc  46800
caactgataa cttggcagct cctacgtgcc gacgtcgcgg tacttgccgg cgctcctagc  46860
gcatgcaccg tcgaaccaca ccgtcaccga ccagctaccc accgccgccg acttctgcct  46920
catctgccat cgtcgcccta gcccaagtta tcatcgtggc aattgccgag gctcctaagt  46980
```

-continued

```
gtgccacggc cgaggcaaag ttctaactga atcagacagc caccaccgac acttctgctt  47040
catctgccat cgccgtacta gttcaagttg tcgctgtggc aatcactgtt gttattgccg  47100
cgccctgacc cctatcgtcg tcgctcttag cgcgtcgtcg agccgaccag ccactgtcgt  47160
gcagatgaaa aaaaaaaaca cattttggcc tgagagatct gcttagttcc attgcaggtc  47220
caacatgctg tgagatgcgg gcgtgccagt cagtttgatc ttgcaactga caagatatat  47280
aaacagcaga taaaacagcc tatcgactaa caagccgatg gagtaattcc agccgatagc  47340
cgatattagc cgatgccgat tctagccgat gtcgataggg ttttgaacta tcggctatat  47400
gtccaatgta ggcaatgata taaagacaat tggctgatga taataaaata taaaaatata  47460
atccaataga aaccaatcgg ctaataataa gtattgatcc gatagttaaa gcatacatcg  47520
gctaaaagtc cgatgtcata aaatccaatc gatttagata aacagtgaaa cctttgttgc  47580
aatcggctaa atccaacttg tatgtaatct tcgtaagccg atgaacgtcc agataactta  47640
tcggctagca cctcgataaa acactagcat gaacctatcg gcttaacaag atttatatta  47700
tcaacaacaa tctagtaggt cggacctaac cgatgcaaca cgtattagat atgataatct  47760
aatactcgat gagccaatag atctgtctaa tgtgatggat ataacaaatc tatttataaa  47820
agcattgcga ttgtagagat atatcggcta agacagaata tcagacctaa ctaaaccgat  47880
gcgtctctaa acacaatgca attaattaga gatataattg agatatcagc taggcaaata  47940
tatcaaccaa actagagcga tccaagagat cggagcaatg cagccttgaa caacaccaat  48000
gtagccgatg gattcaccag ggtcgacgga atgtaggact taccccttcc ctgaagatcg  48060
ggctgaacca atgcagtccc atgtcaggtg ccaaattccg ccggttgata agtaaaacct  48120
cagaaaagag gatgacgatg cgccgagagt agtattgatc gagagataaa ttgcaatgac  48180
cctggatgta catatttgta cccatgggta gatattagtt cttgtaggac aagaaagaaa  48240
ctttcctaaa gataaaatga aaacataaag tttttattgg atactaaaca cactttccta  48300
aagataaaag gaaactaaac cctgcctaat taatagataa actgccatgt cgtatcctcc  48360
ttgaactcga actcttttag ataagcttcc tttaactaat ctttacccga atccatcaag  48420
aatacaaatg ttggcattga tagttttcat cggtcaattc taggactttg aagccgatac  48480
tgactctaag ccgatgacta ctttgggctt accaaatttt gttgttaaca tgtcgcgacc  48540
accatcaccg gccagccacc ctgatcattg ttgttgactc agcattcgcc aggctgagca  48600
gtccacatac atgccgccat ctccatggca ctgtcgttgc cgccccttc tcctagagcc  48660
gccgcagcgc tcttcgacac acctactgca tcgtcgagca gtcgtgctac cacctcctcc  48720
atcgaccata gccgcctctt ctgctgcacc ggatccaccc acaccaacca ccagatacag  48780
tcaagccctc attcccggat cccatatcca tccatgccac tactgtgctg cccagtccaa  48840
ggaatggagc gaaggaggaa gccccgccgc tgccctcccg gcggccacat gcactccagt  48900
gccttgctcc gacggcagcg aggttggaaa atgggtggca gcggctaggg tttatctggg  48960
gagaaggaaa aggagaggga gggggggggg gagggtccac ttccagctta attagcctag  49020
atcttattga caaatcagtt gctgggtgca caaacatgtt atttttttg catgaccaat  49080
cttgaacact taggtatgtt agttgagtgg acactggtct atctgaaaca tctcttcaca  49140
tggaggctgc gaatgagttt tctttttgag agaccaaagg ttcgttgtat gttaagtgat  49200
aaagccttgg taagaaatgc taccacaaac gaactaataa ctccaaacgt aaagtggagg  49260
aacccgtatg ggtgactcga gtggcgacaa actctagcac ctccacctcc ttggacgggc  49320
```

-continued

```
tgcggcggtg ctttcggcat cccagtcttc ttggaggcat catctagaat taaggtcttg  49380
ttattgctta gcatgcctta gggcacgtcc agtgtttagt tcgactaaaa cttccatgaa  49440
agccaaacaa aagttctgtt tgaccaccac agtgtaaaaa tcgattgtgg gacccatgca  49500
aaaaaaatca caatctcagc tgcctatgct ctcctcctgg acctgatagc cgtgcacaac  49560
aaatattttt ttaaactgga tgtgttcggc ttctctttaa agatcgtttt ttcctctgac  49620
acttaccaac cggctttcac agtgtggtca gttctttttt tttttacgca aagtttgatt  49680
ttagtcagac acgggaggat ctgttaagca ggcttggaaa tttcggaccc ctccaataca  49740
atattatttt agccaaaatt ttctaatttt ttaatttttc atgaattttg gtaatatttg  49800
ttctaattta actaaatttt gttcaaaatt tcggtctatc agtgacctcc gatcaaatca  49860
gttaaaccga gaaaataaac catgctctta agagagtttg gtatggttca atatcaaaac  49920
ttatagtctt gcaatttttt ctaccctttta tctttttccc tgactattta gtatggatcg  49980
tttaaaaaaa agaaagccca ttggtgacca agggcttgtt tgattcaaga ccatccctag  50040
ccttaccaac cttttggcaa tggcaaaaat tggttgttgc caaaaatatt ggcacaaatt  50100
ggctaagcct atgattggtt tctaccaaag ttgaattttg gcattcaatc aagccaaata  50160
atttggcaat aacattttct tatctatgga tataacatat ggcaaatatt ttggcattac  50220
cattttcttt ttgccaaaca tgttattcct tttgaatgac caatcttgac accttatgta  50280
tgttagtagt ggaatcgaca ctattctatc taaaacatct ctttacatag aggccgctaa  50340
taatttttct ttgagataac caaattttcc ttacaagtta agcaacaaag cccattggta  50400
agatatgcta cgacaaatga actaataact ccaaacataa agcggaggat cccgcatttc  50460
ccacgtgggt gactcgagcg gtgacaaacc ctagtacctc cacccccttg ggtgggttgt  50520
ggtggcactt tcggcaccgt attttccttg gacggatcat ttagaaagtc ctattattgc  50580
ctagtatgcc ttgacagttt aggcaacact cttggatggt ggtgtccttt gccctggtga  50640
tctagtagcc catggatgtt tagttatttg gacatggtgt tggatggtgc gctcgtgggc  50700
ctgttgtagg tctggtgcca accagtcatg cttagaaata gccggatagg tgcacagtgc  50760
tagttcttta cttggtggtt tgtgcagcgc tatcgacatg tggtggtgtg ctttttcttt  50820
gtccggataa taatctcata gggctatact cttgttattt tgctgctata ttattatgat  50880
aacttggtat ggttcgtttt ttcttttttt ggaaaaacac ctagttgatc aagggcttgt  50940
ttggttcaag tgcattccta atcttacctt ttcttttttt tttcaatggc aagaattgtt  51000
cattgcaaaa aaaaaagaga taaaaattgg ctaggcttac gttttggttc ttaccaaagt  51060
tgtactttga gaccaaatat atggcaaaat tttggcataa ccttttttttt tttgcttggt  51120
tgagcttggt acaaaccaat cagtcacaaa atagactgtc atgaatcacg cctactaaat  51180
tcctttgaac cgaactagaa tatatttgct cttaaaagat ttcttgattt caattggtac  51240
catttactag tagaaactta aatttaaatt ttaaaaacaa aatcataata ttgttgttat  51300
ggaaatttta gtcattttag taattttgta atatatgagt tgggttatac ttgagatatc  51360
ctaaattgct ttaagatgaa caattgctag gtatatcaaa gatgagctaa aaacaatgca  51420
ggcattcctt agagctgctg aagttatgaa aaagaaagat gaactattaa aggtttgggc  51480
agagcaaata cgtgacctgt cgtatgacat tgaagattcc cttgatgaat ttaaagtcca  51540
tattgaaagc caaaccctat ttcgtcagtt ggtgaaactt agagagcgcc accggatcgc  51600
tatccgtatc cacaacctca aatcaagagt tgaagaagtg agtagcagga acacacgcta  51660
caatttagtc gagcctattt cctccggcac agaggatgac atggattcct atgcagaaga  51720
```

```
cattcgcaat caatcagctc gaaatgtgga tgaagctgag cttgttgggt tttctgactc  51780
caagaaaagg ctgcttgaaa tgatcgatac caatgctaat gatggtccgg ccaaggtaat  51840
ctgtgttgtt gggatgggtg gtttaggcaa gacagctctt tcgaggaaga tctttgaaag  51900
cgaagaagac attaggaaga acttcccttg caatgcttgg attacagtgt cacaatcatt  51960
tcacaggatt gagctactta aagatatgat acgccaactt cttggtccca gttctctgga  52020
tcaactcttg catgaattgc aagggaaggt ggtggtgcaa gtacatcatc tttctgagta  52080
cctgatagaa gagctcaagg agaagaggta ctttgttgtt ctagatgatc tatggatttt  52140
acatgattgg aattggataa atgaaattgc atttcctaag aacaataaga agggcagtcg  52200
aatagtaata accactcgga atgttgatct agcggagaag tgtgccacag cctcactggt  52260
gtaccacctt gatttcttgc agatgaacga tgccatttca ttgctactga gaaaaacaaa  52320
taaaaatcat gaagacatgg aatcaaataa aaatatgcaa aagatggttg aacgaattgt  52380
aaataaatgt ggtcgtctac cattagcaat acttacaata ggagctgtgc ttgcaactaa  52440
acaggtgtca gaatgggaga aattctatga acaacttcct tcagaactag aaataaaccc  52500
aagcctggaa gctttgagga gaatggtgac cctaggttac aaccacctac catcccatct  52560
gaaaccatgc tttttgtatc taagtatctt tcctgaggat tttgaaatac aaaggaatcg  52620
tctagtaggt agatggatag cagaagggtt tgttagacca aaggttggga tgacgactaa  52680
ggatgtcgga gaaagttact ttaatgagct aatcaaccga agtatgattc aacgatcaag  52740
agtgggcaca gcaggaaaaa ttaagacttg tcgaatccat gatatcatcc gtgatatcac  52800
agtttcaatc tcgagacagg aaaattttgt attattacca atgggagatg gctctgattt  52860
agttcaggaa aacactcgcc acatagcatt ccatgggagt atgtcctgca aaacaggatt  52920
ggattggagc attattcgat cattagctat ttttggtgac agacccaaga gtctagcaca  52980
tgcagtttgt ccagatcaat tgaggatgtt acgggtcttg gatcttgaag atgtgacatt  53040
cttaatcact caaaaagatt tcgaccgtat tgcattgttg tgccacttga aatacttgag  53100
tattggatat tcgtcatcca tatattcact tcccagatcc attggtaaac tacagggcct  53160
acagactttg aacatgtcaa gcacatacat tgcagcacta ccaagtgaga tcagtaaact  53220
ccaatgtctg catactcttc gttgtataag agagcttgaa tttgacaact ttagtctaaa  53280
tcacccaatg aagtgcataa ctaacacaat atgcctgcct aaagtattca cacctttagt  53340
tagtcgcgat aatcgtgcaa aacaaattgc tgaatttcac atggccacca aaagtttctg  53400
gtctgaatca ttcggtgtga aggtacccaa aggaataggt aagttgcgag acttacaggt  53460
tctagagtat gtagatatca ggcggaccag tagtagagca atcaaagagc tggggcagtt  53520
aagcaagttg aggaaattag ctgtgataac aaaaggctcg acaaaggaaa aatgtaagat  53580
actttatgca gccattgaga agctctcttc cctccaatct ctctatatga atgctgcgtt  53640
attatcagat attgaaacac ttgagtgcct agattctatt tcatctcctc ctcccctact  53700
gaggacactc gggttgaatg gaagtcttga agagatgcct aactggattg agcagctcac  53760
tcacctgaag aagttcaact tatggagtag taaactaaag gaaggtaaaa acatgctgat  53820
acttggggca ctgcccaacc tcatgttcct ttctctttat cataattctt atcttgggga  53880
gaagctagta ttcaaaacgg gagcattccc aaatcttaga acacttgtga ttttcaattt  53940
ggatcagcta agagagatca gatttgagga cggcagctca ccccagttgg aaaagataga  54000
aatctcttgc tgcaggttgg aatcagggat tattggtatc attcaccttc caaggctcaa  54060
```

-continued

```
ggagatttca cttgaataca aaagtaaagt ggctaggctt ggtcagctga agggagaagt  54120
gaacacacac ccaaatcgcc ccgtgctgcg aatggacagt gaccgaaggg atcacgacct  54180
gggggctgaa gccgaaggat cttctataga agtgcaaaca gcagatcctg ttcctgatgc  54240
ccaaggatca gtcactgtag cagtggaagc aacggatccc cttcccgagc aggagggaga  54300
gagctcgcag tcgcaggtga tcacgttgac gacgaatgat aggtcagtca ctccctacat  54360
ggcagcttaa ttaacttgtt tctaattctc ttcttgttca gtattagcca tcaggtgagg  54420
gcgatgattt caactcactt ttcatctctc tcgttttctt aacctgacag cgaagagata  54480
ggcacagctc aagctggctg acgatctcct cccccatcag cgtcgtcatc agcgaacaga  54540
tagggcaggg cttccctgct tctgcgtgca cctcaccgct ctgactcgga gggacatgat  54600
gatcaatgag gcttccagtt tccaaatgcg tggctaacac accaggttgt ccctatccga  54660
ggtatgaatt gatgatccaa ttttttcct tccggtgagg ttcaaacatt tgatgcttag  54720
tttcatgagg gtattctgtg tttcgggttg tgatatgcat aattactccc agtttatggt  54780
ttgatgctga gtttttattt ctcttcttac acgtgcactc ttcatttcca tttcattcaa  54840
aacagaaacc aagttgattg cattgtggag gggaatatga gatcagaaat caaatggtta  54900
gttgtggttt tcttatttcg tttgctatgc gcagttgcgc accaaccgtt tgctagaatg  54960
tctgaaagag cctatgtaca tatggtggcc tgaacattac aagttatcat attttatatt  55020
gttgctagct ttcctttcaa aaaaaaaaaa attgttgcta accgatcaca tagtccagta  55080
gtccagtagt aagattttg ttaagtttat tgttactgaa tatattgttt ggcctgcagt  55140
tgttatttct ctcaaaacaa aattatttgg tagtctcaag tacaaaaaga aagacagatc  55200
agacaagttg ttttactcta ctagtttcaa attgatcatc tctgtttgtt cttcattcat  55260
tttctttctg taagagagtt tgctaggatg gtgatgtggt catgtggatg atcaaatgga  55320
ctacatcaga cgcatcacac tgctgcccaa cctttaccca ctgtagacaa atggagtgca  55380
ggtcctaaac caggccagaa gtttgttcag tgttcttgtt ccaaaataaa cattctggat  55440
ggcaggttat ttcattataa cattcactct tatagctttc ttagtcaaaa ctacaaataa  55500
ggtctcctaa aaaatgcatc gacgttgata tctgtgtttt ctgccatgca gaatgacttg  55560
ctctcaatgg ttgaagctgc aatcctccat gctcatttct ggctgaaccc aaattggtgg  55620
cttggaggct ggagctgcat gacattagag ataacaatgg ccactttttg ttgccatggg  55680
tgagggtaca tggatcatgc cgctgagcct ctactccgag caagcagaaa actggctggc  55740
tgtagatcga gttcgccatc gccctcaact ttgtcgatgc gatggtgatc atggatagat  55800
gtatgtcaca tagcgcaaag cggagcctcc aatgttcgca accgtactgt aaatgtggga  55860
gcggcgaatt tctcaagggg acaaccatgg aacagaggag atggagcaaa gtagttgctc  55920
ttgctatcat ttcagagctc aggctgatct ctagctcaga taggagtacg aattcttatg  55980
tgtgtgtatt tgatctatga tagtacgttt taagagttga gccagatatt gcttgatcat  56040
tacatgatga tatgtaaaaa atggtattga caaggagacg caggaacagg gtggttcatt  56100
gctctgttta atcttaatct tggagagcta ggatggaaaa ctgagttggt ggttatatct  56160
ctactacttt tgatgttgtc ccaaactaat ttgtttctac tcatgttcgt acctaaaaaa  56220
ggaatatttt agtgattaca gaacttaatt ttctctttaa tcagattatt tatcagtggg  56280
atttttcttt ctctagttct gtatgaaaat acttttttat cgtcaatcct cctaaaattt  56340
tgtgatatca gtattttttt tgttttactg gaatgggctg tttcagtgct gcttgcttgg  56400
acttgctgat tcctccctct ttcctattta taaactcatt tttcttcagt tttttttcct  56460
```

-continued

```
gtattttggt tttctttcct ctacgtgact acacattttg aatcgaacat gctatgctct  56520
gtatatctgc ttggaatact tattaaatgc ataggccggc catttggaat gagcacttaa  56580
cagttgtttg aacacttcca tggatttgtt tcctcagttg tcggacggct atttaaacct  56640
gattaagaat tccatgtgca gagacttgta ctagcgtcga agactttgct tcggtgactc  56700
ggagtcaagt caaggccggc acagcgcaag ccaataagct tcgacgacga cgacgacaac  56760
catgccgcgc tattgcttgt aaactttgtc tacaaaagcc agccgcgatg ccatccatcc  56820
actccttcct tccccattgt tgctcagcca ctcggcgtcg gattttcctc taccacacca  56880
gctctaccaa cctttcccga gattagagag gaagaggagg acgccgaagc cgttgcatca  56940
agcccaggac caccgtcgaa cacctgctgt gcgcaccgcc cggcattcct tcgcttcacc  57000
accgtgtgtg cacagttccc accatagtgt gcaaagcagc ataggtaagt caactccgat  57060
tttctgctgt tctttttttt ttaagataaa gcaggagttc tgctattcaa ttaagcatgg  57120
aagaattttt gggtattttg tgtatattct ggccttgttt agttctcaaa aatttttacc  57180
caaaaacatc atatcgaatc tttggacata tgcatagacc attaaatata gataaaaaaa  57240
ctaattacat aggaggtttt tttccggtcc ttgagggaag gcagtaccat atcctagccg  57300
ttgattttgc atgatctaac ggctggaaaa cctcggtacc gcgtggtacc gcgtttctgt  57360
gagagtaggt accgatcagt ttttgaggtg gaagggtatc attgtaattt cgcgtcactt  57420
atctcgatca acctaaccgt ggacgctgcc ccttcgagct cgtcgctgcg tggtgtatgc  57480
gacggcgggc gtggcgtgac ggcgatatgc gacggcggga tgcgacggca gatgcggcag  57540
tgaggaggcg gcggcctcga tgcggcggcg gccgcggcgc gatggcggga tgcgatggcg  57600
ggcgacccaa gccgagatga cgatgacaac aagcatgcga gattgatcga tgcggccgcg  57660
gtgcgatggt gggatgcgac ggcggcggcc gcagtgcgac ggcgggcgac ccaagctgag  57720
tgcgacggcg gccgcgtccc tcgtcggctc gcgggacgcg gcgggctcga gggggacggc  57780
ggtggtggct ggacgcgcgg cggcaggggc ggctggacgc ttgatggtgg cgggcggctg  57840
gatgcgggac ggcggcggct ggatgcgcga ctgcggtggc cagctggatg cacgatggcg  57900
gcggcggcct cgattggcga cgacgacggc gggctggatg ggcgacagtg gcggccggcg  57960
ggatgcacga cggcggcggc ggcgtcgatt ggcgacgacg acggtgggct ggatgggcga  58020
cggcagcggc cggcgggatg catgacggcg gcggcggcct cgattggcgt cgacggcgac  58080
gggctcgatg ccggcacgga tggcctcgat gccacatctg tttttgttag tccgatcata  58140
cccctactaa atcaatgggc agattagatt ggtacctcat ggtacctcct caaggatggg  58200
aaagatgctc ttgctatgaa gaacctccga gctcggtcaa tgtccggaaa ataacttgga  58260
taactacaag tggaagccat ttttggttgg ttttctgcat gatctgtttg tccctgtttt  58320
attatatcct gtaaactttt cattgcgcag tttgattaat acatgtctat ttgatattgc  58380
agataaatac agttgtagcc tgaaagatag tacttacaat ctattgcttg aaagtctaaa  58440
gaaagttgtt cagagaagga agatcagatg gcggatacag tactcagcat tgcaaagtcc  58500
ctggtgggaa gtgctgtaag caaggttgct tcggttgccg cagacaagat gatcatgctg  58560
ctgggagtgc agaaggagat atggtgagca tctgacttgc agcctaatta attttatttt  58620
cagttgcatt agatttattg ggaccacact tatgcagagt ggtatggtac tcagtttatt  58680
tttaatgatt tatttatatt tttataccat gttctggagg aatgcatatg cagtttttc  58740
tataagtata ttatttgcaa catcttgggg agataaatgt agaggaaagt gaaagtagaa  58800
```

-continued

```
tgcactggaa gtccctctat atacccaaac acaagtggac atagttttct cacggcaacc  58860
atgttcaatg aaggaataca aacgaggcag ctattaagga cctggtgata atctaatttc  58920
gacagaaaca tggtttcctt cgagtgtaaa caatgtagca tggcatgctt aagtcaaatg  58980
catatacaat ttgacaagga actattagtt tcagtgctgt gtaattttgc tttttgtagg  59040
atcgaacaga aataactaag ccaaccagag aggggggggg ggggggtgaa tagctgtagt  59100
accaaaaacc aaaactttta gcggaattaa aggttaccct tgaatcgata aattccgatc  59160
tgaccgaagt agatacgccg gtctgaccgc ttggatcccg tcggtctgac tggagtatat  59220
cgtccggtct aaccgcccga agaagctgaa gtcgccgctg gtctgaccgt gtcacgcccg  59280
gaaattcact agtaatttcc aaacttattt gtgcataaaa tcctcgtcca ggaatcagcc  59340
gaggtacaca aactgacaat ttaatataca atttaatata cagattcatc aaattaacta  59400
aaacgataag tacttactta agaggcactt agtcctcacc atgaagaaaa ctgcagcgga  59460
aaaataaaat ctagtgaagc tccggctcca ctcccacagg tagctcaact ggggtataag  59520
ccaaacgtct tctccttcgc aacttgtctt caactgaggt tgattggtta ttgcaaggtg  59580
agcatatgac atactcagca agccacacag caaatatgca agtgcacaag gataccaaag  59640
gatggcataa tataggctca tttgcgaaag cagcatttag caaagagtta agagtagtaa  59700
aacagtagag taattaatca gaaattttaa tcaacactga acagcacacc catgctgtac  59760
aggcccaacc atcctgaaca accatacccg gctgtacaga tctaactcca aaccaggagc  59820
taagcaaatt attaccaggt ataagatcca taattattgt gagaggtgtg agactaatca  59880
cgaaaaacat tgctcaaccc gcccataacc gcgggcacgg ctattcgaat agttttactc  59940
tggccagagg tgtaccactg tacccacaag acacagcccc acatcatgtc accatgtgcc  60000
tcagtaccac cacggtacct cggaaagggg ctgtgacatt acccctcgca taacacaacc  60060
caccacagtg cacctttcct ggatcataat caccccctca aaaaccagag gcatggactc  60120
cccagcgacc cccgtgggct tatctccgcc acttctcagt ctggtgctct gcaatgaacc  60180
atgctatacg aaaggtaaag ccgttgccca cgctggcttg tggttggcac gattaatgtt  60240
tcacaatagt agctcgtgaa ccggtcctta attgtcatga gcacgactct caaaaccatg  60300
tgctcacaac ccaccattat caagttttag ttggcaagta attaattaac caatcacgat  60360
tgaccatcgt gaactatcat taagccatca ttaaataata atgagtcata agttatccca  60420
atagtgtgct aatgtttcta agcatggcta agcaatcata tctaatatct agctgaacca  60480
atatatatag ctcaactagt caagttataa taacccaaga tatcaaggaa taaagtaatc  60540
aatgcaaaca ggtcataaca aaggaatagg ttcacaccac ccagtgacat tcgaaaataa  60600
atgcacagtt aaaataaata gagaatttaa atataggatc aacatgctca aaggattgtg  60660
tttgggatct gtgtgacttg ccttgcaata atcggtcttc aattaatctt cttgaacact  60720
tccgacgcac tcgcaaacct tcacaacgac ggaaacgaca agctaacacg caaaacaagg  60780
aaaaaactaa taaaaaccaa ataaacaata cataaaaagt aaacaaacat gtagatcata  60840
tttttagatg aattatgaga cttgaacggc ctcattctga cttcaaatga atttattatg  60900
aattttacaa gattaaatct atttaaagcc cttttaaaaa gaattaaata aatttaattc  60960
aatttatgga caattttaat atgtagatct ttattttata caaattttgc aacttgaacc  61020
acattaaact gagttaagat gaattagtta tgaattttta aagattaaat cggattaaaa  61080
cacttatatt gattttaatt gaattatgac gcaataatga attatttttg aaaaggaaaa  61140
ggaggattat tgcgtcagcg gctagggttt gcggtggacc gggtgcacgg cagcggttca  61200
```

-continued

```
cggaaacgaa cggccgagat caaccctatc caaaacggac ggccgagatc gatcggtcca  61260
cgaccggctc acgggagacg gggacgatga cgtcagcgat gacgtcacca ccggcggcgg  61320
cggctcggcg gctcggacgc gcacgctcgc cggcgaacgg cggcgcttcg gcacgaacgg  61380
agggcaccaa cgggtagagg gcgacgcggc gaactcaccg gtgaccaaag aagcggcgga  61440
gaagcaacgg acggcgacgg cgacgaggtt gaagcggcgg cggccttcgg gtcaacggcg  61500
gcgatggtgc tccggcgatc ttcggcgacg gcgaaggggc ggacgaggac ggcgacgcga  61560
cggcgaccac gatgacgacc ttcccgagcg acggcgacga ctggaacggc ggcggcgcac  61620
ggctggagcg acggcgacga cggcggcgct aggttacacg gcgctagagc gcttccgacg  61680
acgagagacg aaggcgaggg tggcggcggg tagaggagac accggggatc cttttaaagg  61740
ggttggaggg cgacggcgaa ggcccacggc ggccggcgac gagaaggaaa gatcggggat  61800
tcggaggaaa gagaggaatc cgattcgacc tcgaatccac aagtttccaa accgaattag  61860
gcgatgattc cataagagaa aaggaagagg agatcgagaa gatcatttcc cctctatcaa  61920
ttcggccgga gaaggaaagg atcgaccgaa ttttggaagg agacggcggc ggcgctcggc  61980
tagggtttcg ggcggcggcg accgaaggag gacgacgaaa ctgacagacg ggccccacct  62040
gtcagcgact gagagagaga agagagcggc ggcgcggact aggccgactt gggccgattg  62100
gccggggagg gagaaaagga aagagagagg ttttgggccg gctttcggcc caaagccaaa  62160
agagactttt aaaaaccttt ttcaatttaa attattcatg aaatgcaatt ccatttatta  62220
aaaatacttc cttagctcaa ataaatccca gaaaaatcta ggaattatag aattaagcaa  62280
agtatttaac aaaattttat ctagcccaat tttatgttga gatttagcaa attaaaatta  62340
gatcttctct tctaggcttt taaaatcatt tctactaatt ccttttaaac aacaatttat  62400
aatttaagga ttttttttaaa caagaaaagc acttaacaaa tataattaga tcatcaatga  62460
tcaaataatt actgaactgt tctttgtatt atttaagaat tgagctctga aaaatccgag  62520
aaaatttcag agagtataat taaccatgga gaatttaaca aaaattaaat ccatccatgc  62580
tttatattta ggaaatttta tttcccacat ttaacttcac ttgtaaatta atgaacattt  62640
aatataaatt ctaataataa tttattaatc ctgaaacgaa aatcaggatg tgacagaccg  62700
ccgtgtaccc gctggtctga ccgccgcgat gtcgctggtt tgaccgccag tgtcccaccg  62760
gttagaccgc cgaactcaag taaatacaaa ttgaagatct ctcaaagtgg atgacaactt  62820
tattgcttct ctctatgttt acaaagtgca acaacagcac tcctcacgaa aatctcgact  62880
aaactcgaaa ccctaactat tctctcaact caatactctc taaagcgata ccgggaggcc  62940
acaccctccc tctctattta tacatagggt aggcagccta aagccacaaa tcaaactcat  63000
gcaagaagtc ctaatccaca taggaaaact tcccgtacaa gaaaccaact ttacaaactc  63060
aaatcatacc aaatttagac tccttccaaa tttgactcca catcctatac gcacacaata  63120
tttccattgt atgccatatg taatcttcac caaccacgtg catttatttt tagcctaagt  63180
atcccgcatg atatctgacg gtccggacgt caccttatct ccaagttgac tcccgatcca  63240
tcgccgataa tactctcccg aggcatcaaa acacctacac atgaatcaaa caaagaaacc  63300
atattccaag accaagctat atccaacttg actcattatt agcaaacaac agtattacat  63360
acgcatagta tccatctaga agttataagc atgaaacatc cacagatata aaaaaaacaa  63420
cccgaaaccg aaaccaacac agagttggcc gatcagaccg cgggctggcc ggtctgacca  63480
ctcacataac tctggtctga ccggcaaccc atgcccggtc tgaccggacc aaaactctag  63540
```

-continued

```
tagcacatgt tcatcacctg caaatccaat catctccaaa atcacttcac caataatctc  63600
ctattatcaa aaccaataat ctcagatgcc aattgttcat catagaataa gaatgaaaca  63660
cactttgatt tacacttttc accttggaat caaagattta atgcaaatta agcttcacgt  63720
tcctagtttg agcttccaat ttgtacatat ttgtgattta taatgctata tatacatgta  63780
tacagacaag taacgcagtc cacgtgggat gttggccatg cctggataag ctgagcaaga  63840
tttagacctg tgtcaaaaca atgtcttgaa ttccgttgaa ctttttgttt acaggttcat  63900
caaagatgag ctacaaacga tacaagcatt tttgattgct gccgaagcat caaagaaaag  63960
catactattg aaggtttggg tgcagcaagt aagggatctt tcctatgaca tcgaagattg  64020
ccttgatgaa tttacagttc atgtgggcag ccaaaacttg tcgaggcagt tgatgaagct  64080
aaaggatcgc catcggattg ccatccagat ccgcaatctc aggacaagaa ttgaagaagt  64140
aagcactagg aacatacgct acaacttaat agagaatgac ctcacctgca ccactgatga  64200
gaggaattta tttatggaag acattcgcaa tcaatcagct aacaacatcg aggaagctga  64260
tcttgtgggt tttctggac ccaaaagaga gttgcttgat cttatagatg tccatgccaa  64320
ggacggacct acaaaggttg tatgtgttgt cggtatgggt ggtttgggta agactactat  64380
tgcaaggaaa atttatgaaa gcaaagagga cattgcaaag aatttttctt gctgtgcttg  64440
gattactgtt tcacagtcct ttgttagggt ggaactactc aaggatttga tggtgaaact  64500
ttttggagag gaagtactga agaagcggcc gagagaactc gaagggaagg ttccacaagt  64560
agatgacctt gccagctacc tcaggacaga gttacatgaa aggaggtact ttgttgtgct  64620
tgatgacgtg tggagtacag attcatggaa atggattaat agtattgcct tccctagaaa  64680
taacaaaaaa gggagccggg tgatagtaac aacaagagat gttggcttag ctaagaagtg  64740
tacttctgaa ttgcttatct accagcttaa accccctagaa ataaactatg caaaagagtt  64800
gcttctacgg aaagcaaatg aagcaatagg agatatggaa agtgataaaa agatgagtga  64860
cattataact aaaatagtaa agaagtgtgg gtatttaccg ctggctatac tcacaatagg  64920
aggcgtgctt tccaccaaag agataagaga gtgggaaact ttttatagtc agataccttc  64980
agagcttgag agcaacccaa accttgaagc aatgagaagg atagtgaccc taagttacaa  65040
ctacttaccg tctcatctta agcaatgctt tttgtatcta agcatatttc ctgaggattt  65100
tgaaattaat aggaaccgtc tggtaaatag atggattgca gaggggttta ttaaagctag  65160
gactaatatg actattgaag atgttgggaa aagttacttt aaagaactta tcaaccgtag  65220
catgattcag tcatcaagag cgggtatacg aggagatttt aagagctgtc gagtccatga  65280
catcatgcgt gatattacaa tttcgatttc tagagaagaa aatttcacac tcttacccga  65340
tggcactgac tatgatgtag tacatgggaa cactcggcac atagcatttc acgggagtag  65400
gtattgctct gaaacaagct tggactggag cattatacgg tcattaacta tgtttggtga  65460
gaggtccgta gaactagagc attcagtttg ttcatctcag ttgaggatgt tacgggtctt  65520
ggatctaata gatgcacaat tttctatcac acaaaatgat gtcgacaaca tagtgctctt  65580
gtgccacttg aaatacctac gcattgcaag atacagatac cgttcaccat atatttattc  65640
acttccacaa tccatagcta gactgcatgg tctgcagaca ttggacttgg gtcagacgta  65700
catttcaaca ctgccaactc agattactaa cttcggagtc tccgtagcct tcgatgcatg  65760
aaagaatatt tttcttcttc tttaagaaca tatttaacta acacattatg cctgcccatg  65820
atattcacac ctttcgttag tacctcggat cgttctgaaa caattgctaa attgcacatg  65880
gccaccaaag gcttccgttc aaaatcaaat ggtgtcaagg taccaaaagg aatatgtaag  65940
```

-continued

```
ttgagagact tacaagagga ttgctacggt ccagcaggtt gtaccgggcg gtactggtac  66000
cgcgcggtac caaaacccat ctaaccgttg aatccgggat gggtaggatc gggagagaaa  66060
agatgagcaa gggtggatga gggagtacct gtttcgagtc gtcgttcccg gcggcggcgg  66120
cgtggagtac ctgtttcgag tcgtcgtcgt tcccggtggc ggcgcagagc aacaagggac  66180
gccggcggcg cgggagagga taaagtccgg cggcagcgcg agagagaaaa aagggaacgg  66240
cgacggtgcg ggagaggaac aagggaagga cggcggcggc ggaagaggaa caagtccgac  66300
ggcgaggaag aggaacacgg cggcggcgaa aatcatccag cgtagctagg gttcgagccg  66360
cccgatccaa acccatctat tgcacgcgaa gttactcttt tacccttcca actctcttct  66420
ccatgcggta tcacctaagg gacatttttg gtaccgtgcg gtaccacgca acatcagccg  66480
ttggatcagg ccagatccaa cggccagcat ttggtaccgc tcggtacgtt ggacagtaaa  66540
aaaactcgac ttacaaatat tggaggtagt ggatattaga aggactagca gtagagcaat  66600
caaagagttg gggcagttaa gcaagctgag gaaattatgt gtggtaacaa agggatccac  66660
aaaggaaaaa tgtgagatac tctatacagc tatccagaag ctctgtttcc tacaatctct  66720
ccatgtgaat gctgtgggat tttcaggtat tggaacactt cagtgtatag attctatttc  66780
atctcctcct cccctactga ggacactcag gttgaatgga agtcttgagg agatgcctaa  66840
ctggattgag cagctcacgc acctgatgaa gttcaactta tggaggagca aactaaaaga  66900
aggtaaaacc atgttggtac ttgcggcgtt gcccaacctc atggtccttt atcttcattc  66960
caatgcttac catggggaga agctagtatt caaaatggga gcattcccaa atcttagaac  67020
attttcgatt tacaatttgg agcagctaag agagattaga tttgaggacg gcagctcaat  67080
cttgttggaa aagatagaaa tattcagggg ttggaatcag ggattgttgg tatcattcac  67140
cttccaaggc tcaaggagat ttcacttgga tacggaagta aagtggctag gcttggtcag  67200
ctggagggag aagtgcgcac acacccaaat caccccgtga tgcgaatgag ggaggaccga  67260
agtgatcacg accttgcttg tgacgccgaa ggatcccctg ttgaagtgga agcaacagat  67320
cctgtgagag ctcgcagttg caggtgatca cgttgacaac gaacgacagg tcagtcactc  67380
cctacacggc atcttaatga acttgtttta tcctcttgtg agatcgatga ttttaactca  67440
ccctttcatc tctctcgttt tcttaaccta acagcgaaga gataagcaca acttaagctg  67500
gtttgatcaa gtgatgatct cctcctccat tggcatctcc ggtcgtccct gcttctgcgg  67560
ctgcgcacct cgctgctctg aggaggggtg ctgatctaag gaggcttcca ctttcttcaa  67620
ttgcgtctca tgctctcgat tcttccctct cgggtatgaa ttgttcaatc tgatattttc  67680
tcgcgatctg ctactggttc cagcatgagc atttgaacca gcagcttaga attatcgttt  67740
gatcaggtgt tatttatccc ttcttacctg ggaactctac ttatccattt cattcagaac  67800
agaaaccatg tttattacac tatagagggg aacaacagat caggcacgag ttgtggtttt  67860
gttatttcct ttttggtgtg cacaccaggt gattgctaga atgtctgaaa gagcttgtgt  67920
gcatggttgg ctcaacatta tgtgctaatc actcttttat accgttgctg acctatcaca  67980
tagtgcagga gtaaaatttt gctatgttta ttgttactta atgttgattt tccttttcgt  68040
aaagaatatt agctttttag ataacaaaaa gaatattatg tatcctgcaa aaaggtttga  68100
tttggtgatc actggctagt acaaaagtaa cgagagatca gaaaaaacaa agttttggtt  68160
acactagctc attacaattt atttgctgaa catgtgaaaa attaataatt gtcgtacgtc  68220
atggttctct ggaagtctgg ctgcaggtgg ttagttttgt catatccatt atcttggtct  68280
```

-continued

```
accttttcct actaaactag gactatgagt agaaaaaagt aattgttggt tccaagttca  68340
aaagataggc agatgtgagc taaggaactt gcatttcttg atctccttca gagcttctca  68400
cctcacataa atggatctct gtttatccca aagcaacatt ttttaacctg ctagttccaa  68460
attgatcatc tttgttattc ttcatttatt ctatttctct ccctaaggga gttttctagg  68520
gtggatatgt ggaaaatcga atgcagctat gctgttcaaa ccactgtcaa aagatgcagg  68580
acaggatggg cagatgttta ttcagtgttc ttgttcaaat gaaacatatg ctattctgga  68640
agaggttggt taacttacat tgtatataac ccttaccttg ttactatcct cttgcaaaat  68700
gcatggattg gtgaaatcat gttttttgtc atgcagaatt gttttctgaa gctcaaagtt  68760
gaagctgcag tcttcactgt ttctggcaga acccaaattg gtggcttggt gctgcataac  68820
ctgcagagaa cgcaacggcc actgcttgta gccttcaagg atgctacatt attgatcatc  68880
tcactacggt cccgatcaaa cttctgatcg agttcgccac cactgtggac tttgcatatg  68940
ttgatggagt ggtgcgtatg aatccagggg gcagagccac tgccctgcga ccttggggct  69000
tgtcaacgag catacagtat aatattttgc tgttatttca gtgattaaaa acgaaaattt  69060
taaagcaaac attgaatgca attagatctg cccaggttct caaaatttct ttagctccgc  69120
cactgcttga atcgatgtca tatgctgcaa attaagtgga ttggagatgt gcatatgctc  69180
gaatgttctc ggttatattg taattgtggg gtagcaactt tatcttgggt acaaccatgg  69240
aacaagggtg aaattgtact aattcttatt tgtgtacaat tgatatatct cattacttct  69300
tgcattctgt tagtcatatg tatttccata catcgtttgc acctgctatg gctgcttgag  69360
gatatggcaa agcttaaaag atgatgttaa catggtcaca tggagatgca gggcactcca  69420
ttttctgttt ttctctcaat cttatgtaga gttaatatat ggacagtagc aatagttaca  69480
tctttctgtc aactaggcat actacccacg tgttgctccg ggtctttttg ggatggtctc  69540
tattaagatg taaacttatt tattaaatga attcaatcgc gtcgcattgg ttcatttatt  69600
tagacttggt tgtgatatac tcctgttgta aaatataata acttttacga ttctagcacc  69660
atttataata tttataagag tacctgtctc agcaatcatc aatcattttc tatttagttc  69720
tttctatctt acccttacat acctttcaac actcatccat tcctctggtg aataactaaa  69780
aatgtttaaa tttcagagcg gaggtagcaa taagttctag taaaagctgt tgaatagtcc  69840
cacattggtt gtaaaaggac aaatgaccta acatataagt gggtgagccc tgtacctcat  69900
tagctagctt tttgggtgag gtccctttac gatcttataa ttggtattag agcctggcta  69960
gtttgacatt tacccgaggg cactactaga aaaaggaccg accgccgcta gaccaacaaa  70020
ggaacataga cgagatcgcc ccaaaaaaag cccccacaac caacacaaag cccaactcct  70080
aaagcgtgct tgcaccaatc gttcgagaga tttcggctag gggatgccaa aatgacgtct  70140
tcgagaaaag aagcgatgga aaaccgccgc cgccgtctgt cggggctcaa aggagccaag  70200
actgggcttt cgcccggcaa ccacccttga gggataagac atcacgacaa cgccctcgac  70260
atcacgacaa cgccctcagg aagtcaggag ggggaattaa ccatcgttgt cggtccggcc  70320
aaggccgggc tgggttttca cctgctgctc accacctgcg aatccacggc tgacgcaccg  70380
atgctccacc accactcaac ctctgccgcc aagtgggacc actgcaccgg cgccccctgt  70440
cagccaacct tcatgcgccg aagaccgtgc cacacccacc gacagctcct cctcgcactg  70500
agactgcctc ctccactacc gcccaagcct ctcgcgccaa gccggccttc tctactggac  70560
gcgcctctcg cgccaatcca accttcctcc atcggccgcg cctctcgcgc caagccggcc  70620
tccatctcct ccgcccgcgc ctctcgcgcc gagccagcct ccgctgccag cagttgcgcc  70680
```

-continued

```
tccctgcacc aagccggctt tcgacccctc ctccaaaggc taccgcaccg accggatacg 70740
gccgtctgcc acgcccccgg ctagccgtcc gagaccgcca tgcctccccc tatggcggtg 70800
gcgatcgcca ccaactaggg ttgaaagtga ttcggataat ttccgtccga ccggaccttt 70860
tttcggattc ggatagtgtc ggtcggatat attcggaaat ttgaatttga aatcatgaca 70920
acttcaaata gcatttttaa atactaaatg atttcaactg aaaaagtcat caacaacaaa 70980
gttgtataac tcatcaagat ttataacttt tattttggtc atttcttcat ccgacaaagt 71040
gatagtaata ttgttcacaa aatttacatc tctcattagg ttttatgaac tataagagag 71100
atatataaat tttatgaaca atgttactat tactttgtag aacataaaag ttgtagaact 71160
catcaagaaa tacaactttt attttggtca tttttctaaa agtttgaatt tgaatttgaa 71220
aatatgacaa cttcaaataa tattttcaaa tacttaatga tttcaactga aaagtcatca 71280
acaacaaagt tgtatattat caagatctat aacttttatt ttagtcattt tcttcgtaag 71340
acaaattgac actaacattg ttcacaaaat ttacatctct tatttggttt tatgaactat 71400
aagagagata tataaatttt gtgaacaata ttactatcac tttatcagat gaagaaatga 71460
ccaaaataaa agttgtattc cttgatgagt tctacaactt ttatgttcat gactttttca 71520
gctgaaatta tttactgctt caaaatatca tttgaagttt tgaaattcaa ctttttaatt 71580
gataaaacaa agtcacaaga aaaaatggcc aaaataatag cagtaaaaac acaataacat 71640
gatagagcat gattttagaa acatttagga aaaagaatca tccaatttgg agttcatatg 71700
agtgagataa actagtttca aatttttaaa ttttattttc gcatacggct ccttaagacg 71760
tccgtatgga aaaaatgatt tttccacgcg ggctattaag ttgtccgcac gcaaaatgag 71820
ctcattttgg cgtcttgagg agtcgtatgc gaaaatgccg acgcggcaag ttgtgatccg 71880
tttggaaaaa tcatagggtc tcgtacaaaa gaaattgttt gtgtagtagc gaggggtttt 71940
tatattccga ttaatattca tcaccgtatt cgtttcgctc cgtatttgta ttcgataata 72000
ttccatttcg tttttatatc cgggtttcca gttccgaaaa aaaagaaagt gaatacgata 72060
gagctagttt ccgaccatat tcgatccgtt ttcatcccta ccaccaccgc agccgctact 72120
gcccttccat ccccgccgcc atcttgccat cctcccgcac cttctcgcag tcatcgagct 72180
ccgacggcac acggcgcaga cggcccaccg tggtagccca caccgccgtc gccacgaact 72240
cctcgccacc accgcctcga ccgccagact ccttcgggcg ctgggtctgc cgtcggcgcg 72300
gctaggttcg cctcaccgac gccatcccct cgccaccccc accgccagac gctgccgaag 72360
gctgccatcc cctccccttg cctcccctgc cgccatcgcc atccccgcca ccagacgccg 72420
ccgccggcca ccatcccgcc agatccaggt gcggatctag cggtttcctc cgtcgccgta 72480
aacgcctcga acgccgctgc caccaccacc agacaccacc gccgcaccgc tcagccccgc 72540
tgccagctgc cccatcgcca gatccggccg ggcggcacag atctgggctg ttctgctgcc 72600
ccgagcaggc ccccctccta tgcccgagca ctaggatgaa gccccgccgc cactgtcttt 72660
gtggccgcgc gactttgccg gcgactgctt gggcagcgac gaggcagagg agggaaaggg 72720
agatgagcac cggcgaggtc gtcgcctccc agttgcccgt ggggaggggc gacacgagag 72780
gccaagcgct actcaactgc ctgatgctca tccaaagtga gaaagatgct tgaagctgtc 72840
gctcgaagca actttcagtc ctcgatataa ttcgatataa gtgatttctc tctccatatt 72900
tgtttggaga aatgctagtt ataagaaact aagtgtgacc atgtgttata gatgtcagag 72960
aaaacagttc attttctcaa ttctcaaggt aattgggaaa atggagaatt actgagcgat 73020
```

-continued

```
acgtgttgct ggaaaattga gaatcactga tgatcgcctc catctgaaaa ttaccgagcg  73080
atatttattg ctgccaaatc aaaatgattc tattcaaccc gtgccatggc atggccggat  73140
ggccccagtt cactgattga tcacttaata tatggactga acaataaatc atggtacttt  73200
ggttgtcgag catgatcatt atttgtggac cacagattca ccgaattaat tgggatattg  73260
aatcggtcac acacacgacg ggcgtactcc gctcgtctta aaataaatgg attggacgtg  73320
acattatcta ctacaacgaa tctggattag atagtgtctc atccaatcct aaattggttt  73380
attttgtgac ggagggagta tgatgttaac gtagatggaa atgaggaatt gagtagacag  73440
tgtggggctg gaaaataatg gaggacagta acatcttgga gtgtagtgag gcctggaggg  73500
tcgtccttga catccaaacc gcacctaact ctatgataag catcctctct cagattgttc  73560
agtgcaaaag ctaccaatac tgctccgaga gccagaaaaa agcgctggtc gcctagtgct  73620
atcttctatg cagtcgtgag attggttgct ctaagcttga agggagagtc gaacgagtcc  73680
atggcggaga cggtgctgag catggcgagg tcgctggtgg gcagcgccat cagcaaggcc  73740
gcctccgctg ctgccgacga gaccagcctc ctgctgggcg tcgagaaaga catctggtac  73800
gtactgcgtg actctcgtta atttattctg tagatgctca ggaatcagca actattgtgt  73860
tgatttccat cgtagcatat cgattttgtt ggccaccaat tctaatcggc cggaacaagc  73920
tagtcactaa atctggcaaa tcgatcagct gctgagtgca caaacatgca tgttattctt  73980
tttttttttg ggttatatgt taagcaacaa agccccttgg taagatatgc atggcaaatg  74040
aactaatatc gacatacgta aagcggagga cccctcgttc catgcgtggg tgactcgagc  74100
ggtgacaaat cctagcacct ccacctcctt ggatggcctg tggtgacgct ttcggccccg  74160
agtttccctt gaatacatca tctacaaggt gctattaatg tctagtcaca tcatttacga  74220
ggtgctatta ttgcctagtc tgcccgaaga tagtttagac aacactcttg gatggcggtg  74280
tccttcgccc agtgatgtcc aagagcccgt ggatgtttag ttgtttagac atggtgttgg  74340
gtggtgcact agtgggcctg atgggccagt tgtaggtcca gtggtaacca atcatgctta  74400
gcaatagccg gatgcccgga ttggtgcttg ttcttttttc ggtgtcgacg catggtagta  74460
tttactttc ctgtttttcc tgattatagc atcctaggct atactcttct aatttattca  74520
tgctatatta atattaaaac ttggtatggt ttgtttcatt caagaccctt ggtggtcaaa  74580
ggcttgtttg gttcaagttc attcctagcc ttaccaactt tttggcaata gcaagaaatg  74640
gtcattgaaa aaaaaaggca aaaattggct aggcctacag tttatttcct agcaaagtta  74700
tactttagca ttccactaag ccaaataatt cggcaatgcc attttcttat ctacatgcca  74760
aatatatggc taatattttg gcattaatta ctcttatttt ttttggcaaa attgatcaaa  74820
agttcacatt tttagctcta tagtattaaa agttatctat tcactttaat agaccgaaag  74880
tttactcggt tccgttttta gcactaccgt ctcttttctc ttgatttgcc gtcaattttg  74940
accggcagtc ctaccccccag gagacattga gcagcagccc gtgatccccc tctctcgccg  75000
ccggtgacgc tgtggtggca tcgttcctgc tgcgggcaga ataagtctgg cgtcatcgcc  75060
ctatcgcctg gagctgcaac caccactacc gggcccatcg atcgtctaga gcgttatcca  75120
ccctgcctgc cccattactt gcagctccgg ctgggtcaga acctctccat gcctgataaa  75180
ttggttcaag attgtcgctg tccggccagc gcttgaattt tcagaatatg ccatcgaata  75240
cgcgctgctt ttaagatatg ctacccgatt catgctattt ttagaatacg ccatcagaac  75300
acgaattttc ttcgttccgt gccactccgt ctctcggagt cagtcgtgcc gtcgtcatcc  75360
gtccgcccag cactgtcgtc gtcagtccgc cacccgtgcc tgactgtccg ttcagctgcg  75420
```

```
ccgtcgtccg tccgtcgccg ccatcgccgt cgtccactgt cgcgcccgca cctgcacccg  75480
tgtcaggcgc gccgtcgtcc gtccgctgtc accatcatcg tcgtccactg cggcgagcgc  75540
agacggctgt ggacggatga ttgcgcggca agcgcaagcg gcggtggacg gacgacgggg  75600
cagtgcacgc gagcacggta gccgatggac tgacgttggc ggcattggga gatggacgac  75660
gacggcatga ttgacgtggg gaacggaatg tcacggaacg gagaaaattc gcactccggt  75720
ggcatatatt ccgaaaatag cacgaattgg gtggcatatc ttaaaaacag tgcctatttg  75780
gtggcatatt ctaaaaattc tcggtcagca taatccccat caatccccaa tccctcaaca  75840
gttgggttaa tattcctgga gatgtgttcg gttgtttagg ttgaagttct ccacttcacc  75900
tccatgagta catgcacctc tacacgtacg ttcttaatgt gtttgtttgt tctatcctcc  75960
gcttgggttc tattttgttg gttccgatct gatttgatct ggagcggggt cgatcttcca  76020
cgacggcgag agagacgttg ttcgggctgc tcgattaggt tcaactgttt aggtcgaagg  76080
gaggggtaga attgcaattc aagtgcatgg tcagtcaatt tgggtcaaaa ttaacatcaa  76140
actgggataa agagacgaca gtgccaaaat tggtaacggg aaaactttga gttctattaa  76200
agtgaaccag taactttcgt tgctatagaa taaaaacgta aacttttaat gctccttggt  76260
tgagcttggt acaaaccaaa cagacgtaaa ataaacacta tcctgaatca agtctactaa  76320
gttccattga actcaaccag gatacgtaca cttcctctta gaagatgtct tgttttcact  76380
ttgtacaatt ttttctattg taaatttggt acctcgttgt acctaggtac aagaggtacc  76440
atgagatacc aaattttaca ctaaaatttt ggtacctcat ggtacctcct caacgaccgt  76500
agaattgctc ttaatttaat ttaaaaaaaa cataatattt ttaaagcata ttatggaaat  76560
tttagtaatt attacttttg taatatatga gttacggtta tactcgagat atcctaaatt  76620
gcttggagat gaataattac aaggtatatc aaagatgagt tgaaaataat gcaggcattc  76680
cttagagctg cagaagttat gaaaaagaaa gacgaactat taaaggtttg ggcagagcaa  76740
atacgtgacc tgtcatatca cattgaagat tcccttgatg aatttaaggt ccatgttgaa  76800
agtcaaaccc tatttcgtca gttggtgaaa cttagatagc gtcaccggat cgctagcccg  76860
tggatgttta gttgtttgca catggtgctg gatggtgcgc tcatggtctt gttgtaggtc  76920
tggtaccaac cagtcatgct tagaaatagc cggatcagtg cacggtgcta ggactttact  76980
tggtggtctg tgcagcgcta tcgacatgtg gtggtgtgct tttttttttt ccggattaca  77040
atctcatagg gctacactct agttattttg ctgctatatt aatatgaaaa cttggtatgg  77100
ttcgtttctt ttagaaaaaa acctagttga tcaagggcta gttttcttca agtgcattcc  77160
taatcttagc ttcttttttt tttgcaatgg caagaattgt tcattaaaaa aattgataaa  77220
aattggctag gcctacgttt tgtttcttac caaagttgta ctttaacaat aaactaaggc  77280
aaatatttcg gcaatgccat tttcttgtct acagaccaaa tatatggcta aattttggca  77340
taaccatttt tttgtttgct tggttgagct tggtacaaac caaacagacc caaaataaac  77400
agtgtcatga atcacgtcta ctaaattcct ttgaactgaa ctagaatata gttgctctta  77460
aaagatttct tgatttcact cggtaccatt tactagtaca aacttagatt taatttttaa  77520
aaataaaatc ataatattgt tattatggaa aatttagtca tagtactttt gtaatatatg  77580
agatgggtta tacttgagat atcctaaatt gctttaagat gaataattgc taggtatatc  77640
aaagatgagc taaaaacgat gcaagcattc cttagagctg ctgaacttat gaaaaagaaa  77700
gatgaactat taaaggtttg ggcagagcaa atacgtgacc tgtcatatga cattgaagat  77760
```

-continued

```
tcccttgatg aatttaaggt ccatattgaa agccaaaccc tatttcgtca gttggtgaaa  77820
ctcagagaac gccaccgaat tgctatccgt atccacaacc ttaaatcaag agttgaagaa  77880
gtgagtagca ggaacacacg ctacagttta gtcaagccta tttcctctgg cacagagatt  77940
gacatggatt cctatgcaga agacattcgt aatcagtcag ctcgcaatgt ggatgaagct  78000
gagcttgttg ggtttctga ctccaagaaa aggctgcttg aaatgatcga taccaatgct  78060
aatgatggtc cggccaaggt aatctgtgtt gttgggatgg gtggtttagg caagacagct  78120
ctttcgagga agatctttga aagcgaagaa gacattagga agaacttccc ttgcaatgct  78180
tggattacag tgtcacaatc atttcacagg attgagctac ttaaagatat gatacgccaa  78240
cttcttggcc ccagttctct ggatcaactc ttgcaagaat tgcaagggaa ggtggtggtg  78300
caagtacatc atctttctga gtacctgata gaagagctca aggagaagag gtactttgtt  78360
gttctagatg atctatggat tttacatgat tggaattgga taaatgaaat tgcatttcct  78420
aagaacaata agaagggcag tcgaatagta ataaccactc ggaatgttga tcttgcggag  78480
aagtgtgcca cagcctcact ggtgtaccac cttgatttct tgcagatgaa cgatgccata  78540
acattgctac tgagaaaaac aaataaaaat catgaagaca tggaatcaaa taaaaatatg  78600
caaaagatgg ttgaacgaat tgtaaataaa tgtggtcgtc taccattagc aatacttaca  78660
ataggagctg tgcttgcaac taaacaggtg tcagaatggg agaaattcta tgaacacctt  78720
ccttcagaac tagaaataaa cccaagcctg gaagctttga ggagaatggt gaccctaggt  78780
tacaaccacc taccatccca tttgaaacca tgctttttgt atctaagtat ctttcctgag  78840
gattttgaaa tcaaaaggaa tcgtctagta ggtagatgga tagcagaagg gtttgttaga  78900
ccaaaggttg ggatgacgac taaggatgtc ggagaaagtt actttaatga gctaatcaac  78960
cgaagtatga ttcaacgatc aagagtgggc atagcaggaa aaattaagac ttgtcgaatt  79020
catgatatca tccgtgatat cacagtttca atctcgagac aggaaaattt tgtattatta  79080
ccaatgggag atggctctga tttagttcag gaaaacactc gccacatagc attccatggg  79140
agtatgtcct gcaaaactgg attggattgg agcattattc gatcattagc tatttttggt  79200
gacagaccca agagtctagc acatgcagtt tgtccagatc aattgaggat gttacgggtc  79260
ttggatcttg aagatgtgac attcttaatc actcaaaaag atttcgaccg tattgcattg  79320
ttgtgccact tgaaatactt gagtattgga tattcgtcat ccatatattc acttcccaga  79380
tccattggta aactacaggg cctacaaact ttgaacatgc cgagcacata cattgcagca  79440
ctaccaagtg agatcagtaa actccaatgt ctgcatactc ttcgttgtat aggacagttt  79500
cattatgaca actttagtct aaaccaccca atgaagtgca taactaacac aatatgcctg  79560
cctaaagtat tcacaccttt agttagtcgc gatgatcgtg caaaacaaat tgctgaattg  79620
cacatggcca ccaaaagttg ctggtctgaa tcaatcggtg tgaaggtacc caaaggaata  79680
ggtaagttgc gagacttgca ggttctagag tatgtagata tcaggcggac cagtagtaga  79740
gcaatcaaag agctggggca gttaagcaag ctgaggaaat taggtgtgac aacaaacggg  79800
tcgacaaagg aaaaatgtaa gatactttat gcagccattg agaagctctc ttccctccaa  79860
tctctccatg tggatgctgc aggaatctca gatggtggaa cacttgagtg cctagattct  79920
atttcatctc ctcctcccct actgaggaca ctcgtgttgg atggaattct tgaggagatg  79980
cctaactgga ttgagcagct cactcacctg aagaagatct acttattgag gagcaaacta  80040
aaggaaggta aaaccatgct gatacttggg gcactgccca acctcatggt ccttcatctt  80100
tatcggaatg cttaccttgg ggagaagcta gtattcaaaa caggagcatt cccaaatctt  80160
```

-continued

```
agaacacttt ggatttatga attggatcag ctaagagaga tcagatttga ggacggcagc  80220
tcacccctgt tggaaaagat agaaataggc gagtgcaggt tggaatctgg gattactggt  80280
atcattcacc ttccaaagct caaggagatt ccaattagat acggaagtaa agtggctggg  80340
cttggtcagc tggagggaga agtgaacgca cacccaaatc gccccgtgct gctaatgtac  80400
agtgaccgaa ggtatcacga cctgggggct gaagccgaag gatcttctat agaagtgcaa  80460
acagcagatc ctgttcctga tgccgaagga tcagtcactg tagcagtgga agcaacggat  80520
ccccttcccg agcaggaggg agagagctcg cagtcgcagg tgatcacgtt gacgacgaat  80580
gataggtcag tcactcccta catggcagct taattaactt gtttctaatt ctcttcttgt  80640
tcagtattag ccatcaggtg agggcgatga tttcaactca cttttcatct ctctcgtttt  80700
cttaacctga cagcgaagag ataggcacag ctcaagctgg ctgacgatct cctcccccat  80760
cagcgtcgtc atcagcgaac agaaagggca gagcttccct gcttctgcgt gcacctcacc  80820
gctctgactc ggagggacat gatgatcaat gaggcttcca gtttccaaat gtgtggctaa  80880
cacaccaggt tgtccctatc cgaggtatga attgatgatc caatttttt ccttccggtg  80940
aggttcaaac atttgatgct tagtttcatg agggtattct gtgtttcggg ttgtgatatg  81000
cacaattact cccagtttat gctttgatgc tgagttttta tttctcttct tacacgtgca  81060
ctcttcattt ccatttcatt caaaacagaa accaagttga ttgcattgtg gaggggaata  81120
tgagatcaga aatcaaatgg ttagttgtgg ttttcttatt tcgtttgcta tgcgcagttg  81180
cgcaccaacc gtttgctaga atgtctgaaa gagcctatgt acatatggtg gcctgaacat  81240
tacaagttat catattttat attgttgcta gctttccttt caaaaaaaaa aaaaattgtt  81300
cctaaccgat cacatagtcc agtagtccag tagtaagatt tttgttaagt ttattgttac  81360
tgaatatatt gtttggcctg cagttgttat ttctctcaaa acaaaattat ttggtagtct  81420
caagtacaaa aagaaagaca gatcagacaa gttgttttac tctactagtt tcaaattgat  81480
catctctgtt tgttcttcat tcattttctt tctgtaagag agtttgctag gatggtgatg  81540
tggtcatgtg gatgatcaaa tggactacat cagacgcatc acactgctgc ccaaccttta  81600
cccactgtag acaaatggag tgcaggtcct aaaccaggcc agaagtttgt tcagtgttct  81660
tgttccaaaa taaacattct ggatggcagg ttatttcatt ataacattca ctcttatagc  81720
ttgcttagtc aaaactacaa ataaggtctc ctaaaaaaat gcatcgacgt tgatatctgt  81780
gttttctgcc atgcagaatg acttgctctc aatggttgaa gctgcaatct tccaggctca  81840
tttctggctg aacccaaatt ggtggcttgg aggctggagc tgcatgacat cagagataac  81900
aatggccact ttttgttgcc atgggtgagg gtacatggat catgccgcta agcctttact  81960
ccgagctagc agaaaactgg ctggctgtag atcgagttcg ccatcgccct caactttgtc  82020
gatgcgatgg cgatcatgga tagatgtatg tatgtaaaaa cacaaatttt agtgattaca  82080
gaacttattt ttctctttaa tcagattatt aatcagtggg atttttcttt ctctagtact  82140
gtataaaaat actttttttat cgtcaatcct cctaaaattc ctatttataa actcattttt  82200
cttcagtttt tttttctgta ttttggtttt ctttcctcta cgtgactaca cattttgaat  82260
tgaacatgct ctgtatctgc tcggaatact tattattcag ccaacttaaa tgcatgagat  82320
ttgctccggt tcaccaaaaa ttacctcgag gtaccagtac ctcatggtat caaattgttt  82380
ccgatcgtga aataattttg taccgttagg taccgtatct cgagatctaa atgcataggg  82440
gcatttggaa tatgcactta acagttgttt gaacacttcc aaggaatatc tcctcagttg  82500
```

-continued

```
tcggacgact cattcatttt catcgcttcc aacaataatc aactgtgtct cttcctctcc  82560
ccccaatgct ccccctagat ccggccctac cgccgctaga gctgaccagc gtctatgcgg  82620
cggttaggac agtggcagcg gggaggtggg aggtggaggc gctgcggtgg cggccagagg  82680
cagccgggcc cgcacgctga ccttccaggt tggtgatggt tggaggtggt cgggaggacg  82740
gcaggtagcg gctatgcgtc agcgatggag gaccttcgga caacggtggg gacggcggcg  82800
gcctaggacg acaacgactc tcgtcggcgc tggcggccct aggggctccg gtggaggaca  82860
acggctattc acgtcggcgc cagtggccct gggggcattg gcggctcccg tcggccagcg  82920
gcccaggatg tcagcggttc tcgttggtgc cggtggccct aggggctgcg gcggaggacg  82980
gcagcggttc acgtcggcac tggcggccct aggggtagcg gtgccccagg acagcggcag  83040
ctcccgtcgg cgccggcggc cctaggggta gcagcggagg acggtggcgg ttcccgtcgg  83100
cgttggtgac ctgggacggc ggcggtctga gcactatgga taatggaggc ctagaaattt  83160
ggcaaagtgg aagctaaccc cgtcggttcg tgtttggttg gctagttcta actgaacgat  83220
gaacgacgac ggttgaaaat gtgctaactg gcggcgtgag tcaactcacc taaaacggat  83280
aaagatggca ccaacagagg tttgcatgga cagtgcacta ggggcgatga agaatacaca  83340
acttccactc gtcaaacttg gctgtttcat gagaatatgg cgggaagcag agaagctggg  83400
atgtgtcgag gtcgtttggt tttcttttat tttttggttg tgtgttctcc tccttgttga  83460
ggtgtgagtc taagtgctct tgtatccttt tggctgtgta tatccttcgt ggatatagag  83520
gccagattaa tgaaaatcca ttattaaaaa aagttgttgg tcggctaatt aaacctgatt  83580
aagaattcca tgtgcaggga catgtactag cgttcccaaa tcttagaaca ctttggcttt  83640
acaatttgga tcagctaaga gaaatcagat ttgaggacgt cagttcaccc cagttggaaa  83700
agatagaact ctcttggtga aggttggaat cagggattat tggtatcatt caccttccaa  83760
agctcaagga aatttcactt gaatacagaa gtaaagtagc taggcttggt cagctggagg  83820
gagaagtggg cgcacatcca aagcatccag tgctgcaaat gatggaggat cgaagctatc  83880
gcgacctagg aggtgatgcc gaagtatctg ctgtacaagt gcaagcagga tcccctccct  83940
gagcaagagg gagagagcac gcaggtgatc acgttgacga caaactacag gtcagtcact  84000
ccctacatgg cagcttaatt agctagtttt ctcttcttat tcagtattag ccgtcaggtg  84060
atatcgatga tttcaactca cctttcatct ctctcctttc cttaacccaa cagtgaacag  84120
ataggcacag ctcaagctgg tttgatcaag tgatcatctc ctcctccatt ggcatctcgg  84180
gtcgtccctg gctccctgct tctgcggctc cgagcagggg tgctgatcta aggaggcgtc  84240
cactttttttc aattgcgtct caggtatgaa ttgttcgatc tgatcttttc tcgtgatatg  84300
ttactgttcc agcatgagta tttcaaccag cggcttagaa tttttcgttt gatcaggttt  84360
tttcccccttc ttacctgggc actatacttt tggttttctt atttcatttt tgctgtgcac  84420
accaggtgtt tgctagaatg tctgaaagag cttgtgttca tggttagctc aacattatgt  84480
gttagtcata ttttatatcg ttgctgacct atcacatagc gcaggagttt tttgctatgt  84540
ttattgttgc ttgctgttga ttttcctttt tgtaaagaat attagctttt tagataacga  84600
aaagaatatt acgtatcctg caaaaaggat tgatttggtc gtcactggct agtaggggtg  84660
aaaacggtac ggaaactttc cggattccgg acctattttt agaaacggaa tctgtcggtc  84720
ggaatttttt tggaattttt cggaaacgga aacgaattcg gaaatatttt ctcggaaacg  84780
gaattggaaa tgataagggc agtttccatc ggaactcgga atcggtcgga aactttctgg  84840
aaattttctc ggaatttccg gaaattttgt gactgaaata gtgaatacca tggtatttgg  84900
```

-continued

```
ctgttatttt ttttaaagta tttgttatgc aaatctgaag ttacataaga atattttttt  84960
cctgcattgg gatttatcaa catcagtact ctcttaaaca tagataattt atttcataga  85020
ttgtgttctg tgattgagac ttaaaaaata gacttatatg attgtgtttt atgatgaatt  85080
gttgaccgtt gagacttgag aattggattt atcagtttga ggggtttttt attccgataa  85140
atttcgttac cgtattcgtg ccgattcgtt ttcgctccgt tttcggtttc gataatattt  85200
gattccgttt tcatatccgg agtttccgat tccgattgtg aaaacaatat gaaaacgaaa  85260
acgataacgg tggtttttgt ccgtttccat accgttttca cccttactgg ctagtacaaa  85320
acaatttgga ttgtcggagc tgctggtctt gggaaactac tcttcaaagg tggtttacaa  85380
aactctgatg ttagtaccaa gtccttgcag ggagagatat agaagagtgg gaaattttgt  85440
atgctcaact tccatcagaa cttggatgca acccaagcct tgcagcaatg aagaaggtgg  85500
tagcccttag ttacaattac ttgccttctc atgttaagcc ttgctttcta tacctttgca  85560
tctttcctga ggattttgat atccaaagga agcgcctagt tcatagatgg attgcagagg  85620
gatttgttag agctaagggt ggagtgagaa ttgttgatgt gacagagaaa tattttaatg  85680
agttgattga ctgaagtatg attcaagcat ctagagtgaa catagaaggt actattaaga  85740
gctgccgagt ccatgatatc atgcatggtg taatgatatc aatatcggaa gaaaattttg  85800
tatatctgat gagggatgat ggaactagtg tagtggagga aaaatattcg ccatgtagcg  85860
taccatgaca gcaagtgttc tattataggc atggactgga gccatgtacg gtcgttaact  85920
ttgtttggcg atgagagacc caaagagctc tcacctccat tctgttctcc ccaattgaaa  85980
atgctaaggg tgctggatct actagatatt atatttggac tagcaaaaag atatggataa  86040
aatatggttg ttgcgtcact tgaaatatgt caatattagg tgttccaatg aatgctcaag  86100
catttatgca cttcctagtt ccataagaaa attacaagag ttacacactg gacatatctg  86160
acacttatat tacaatgcta ccaaatgaga ttagtaaatt gcagtctatg tgtcctccgt  86220
ggtagaagac aaggatccta ctatgacctt gatacatata atcgtaagga atgtgtactt  86280
attttatcac gtattccttt gattatggct ttaagtgatt ctgataacca tagaagacta  86340
attaccgatc tacacacggg ttgttcaagt cattggcata taattaaaga tggtgcaagg  86400
gtaccaagtg gaatcaagaa tttgaagaga ttgaaagtac tagagatagt ggatatcgcg  86460
gtaactgaca gcagagcaat tcaagagttg ggggaactta accagctaag aaaactaagt  86520
gtcatgacaa aagggtcgaa caagaaaaag tgcaaaatac tttgtgcagc catcgaaaag  86580
ctcacttcct tcaaatctct ctatgtggat ggtcatggat actcacttga tggaacactt  86640
gagtggcttg attctatttc ccatcctcct tccctcaaga gccttagatt gaaggggtgt  86700
attaaggaga cacccaactg gtttagggag ctcaaacact tggtgaagat ttacttatat  86760
aaaagtcgcc taaatggaga taccatggag atactcgggg aactacataa tctcatggat  86820
cttcactttc gttggtatgc atacgttggg gagaagctag tgttcattga gggagcattc  86880
caaaatctcc ggaagcttgt tgttgaaact gaggataaac taagagaggt gaggtttgag  86940
gagggcacct caccccagat ggaatggata gaaatctgtc attgcgaact gatatcaggg  87000
attgttggtg tcaagcacct tccaaggctc aaggagatag gactcaaatc tgctaaagtg  87060
gcaaggcttg gtcagctgga gggtgaagtg gacacacacc ccaatcagcc catattgcgc  87120
ctgtctgaga agcgaagcta tcacgatctg gggaaaccc atgtatctgc tgttgaggtg  87180
gaagtggcgg atgagcccct tgctcaccag cagcctgtgg acgttgacga tcgaacaaca  87240
```

-continued

```
accggtcagt cctgcattat gacattcatg cagctacttg ttttgttttt ctcttttgtt  87300
cagcattagc ttagcttatc tcattttctt accttttttcc ttcttccttg ttgtctctag  87360
caaaacccaa cagttagcga agaatgctcg atggtgctga tctcgcctct agatggtgat  87420
gatgatcagc tccccgttgt gagctctcct ggctgcctgt agtgctgatc ccggagtccc  87480
ctgctgcatt ttccacctcc cgtgttgagg tcagttcagt atctccccta agtcaccatg  87540
ccggtatttg tttgtttcta tatgatttga ttagtaggat gctttttgtt tttgaaattt  87600
tgtatcatga ttggttggag cgtgtgatta ggtttcttac agttgcagca gaggtcgtat  87660
tttgttttaa tgtgcacacc agatgttcgt ccaaatgtct tgtcaaaatt tttttatctt  87720
ttgatttgtc aagtatttat gattcgcaat atgaaacatc gttggtcagg atctgtgctg  87780
cacgtatcga tgcaatgtaa tgatccaagt gacggttccg tttgttcgtt atcttcttat  87840
caatttaggc cctgtttttt tcagcttgga atttttataa tctagattat tgagtcagat  87900
tactataaac tagattgtta taatctgtag tagaataagc ggttagttgt ttctttccta  87960
gattattaga gcctagatta ttgggtttac aagtctaaag agggactggg gtggcatggt  88020
gggtaatttt tcactcaata atccggaaaa agctcaccta aatgagctta tcagattaga  88080
ataagctggg ttccagatta taataagcta cttcaataag ttatctgttt ctttcagctt  88140
actcccaata atctggatta taataatccc aagctgaaag aaacagggtc ttagtgttcc  88200
gtaccagatt ttcaaaaagg aactaatatt tcttaccaac catttatgat gtaatctctc  88260
tatccactgt cataccgtgt tacctgtaga ctgtagtctg tagacataaa aaaaaagtac  88320
ctttttggtc tctgaaacat ttacctgtat ctatcgactg gtctccaata tatccttttg  88380
ttttcgttca atttgaaacg gccttctttt tgccaatcca ttaaagaact ggtttgcgaa  88440
tgtttagttt gagagtagct tgaccaaatg ggccttaagc ctgattgcag tggattttac  88500
ttgctcaggg taaaaccaaa ttaaaggatc atgttcattc tcaggaatct ctagcatgga  88560
atgagaacaa aaatcataac aatggtcaag gtaacaagac tgaaccaacc accatggcgc  88620
taatcatcga tctgaaataa catcggaact tgaaagcttc agaacgtcca tcgtatattc  88680
gtcagtgcgt gcaaactctg aagtctgaac tgcgaagtag tcatcaaggt cgtagtctcg  88740
tagatatgat gttcgttacc aatacctgtt tctaatcgat tcctttatgt ttttccgttc  88800
attttctctc agttttatgg aacactattc agctggggac tagatgtgga acggagtaca  88860
ttagacgcac gaatgcatgc attgatgcat agaatacggg tcttggaggg atacgcgtag  88920
gctacgatag cataaattaa aattttctac cgcgtaaact aagaaccata caaatattag  88980
atcatagatc gttaccactc gacgcgctgc gcagtggaag aaagcgctaa aaaggcgaag  89040
gaaccctcgc gatatagcgc gcatcgatgt tgaagaagta gtcgatcgta ccggctcgac  89100
cttctcctcc tcgtgcgttc tcctcgccgt actcccatgc cgatcagtac cgcaaagcag  89160
tggcgcctct accggtatcc acacgtacag ggacggaacg ccatgtgcag atgtgctagc  89220
acctgcgcac ggctagggtt ttgctcgggg aagggagtgg cggctagggt ttctcacgtg  89280
atgcaatgtc tccgccggtc acacccctca cgaatatata ggatccatga ctcgggcctc  89340
caaggcccgt gggactccta ttcggatccc tatccgaatt aagctcatac tggatctcca  89400
tccaatcccc ttattccggc ccattaagtg tgcggccctg taggttcatg cacactcggc  89460
tgtaacccga aaactctttt tggtccacgt gtcaacagtg gcccctagca gaacgtattg  89520
accgaccggg catatacaaa catcatatcg gttgaacctc tagtgtatac ttgtatgaac  89580
ctctttgcct cacgagatcg attaagctca aggctagata tgtgccatcc tctaatagct  89640
```

-continued

```
caatcattca ctcgaacctg tgatagatta cataactcat gattgtcctc aaccaccttt  89700
ggcatggcca tgcattttca taatctataa catcgaggga cccagagata tctctccata  89760
aaaggggcaa atcccatctt gattattcat atctcactac acgtttcata gcatacccga  89820
aaactacttt tataactacc caattacgga gtagcattta gcagtcccta agtaagctac  89880
tacacatgtt gagaaccatg ataatctcag gtctaaggat tcaacaccaa cactaaatga  89940
gatcactgat gacacaacac atatgtctct tgcagtgtct catgttgggt ctatccaaca  90000
atatgtttcc caacatgtgt ccacattatt aatttggtat ctctatacca taatccataa  90060
gacatgatca tcaattaata catgtgctga tcattaaaca tatttgtttc acatatgata  90120
tttgatcagg gatcttttag aaatagcaac atacaacata aagagtctca taaaagaatc  90180
acatattcag taaccaataa tgagttatct attttaagga acaatgtcgg ataaatatgt  90240
aaacataata tatgatacaa tcatctctat tattgcctct aggacatatc accaacaggt  90300
ctgcaatgca gtgatgatga cacctgtgca aaatatttca gtcagggaac tcaggatcac  90360
taaaagatgt cgatgttgcc tctctggaat gtatgacatc tcacttctca ggaaggattg  90420
gagccggtgc cgccatcaga aatcacaacg gccagatttc tgtgtcattg agatgctata  90480
tgtatcggaa gacttcagat aaaaaaatat cttctcatct ccaggttact gaacaacgga  90540
gagtcattct actcctatat gctactttta actttcacta gctagtctgt atgattgatt  90600
tgtttccttt tttttttttg cacttacatt tgttaatgta tatgtgtgta tatattagga  90660
tagagggccc attttggaca tgtatatgtg tactgttgaa ctaatgttga ccagaatatc  90720
tgaaattccc caacattatg aattgcgctg gatctagatc accacgagaa gctaagccgg  90780
ttgtgttggc gggattggtc gcttcaaaaa ctagatgata ccccgcgcgt tgctgcggga  90840
ttttgtaggt agaaatggag agctacacgt ggaggcataa gagataaatg taatagtagc  90900
cattggaaat ggtaattttt ttcaaacaaa caactatttc tgtaggatga aatctataaa  90960
ctggagtagc aacatccgtg aaggttaaga tagcatttct cagatatagt aatagcaacg  91020
caagagatac taattttgat tattggtatt gaccttctct tcagttagac tgcatttgag  91080
gtaatccatt ttttatgtaa gaaatgttag aagcatatga gggtcagaga tagcttcagt  91140
ttgttgaggt tatagaagaa tccatttgag caactgcatc catgttcact tgtgaagaac  91200
agacaaatga aaaatgagca acatctcgtt tgaaagtttg aggattcctg aagggaagag  91260
caataaatgg caaagtatag acaatacgac gatgcaaaag aagctagaag cagttagcat  91320
gacaacaaag aacgcatacg gttaacatga caacagagaa tgcaaggtac caggaaggca  91380
ggaatagagt aatagagaaa ataatgtaat aggagtaaca tttattaatt ggtgattaat  91440
gataacctgc tggttggttc ttgttgaata tccatgtgtt ggaataagaa taaagctgtt  91500
gagaatagga gaaatgaaag ggagttgtca taaggagaaa cataatggtg tatgtgatac  91560
ttatagaggt tgagtagtaa tgtggtatcg aatcgtgccc aattgttcat cacagaataa  91620
taatcaaaac cacctttgat tttacaaaaa taatatctga tttattgtta actgcttatt  91680
gaattagcat taaacagtac aatcagagta gctaattgaa tcgtggaggg tgtggccctt  91740
tgcctaactt tttatgcacg tttatgcatt tttattaatt tattgaatca acatagtgca  91800
acccctatct atccctttac cataaagtaa attcaaagaa aaaaaacaat gtttatcttc  91860
tcatgttaag tgttgttaga atgtctgaat cagaacccat cttaattttc tctgtttctt  91920
aggatatcaa tcatgtctta gagctgaaag tttgtatcaa cagaaacaca ataacttgta  91980
```

-continued

```
gtattttggg ctaaaagatc cataaaactg aagataaata gtcagatggc cttgatgaat  92040
aacccaatgt ttgacaaact gttcaatttt gctattacaa atagcattct ttatactcta  92100
gccagaaaaa aaaatgaaaa atggatataa agtaggatca tcatatacca aagaagaatc  92160
aggatagata tatcaaaaat tagggatcga tgtgtatgaa aaatagctag acagtgttgt  92220
tatggaagga ataacttgta cctcttgcga agcaagtgtc gcagtatggg catataataa  92280
tatatagaaa tcaagttacc atgaatgaat atggggcaat tatgattacc caatgtatat  92340
acagattgct ccagctgttg ctttggatgg gaatgtcatg gggactaatc tcagcggtag  92400
cccatagttg ctgatgcaac aatagtaagc aatctgctaa tggaaaacaa tctgcatccg  92460
gaattcataa ggtatatact gcgtgatgta aaattggtat acataccaat gatcctcata  92520
ccatgaattg tctcctttag tgaagtgtat atactaaata aatttcaatc cggttgaacg  92580
gagacggtag aaacctgaag tagagccgaa acaaaaccaa tccctccttt cttaattctt  92640
gaagaatatg aggaataaca taaacaagtc aatctagtgt gaccgaaagc agaagccaat  92700
ttattggatg aaaaatatat ggctcataaa gaggaagaag cataccttcg ggaggttggt  92760
gtgttcgagg tgaaggggag gttgaagatt tcaggggagg aagaaactaa gacaacaaat  92820
cgaacgacgt tttgtggtga ggagctcgac atccatgaaa tctgatcggt ttttaatgtt  92880
ggccattaag actgctcgtt ggtgggtgcc ggcagtttct gtcttttgtg atatgccgag  92940
gaggcgagca gcctaggagg tgggatggag cgaggaggtt ggggaaacgg cgcggctggt  93000
gggccagttg cgtgcgcgcg cggaggttgg ggaaggttgg ctcgacggag acacaggatc  93060
gtcggggagg gaggaggaag gagagatgcg cggctgagat gaactcgcct ctcgcgtgcg  93120
cgtaggggaa acggtccggc catgacgcgc agctggcata cccgtcgcat gcgcgcgcgc  93180
ccagggggaa cccggcgcgg cggagtcgcg gagaccgcgg ctggtgccgg taggaagcac  93240
gagcgcaaga gaccgatcga ttgccctggc tttggagtgg ataaggttcg ggaaacggaa  93300
cctagtgcct gaatgctgag agtgagattg aacctcactg gttaggtaat aggacgagta  93360
aacgagaagt caacccaaaa cattggaatt cggatacagg gtacagatgg acaatattgt  93420
taaacattgg aaagccaacc caaaacaaag ggcagatctc gaggtgtagt ggacagagac  93480
tggggaggcc cggcatccaa acccacataa cacgcctttt ttaaaaaaaa acaaaatgag  93540
gcacaaactg taaaatccac ctaacacgtg atataggcgc cagctaagtg ctaacgttag  93600
agcaggtaca atagcaggct atatgccagc tgtaaacata ttttaagaag ataaatcagg  93660
agagagaaga gcagcgggct acagatttgt agccagctgt agcacgaact ccaagacgcg  93720
gtgtgtctat gacaggtggg gctaggtatt aatagtgtag tatgtaacta tagtatgaat  93780
gagctattag attggctata gatgaattag agctagtagt tggctatact attgaacttg  93840
ctcttagggg aatatggttg tccccctgtg cgttagtgcg tacagtgatg tgaactacta  93900
taagagcagg tacaatagtg gactattagc cagttgtaaa tatattttaa tgagataaaa  93960
gatgagagag aagagtagct ggctacagat ctgtagccag ctgcagaacg gactccaaga  94020
cgtaatgtgt gtatgacagg tgggaccata tattaatagt atagtaagca actattgtat  94080
aaattggcta ttagattggc tatagattaa ttggagctag taatgggctg tactattaaa  94140
cttgctctaa tgataatcct ctctgcttga attgttcagt gtaaaagcta gctacaaatt  94200
ctgattgcag agccagaaga gccagtcgca ttgtcctatc tcctttgcgg ttgtgagctg  94260
cttgctgttc tgagcgtgaa ccgtgaaggg agatctagtc gaggagagtc gatggcggag  94320
acggtgctga gcatggcgag gtcgctggtg gggagcgcca tcagcaaggc cgcctccgcc  94380
```

-continued

```
gctgccgacg agaccagcct cctgctcggc gtcgagaaag acatctggta cgtaatatgt  94440
actgtggctc tcgtttattc tgtactagct tactgatcag catttattgt atcgacatcc  94500
ttcttagcct cgattttgtt ggccatcaat cctgatcgga acaaatcact aagtcaagca  94560
aatcaattga tgagtgcaca aacttttttt ttttgcatga ccaatcttga gttcttgagg  94620
ggcgaaacag acgcacccga ccgcagtcac cctctccctc ctcccacagt cccactcctc  94680
ccctccgcct tgccgctacc cgagcgaccg ccggaaagcc aagtggctgc aaggacggtg  94740
gcggtggggc atgctctctc tctctcggcg ctgcaaagga gggggcaccg tcgcatctag  94800
gatggcaaag gcgtctccac gccagtcaga tccggtgagt ggctggcaga aaacgaggcg  94860
gaatagcgga gggccgagcc agtgcttggt gtggctagca acatgggagg ctagcgatgc  94920
ggtagcaagc agtggtggta actacaaatc tatagctccc ttgccagatc tgacgacccc  94980
gcaaccggat ctggcgatgg cccaacggtg tcggaggcta cgcatccgag aatgttttgg  95040
taaggcgacg gcacaatcgt gcgacgaccg gtaatccatg gggtgagga ggcaacaagg  95100
tgcaaccaag gaagcaccgt gacatgccga ggaggatgcg gcggctcgcc atgagtggat  95160
ctggaagcga cagatgtagc tagatttggt gggcggggtc gcagcagcaa catgtgccgc  95220
cgatgcgatg tggcagtggc tgcttgagat gccagatggg gcccatgtga tggaggccag  95280
aggagcagcc agtgggccga cggggaggat gcaaggtgtg gtgggctgca gcgacggctc  95340
ggtgcgagca agagcgacgt ctgtgcatgc tgggacatcc tagcggggcg gcgtgatggt  95400
aggaggtcgg cagaaaaaat agcgtgccac ggaaggtggg gccatggctg gtcggcggtg  95460
gggcatcggc gcagcgaacc cacaggctag cggaggctgt tggggtggtg gaacgcaggg  95520
gtggtgatga cagggaaggg tgaaaatcta gctcggtgtt tcatcgggcc ggcaacgatg  95580
acacgttcaa gcgccgtctt ccccctttgg ggcgttgtcg agctatgacc ctctccctcc  95640
tcacaggact ctccagatga aaacctagtc catttagatg ggtcatggcg gcaaccttgg  95700
catcatgatc ttcttggagg cattgtccag gaggtcttgt ttcctcacct tgcaatgccc  95760
cgatcatttt tgtctttggg attctttcag tcgttgtcat cgggttaccg tgagggacaa  95820
gtggattgtc ttgtctctct cgccctctca ctcctcaacc cttctacgtg ataatgattg  95880
ggagcccgtt gatgaccttc tatttggatc tagtgctcgg tggggccttt gcaacctagt  95940
gtaggactag cggtgatcgg tcacgcatag aggcggtcgg ttcggtgcta gtgcttctct  96000
tggggtatgt aaggagtcgc tagaatgtgg tggtgtgctt tttatttttc ctttccctga  96060
ttataacctt ctagggctgt aattttgttt ttttttcttg ctatattaat atgaaacttc  96120
acactgcctt gtgcggctcg tttaaaaaaa aaacttgagt tcttgacact ataagtatgt  96180
tagtagtgga gtcgacatta gtttatctaa aacatctctt catatatatg aaggccacta  96240
atgatttttc tttcctaggg aaccaaagtt ccgcggtatg ttaatccaca aatccccttg  96300
taagatatcc tatggcaaat gaactaaagg catgtacaat gataataatt aataggagaa  96360
tcttaacatt tctaattagt tctaattagg aatattaact gatatggaag agagagagag  96420
agaaagagga gagatagaac attgttgtta tggttaacaa tggctcagca actacttgcc  96480
tctttaaaat ggaaacttgg ttgcgagggt gaaaaaaagg aaagaatatt agtaaagaat  96540
atattttttg tttagtagtt aaaatatttg ttgtctcaat tgtttaaggg cacactctaa  96600
ataattttgt gttatctaag agtccatacc atgcagagga cccgcgtttt ccacgtggac  96660
aaccagagca gtaacaaacc ctagcgcctc caccccctta gatgggctgt ggcggcgctt  96720
```

-continued

```
tcggcattgc gttttctttg gaagtatcat ttagaaaatc ctattattgc ctagcctgcc  96780
ttaaggaagt tcaggcgaca cccttggatg gcgatgtccg agagcccgtg gatgtttagt  96840
tgtttagaca tggtgttgga cggtcgaatg gtgggcctgt tgtaggtatg gtggcatctg  96900
gcaaccagtc atgcttagca atagattcct atgcagaaga cattcgcaat caatcagctc  96960
gaaatgtgga tgaagctgag cttgttgggt tttctgactc caagaaaagg ctgcttgaaa  97020
tgatcgatac caatgctaat gatggtccgg ccaaggtaat ctgtgttgtt gggatgggtg  97080
gtttaggcaa gacagctctt tcgaggaaga tctttgaaag cgaagaagac attaggaaga  97140
acttcccttg caatgcttgg attacagtgt cacaatcatt tcacaggatt gagctactta  97200
aagatatgat acgccaactt cttggcccca gttctctgga tcaactcttg caagaattgc  97260
aagggaaggt ggtggtgcaa gtacatcatc tttctgagta cctgatagaa gagctcaagg  97320
agaagaggta ctttgttgtt ctagatgatc tatggatttt acatgattgg aattggataa  97380
atgaaattgc atttcctaag aacaataaga agggcagtca aatagtaata accacttgga  97440
atgttgatct tgcggagaag tgtgccacag cctcactggt gtaccacctt gatttcttgc  97500
agatgaacga tgccataaca ttgctactga gaaaaacaaa taaaaatcat gaagacatgg  97560
aatcaaataa aaatatgcaa aagatggttg aacgaattgt aaataaatgt ggtcgtctac  97620
cattagcaat acttacaata ggagctgtgc ttgcaactaa acaggtgtca gaatgggaga  97680
aattctatga acaccttcct tcagaactag aaataaaccc aagcctggaa gctttgagga  97740
gaatggtgac cctaggttac aaccacctac catcccatct gaaaccatgc tttttgtatc  97800
taagtatctt tcctgaggat tttgaaatca aaaggaatcg tctagtaggt agatggatag  97860
cagaagggtt tgttagacca aaggttggga tgacgactaa ggatgtcgga gaaagttact  97920
ttaatgagct aatcaaccga agtatgattc aacgatcaag agtgggcata gcaggaaaaa  97980
ttaagacttg tcgaattcat gatatcatcc gtgatatcac agtttcaatc tcgagacagg  98040
aaaattttgt attgttacca atgggagatg gctctgattt agttcaggaa aacactcgcc  98100
acatagcatt ccatgggagt atgtcctgca aaacaggatt ggattggagc attattcgat  98160
cattagctat ttttggtgac agacccaaga gtctagcaca tgcagtttgt ccagatcaat  98220
tgaggatgtt acgggtcttg gatcttgaag atgtgacatt cttaatcact caaaaagatt  98280
tcgaccgtat tgcattgttg tgccacttga aatacttgag tattggatat tcgtcatcca  98340
tatattcact tcccagatcc attggtaaac tacagggcct acaaactttg aacatgccga  98400
gcacatacat tgcagcacta ccaagtgaga tcagtaaact ccaatgtctg catactcttc  98460
gttgtagtag aaagtttgtt tctgacaact ttagtctaaa ccacccaatg aagtgcataa  98520
ctaacacaat atgcctgcct aaagtattca cacctttagt tagtcgcgat gatcgtgcaa  98580
tacaaattgc tgaattgcac atggccacca aaagttgctg gtataaatca ttcggtgtga  98640
aggtacccaa aggaataggt aagttgcgag acttacaggt tctagagtat gtagatatca  98700
ggcggaccag tagtagagca atcaaagagc tggggcagtt aagcaagctg aggaaattag  98760
gtgtgatgac aaatggctcg acaaaggaaa aatgtaagat actttgtgca gccattgaga  98820
agctctcttc cctccaatat ctctatgtga atgctgcagg aatctcagat ggtggaacac  98880
ttgagtgcct agattctatt tcctctcctc ctcccctact gaggacactc gtgttgtatg  98940
gaagtcttga agagatgcct aactggattg agcagctcac tcacctgaag aagatctact  99000
tattgaggag caaactaaag gaaggtaaaa ccatgctgat acttggggca ttgcccaacc  99060
tcatggtcct tgatctttat cggaaagctt                                   99090
```

<210> SEQ ID NO 14
<211> LENGTH: 1214
<212> TYPE: DNA
<213> ORGANISM: Oryza minuta
<220> FEATURE:
<221> NAME/KEY: misc_feature
<222> LOCATION: 806, 835, 891, 906, 946, 964, 970, 991, 997, 1018, 1060, 1091, 1125, 1129, 1131, 1148
<223> OTHER INFORMATION: n = A,T,C or G

<400> SEQUENCE: 14

```
gatttgagga cggcagctca cccctgttgg aaaagataga aataggcgag tgcaggttgg     60

aatctgggat tactggtatc attcaccttc caaagctcaa ggagattcca attagatacg    120

gaagtaaagt ggctgggctt ggtcagctgg agggagaagt gaacgcacac ccaaatcgcc    180

ccgtgctgct aatgtacagt gaccgaaggt atcacgacct gggggctgaa gccgaaggat    240

cttctataga agtgcaaaca gcagatcctg ttcctgatgc cgaaggatca gtcactgtag    300

cagtggaagc aacggatccc cttcccgagc aggagggaga gagctcgcag tcgcaggtga    360

tcacgttgac gacgaatgat agcgaagaga taggcacagc tcaagctggc tgacgatctc    420

ctcccccatc agcgtcgtca tcagcgagca gaaagggcag agcttccctg cttctgcgtg    480

cacctcaccg ctctgactcg gagggacatg atgatcaatg aggcttccag tttccaaatg    540

tgtggctaac acaccaggtt gtccctatcc gagaaaccaa gttgattgca ttgtggaggg    600

gaatatgaga tcagaaatca aatgagagtt tgctaggatg gtgatgtggt catgtggatg    660

atcaaatgga ctacatcaga cgcatcacac tgctgcccaa cctttaccca ctgtagacaa    720

atggagtgca ggtcctaaac caggccagaa gtttgttcag tgttcttgtt ccaaaataaa    780

cattctggat ggcaaaatga cttgtnttaa tggttgaagc tgcaattttc caggntcatt    840

tttggctgaa cccaaattgg tggcttggag gctggagctg catgacatca nagataacaa    900

tggccncttt ttgttgccat gggtgagggt acatggatca tgccgntaag cctttactcc    960

gagntagcan aaaactggct ggctgtagat ngagttngcc atcgccctca actttgtnga   1020

tgcgatggcg atcatggata gatgtatgta cgtaaaaacn caaattttag tgattacaga   1080

acttattttt ntctttaatc agattattaa tcagtgggat ttttntttnt ntagtactgt   1140

ataaaaanac ttttttatcg tcaatcctcc taaaattcct atttgaaaaa aaaaaaaaaa   1200

aaaaaaaaaa aaaa                                                      1214
```

<210> SEQ ID NO 15
<211> LENGTH: 2422
<212> TYPE: DNA
<213> ORGANISM: Oryza minuta
<220> FEATURE:
<221> NAME/KEY: misc_feature
<222> LOCATION: 2014, 2043, 2099, 2114, 2154, 2172, 2178, 2199, 2205, 2226, 2268, 2299, 2333, 2337, 2339, 2356
<223> OTHER INFORMATION: n = A,T,C or G

<400> SEQUENCE: 15

```
aggaaaaatt aagacttgtc gaattcatga tatcatccgt gatatcacag tttcaatctc     60

gagacaggaa aattttgtat tattaccaat gggagatggc tctgatttag ttcaggaaaa    120

cactcgccac atagcattcc atgggagtat gtcctgcaaa actggattgg attggagcat    180

tattcgatca ttagctattt ttggtgacag acccaagagt ctagcacatg cagtttgtcc    240

agatcaattg aggatgttac gggtcttgga tcttgaagat gtgacattct taatcactca    300
```

-continued

```
aaaagatttc gaccgtattg cattgttgtg ccacttgaaa tacttgagta ttggatattc    360
gtcatccata tattcacttc ccagatccat tggtaaacta cagggcctac aaactttgaa    420
catgccgagc acatacattg cagcactacc aagtgagatc agtaaactcc aatgtctgca    480
tactcttcgt tgtataggac agtttcatta tgacaacttt agtctaaacc acccaatgaa    540
gtgcataact aacacaatat gcctgcctaa agtattcaca cctttagtta gtcgcgatga    600
tcgtgcaaaa caaattgctg aattgcacat ggccaccaaa agttgctggt ctgaatcaat    660
cggtgtgaag gtacccaaag gaataggtaa gttgcgagac ttgcaggttc tagagtatgt    720
agatatcagg cggaccagta gtagagcaat caaagagctg gggcagttaa gcaagctgag    780
gaaattaggt gtgacaacaa acgggtcgac aaaggaaaaa tgtaagatac tttatgcagc    840
cattgagaag ctctcttccc tccaatctct ccatgtggat gctgcaggaa tctcagatgg    900
tggaacactt gagtgcctag attctatttc atctcctcct cccctactga ggacactcgt    960
gttggatgga attcttgagg agatgcctaa ctggattgag cagctcactc acctgaagaa   1020
gatctactta ttgaggagca aactaaagga aggtaaaacc atgctgatac ttggggcact   1080
gcccaacctc atggtccttc atctttatcg gaatgcttac cttggggaga agctagtatt   1140
caaaacagga gcattcccaa atcttagaac actttggatt tatgaattgg atcagctaag   1200
agagatcaga tttgaggacg gcagctcacc cctgttggaa aagatagaaa taggcgagtg   1260
caggttggaa tctgggatta ctggtatcat tcaccttcca aagctcaagg agattccaat   1320
tagatacgga agtaaagtgg ctgggcttgg tcagctggag ggagaagtga acgcacaccc   1380
aaatcgcccc gtgctgctaa tgtacagtga ccgaaggtat cacgacctgg gggctgaagc   1440
cgaaggatct tctatagaag tgcaaacagc agatcctgtt cctgatgccg aaggatcagt   1500
cactgtagca gtggaagcaa cggatcccct tcccgagcag gagggagaga gctcgcagtc   1560
gcaggtgatc acgttgacga cgaatgatag cgaagagata ggcacagctc aagctggctg   1620
acgatctcct cccccatcag cgtcgtcatc agcgagcaga aagggcagag cttccctgct   1680
tctgcgtgca cctcaccgct ctgactcgga gggacatgat gatcaatgag gcttccagtt   1740
tccaaatgtg tggctaacac accaggttgt ccctatccga gaaaccaagt tgattgcatt   1800
gtggagggga atatgagatc agaaatcaaa tgagagtttg ctaggatggt gatgtggtca   1860
tgtggatgat caaatggact acatcagacg catcacactg ctgcccaacc tttacccact   1920
gtagacaaat ggagtgcagg tcctaaacca ggccagaagt ttgttcagtg ttcttgttcc   1980
aaaataaaca ttctggatgg caaaatgact tgtnttaatg gttgaagctg caattttcca   2040
ggntcatttt tggctgaacc caaattggtg gcttggaggc tggagctgca tgacatcana   2100
gataacaatg gccnctttt gttgccatgg gtgagggtac atggatcatg ccgntaagcc    2160
tttactccga gntagcanaa aactggctgg ctgtagatng agttngccat cgccctcaac   2220
tttgtngatg cgatggcgat catggataga tgtatgtacg taaaaacnca aattttagtg   2280
attacagaac ttatttttnt ctttaatcag attattaatc agtgggattt ttntttntnt   2340
agtactgtat aaaaanactt ttttatcgtc aatcctccta aaattcctat ttgaaaaaaa   2400
aaaaaaaaaa aaaaaaaaaa aa                                            2422
```

<210> SEQ ID NO 16
<211> LENGTH: 1251
<212> TYPE: PRT
<213> ORGANISM: Oryza minuta

<400> SEQUENCE: 16

-continued

```
Met Glu Ala Thr Ala Leu Ser Val Gly Lys Ser Val Leu Asn Gly Ala
1               5                   10                  15

Leu Gly Tyr Ala Lys Ser Ala Phe Ala Glu Glu Val Ala Leu Gln Leu
            20                  25                  30

Gly Ile Gln Lys Asp His Thr Phe Val Ala Asp Glu Leu Glu Met Met
        35                  40                  45

Arg Ser Phe Met Met Glu Ala His Glu Glu Gln Asp Asn Ser Lys Val
    50                  55                  60

Val Lys Thr Trp Val Lys Gln Val Arg Asp Thr Ala Tyr Asp Val Glu
65                  70                  75                  80

Asp Ser Leu Gln Asp Phe Ala Val His Leu Lys Arg Pro Ser Trp Trp
                85                  90                  95

Arg Phe Pro Arg Thr Leu Leu Glu Arg His Arg Val Ala Lys Gln Met
            100                 105                 110

Lys Glu Leu Arg Asn Lys Val Glu Asp Val Ser Gln Arg Asn Val Arg
        115                 120                 125

Tyr His Leu Ile Lys Gly Ser Ala Lys Ala Thr Ile Asn Ser Thr Glu
    130                 135                 140

Gln Ser Ser Val Ile Ala Thr Ala Ile Phe Gly Ile Asp Asp Ala Arg
145                 150                 155                 160

Arg Ala Ala Lys Gln Asp Asn Gln Arg Val Asp Leu Val Gln Leu Ile
                165                 170                 175

Asn Ser Glu Asp Gln Asp Leu Lys Val Ile Ala Val Trp Gly Thr Ser
            180                 185                 190

Gly Asp Met Gly Gln Thr Thr Ile Ile Arg Met Ala Tyr Glu Asn Pro
        195                 200                 205

Asp Val Gln Ile Arg Phe Pro Cys Arg Ala Trp Val Arg Val Met His
    210                 215                 220

Pro Phe Ser Pro Arg Asp Phe Val Gln Ser Leu Val Asn Gln Leu His
225                 230                 235                 240

Ala Thr Gln Gly Val Glu Ala Leu Leu Glu Lys Glu Lys Thr Glu Gln
                245                 250                 255

Asp Leu Ala Lys Lys Phe Asn Gly Cys Val Asn Asp Arg Lys Cys Leu
            260                 265                 270

Ile Val Leu Asn Asp Leu Ser Thr Ile Glu Glu Trp Asp Gln Ile Lys
        275                 280                 285

Lys Cys Phe Gln Lys Cys Arg Lys Gly Ser Arg Ile Ile Val Ser Ser
    290                 295                 300

Thr Gln Val Glu Val Ala Ser Leu Cys Ala Gly Gln Glu Ser Gln Ala
305                 310                 315                 320

Ser Glu Leu Lys Gln Leu Ser Ala Asp Gln Thr Leu Tyr Ala Phe Tyr
                325                 330                 335

Asp Lys Gly Ser Gln Ile Ile Glu Asp Ser Val Lys Pro Val Ser Ile
            340                 345                 350

Ser Asp Val Ala Ile Thr Ser Thr Asn Asn His Thr Val Ala His Gly
        355                 360                 365

Glu Ile Ile Asp Asp Gln Ser Met Asp Ala Asp Glu Lys Lys Val Ala
    370                 375                 380

Arg Lys Ser Leu Thr Arg Ile Arg Thr Ser Val Gly Ala Ser Glu Glu
385                 390                 395                 400

Ser Gln Leu Ile Gly Arg Glu Lys Glu Ile Ser Glu Ile Thr His Leu
                405                 410                 415
```

-continued

```
Ile Leu Asn Asn Asp Ser Gln Gln Val Gln Val Ile Ser Val Trp Gly
            420                 425                 430

Met Gly Gly Leu Gly Lys Thr Thr Leu Val Ser Gly Val Tyr Gln Ser
        435                 440                 445

Pro Arg Leu Ser Asp Lys Phe Asp Lys Tyr Val Phe Val Thr Ile Met
    450                 455                 460

Arg Pro Phe Ile Leu Val Glu Leu Leu Arg Ser Leu Ala Glu Gln Leu
465                 470                 475                 480

His Lys Gly Ser Ser Lys Lys Glu Glu Leu Leu Glu Asn Arg Val Ser
                485                 490                 495

Ser Lys Lys Ser Leu Ala Ser Met Glu Asp Thr Glu Leu Thr Gly Gln
            500                 505                 510

Leu Lys Arg Leu Leu Glu Lys Lys Ser Cys Leu Ile Val Leu Asp Asp
        515                 520                 525

Phe Ser Asp Thr Ser Glu Trp Asp Gln Ile Lys Pro Thr Leu Phe Pro
    530                 535                 540

Leu Leu Glu Lys Thr Ser Arg Ile Ile Val Thr Thr Arg Lys Glu Asn
545                 550                 555                 560

Ile Ala Asn His Cys Ser Gly Lys Asn Gly Asn Val His Asn Leu Lys
                565                 570                 575

Val Leu Lys His Asn Asp Ala Leu Cys Leu Leu Ser Glu Lys Val Phe
            580                 585                 590

Glu Glu Ala Thr Tyr Leu Asp Asp Gln Asn Asn Pro Glu Leu Val Lys
        595                 600                 605

Glu Ala Lys Gln Ile Leu Lys Lys Cys Asp Gly Leu Pro Leu Ala Ile
    610                 615                 620

Val Val Ile Gly Gly Phe Leu Ala Asn Arg Pro Lys Thr Pro Glu Glu
625                 630                 635                 640

Trp Arg Lys Leu Asn Glu Asn Ile Asn Ala Glu Leu Glu Met Asn Pro
                645                 650                 655

Glu Leu Gly Met Ile Arg Thr Val Leu Glu Lys Ser Tyr Asp Gly Leu
            660                 665                 670

Pro Tyr His Leu Lys Ser Cys Phe Leu Tyr Leu Ser Ile Phe Pro Glu
        675                 680                 685

Asp Gln Ile Ile Ser Arg Arg Arg Leu Val His Arg Trp Ala Ala Glu
    690                 695                 700

Gly Tyr Ser Thr Ala Ala His Gly Lys Ser Ala Ile Glu Ile Ala Asn
705                 710                 715                 720

Gly Tyr Phe Met Glu Leu Lys Asn Arg Ser Met Ile Leu Pro Phe Gln
                725                 730                 735

Gln Ser Gly Ser Ser Arg Lys Ser Ile Asp Ser Cys Lys Val His Asp
            740                 745                 750

Leu Met Arg Asp Ile Ala Ile Ser Lys Ser Thr Glu Glu Asn Leu Val
        755                 760                 765

Phe Arg Val Glu Glu Gly Cys Ser Ala Tyr Ile His Gly Ala Ile Arg
    770                 775                 780

His Leu Ala Ile Ser Ser Asn Trp Lys Gly Asp Lys Ser Glu Phe Glu
785                 790                 795                 800

Gly Ile Val Asp Leu Ser Arg Ile Arg Ser Leu Ser Leu Phe Gly Asp
                805                 810                 815

Trp Lys Pro Phe Phe Val Tyr Gly Lys Met Arg Phe Ile Arg Val Leu
            820                 825                 830

Asp Phe Glu Gly Thr Arg Gly Leu Glu Tyr His His Leu Asp Gln Ile
```

-continued

```
        835                 840                 845

Trp Lys Leu Asn His Leu Lys Phe Leu Ser Leu Arg Gly Cys Tyr Arg
    850                 855                 860

Ile Asp Leu Leu Pro Asp Leu Leu Gly Asn Leu Arg Gln Leu Gln Met
865                 870                 875                 880

Leu Asp Ile Arg Gly Thr Tyr Val Lys Ala Leu Pro Lys Thr Ile Ile
                885                 890                 895

Lys Leu Gln Lys Leu Gln Tyr Ile His Ala Gly Arg Lys Thr Asp Tyr
            900                 905                 910

Val Trp Glu Glu Lys His Ser Leu Met Gln Arg Cys Arg Lys Val Gly
        915                 920                 925

Cys Ile Cys Ala Thr Cys Cys Leu Pro Leu Leu Cys Glu Met Tyr Gly
    930                 935                 940

Pro Leu His Lys Ala Leu Ala Arg Arg Asp Ala Trp Thr Phe Ala Cys
945                 950                 955                 960

Cys Val Lys Phe Pro Ser Ile Met Thr Gly Val His Glu Glu Glu Gly
                965                 970                 975

Ala Met Val Pro Ser Gly Ile Arg Lys Leu Lys Asp Leu His Thr Leu
            980                 985                 990

Arg Asn Ile Asn Val Gly Arg Gly Asn Ala Ile Leu Arg Asp Ile Gly
        995                 1000                1005

Met Leu Thr Gly Leu His Lys Leu Gly Val Ala Gly Ile Asn Lys Lys
    1010                1015                1020

Asn Gly Arg Ala Phe Arg Leu Ala Ile Ser Asn Leu Asn Lys Leu Glu
1025                1030                1035                1040

Ser Leu Ser Val Ser Ser Ala Gly Met Pro Gly Leu Cys Gly Cys Leu
                1045                1050                1055

Asp Asp Ile Ser Ser Pro Pro Glu Asn Leu Gln Ser Leu Lys Leu Tyr
            1060                1065                1070

Gly Ser Leu Lys Thr Leu Pro Glu Trp Ile Lys Glu Leu Gln His Leu
        1075                1080                1085

Val Lys Leu Lys Leu Val Ser Thr Arg Leu Leu Glu His Asp Val Ala
    1090                1095                1100

Met Glu Phe Leu Gly Glu Leu Pro Lys Val Glu Ile Leu Val Ile Ser
1105                1110                1115                1120

Pro Phe Lys Ser Glu Glu Ile His Phe Lys Pro Pro Gln Thr Gly Thr
                1125                1130                1135

Ala Phe Val Ser Leu Arg Val Leu Lys Leu Ala Gly Leu Trp Gly Ile
            1140                1145                1150

Lys Ser Val Lys Phe Glu Glu Gly Thr Met Pro Lys Leu Glu Arg Leu
        1155                1160                1165

Gln Val Gln Gly Arg Ile Glu Asn Glu Ile Gly Phe Ser Gly Leu Glu
    1170                1175                1180

Phe Leu Gln Asn Ile Asn Glu Val Gln Leu Ser Val Trp Phe Pro Thr
1185                1190                1195                1200

Asp His Asp Arg Ile Arg Ala Ala Arg Ala Ala Gly Ala Asp Tyr Glu
                1205                1210                1215

Thr Ala Trp Glu Glu Glu Val Gln Glu Ala Arg Arg Lys Gly Gly Glu
            1220                1225                1230

Leu Lys Arg Lys Ile Arg Glu Gln Leu Ala Arg Asn Pro Asn Gln Pro
        1235                1240                1245

Ile Ile Thr
    1250
```

<210> SEQ ID NO 17
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 17
gttgtttgag ctctccaatg cctgttc 27

<210> SEQ ID NO 18
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 18
ctgcagtgca atgtacggcc agg 23

<210> SEQ ID NO 19
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 19
agaggaagtg aatacacacc 20

<210> SEQ ID NO 20
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 20
gcaaactgag ctggagaag 19

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 21
tctatagaag tgcaaacagc 20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 22
ttaggtacga agatgagtag 20

<210> SEQ ID NO 23
<211> LENGTH: 19
<212> TYPE: DNA
<213> ORGANISM: Artificial Sequence
<220> FEATURE:

<223> OTHER INFORMATION: oligonucleotide primer

<400> SEQUENCE: 23
ggtttcccac tctcttaca 19

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
tctgttgctt ccacttcaac 20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 25
ttgaaagcga agaagacatt 20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 26
gacgaccaca tttatttaca 20

<210> SEQ ID NO 27
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 27
aacgaatcca tggcggagac 20

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
tgatatcatg aattcgacaa g 21

<210> SEQ ID NO 29
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 29
agttcaggaa aacactcgcc 20

<210> SEQ ID NO 30
<211> LENGTH: 20
<212> TYPE: DNA
<213> ORGANISM: Artificial sequence
<220> FEATURE:
<223> OTHER INFORMATION: oligonucleotide primer

<400> SEQUENCE: 30
ccatacctgt tttgcaggac 20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 31
cactgaataa cgactacatc 20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 32
cactgaataa cgactacatc 20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 33
attggtggtt gggcatctag 20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 34
tctatagaag tgcaaacagc 20

<210> SEQ ID NO 35
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 35
ttaggtacga acatgagtag 20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide primer -continued

<400> SEQUENCE: 36
tcattaagat taaggagccc 20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 37
catggttgct atattttagg 20

<210> SEQ ID NO 38
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 38
cactgttgta gcggaggaga 20

<210> SEQ ID NO 39
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 39
ttcgatggcg ttcaccaag 19

<210> SEQ ID NO 40
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 40
attccaacct gcagcaagag 20

<210> SEQ ID NO 41
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 41
attccaacct gcagcaagag 20

<210> SEQ ID NO 42
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 42
ttgaaagcga agaagacatt 20

<210> SEQ ID NO 43
<211> LENGTH: 21

-continued

```
<212> TYPE: DNA
<213> ORGANISM: Artificial Sequence
<220> FEATURE:
<223> OTHER INFORMATION: oligonucleotide primer

<400> SEQUENCE: 43

ggagcattat tcgatcatta g                                       21
```

CLONING AND CHARACTERIZATION OF THE BROAD-SPECTRUM RESISTANCE GENE PI2

CROSS-REFERENCE TO RELATED APPLICATIONS

This application is a continuation application of U.S. patent application Ser. No. 10/656,394, filed Sep. 5, 2003, which claims the benefit of U.S. Provisional Application Ser. No. 60/455,713, filed Mar. 18, 2003, and U.S. Provisional Application Ser. No. 60/409,216, filed Sep. 9, 2002, all of which are herein incorporated by reference.

FIELD OF THE INVENTION

The present invention relates generally to plant molecular biology. More specifically, it relates to nucleic acids and methods for modulating their expression in plants and to transforming genes into plants in order to enhance disease resistance.

BACKGROUND OF THE INVENTION

Rice blast, which is caused by the fungus *Magnaporthe grisea*, is one of the most devastating diseases in rice, and occurs in most rice growing areas worldwide. In terms of plant damage, rice blast commonly causes leaf blast during the vegetative phase of rice plant development, and infertility when plants are infected during the reproductive phase (panicle and node blast). This latter effect can result in dramatic yield and quality reductions, which are estimated to result in economic losses for farmers of nearly $5 billion per year (Moffat (1994) *Science* 265:1804-1805).

Because rice farmers generally have limited economic resources, control of rice blast is most often accomplished through the use of rice plant cultivars that exhibit a natural resistance to the disease. However, the disease resistance exhibited by these cultivars is generally unstable, with cultivars released as resistant showing susceptibility after only a few seasons of widespread cultivation. Despite this instability, the use of resistant cultivars remains the most economical and effective method of controlling rice blast disease. Consequently, there is a continued need for such disease-resistant cultivars.

Although resistant cultivars occur naturally, recent research has focused on genetic methods for creating or improving highly disease-resistant plants. Thus for the last four decades, rice geneticists and breeders have studied the genetics of blast resistance germplasm in order to develop the methods necessary to breed such durably resistant cultivars. Methods for the genetic analysis of resistance to blast originated in the early 1960s when Goto established the differential system for races of *M. grisea* in Japan (Ou (1985) *Rice Disease* $2^{nd}$ ed. (Commonwealth Mycological Institute, Slough, UK).

One blast resistance gene of particular importance is the Pi2 gene, which exhibits highly effective broad-spectrum resistance to a diverse population of blast disease isolates and, consequently, remains effective in a wide range of rice cultivation areas after over a decade of use. Although the location of this gene in the rice genome has been determined (Yu et al. (1991) *Theor. Appl. Genet.* 81:471-476; Liu et al. (2002) *Mol. Genet. Genom.* 267:472-480), its DNA sequence remains unknown. Because techniques for creating or improving disease resistance rely on the knowledge of such sequences, there is a great need for obtaining the actual DNA sequence of the Pi2 gene.

BRIEF SUMMARY OF THE INVENTION

Compositions and methods for creating or enhancing resistance to plant pests are provided. Compositions are nucleotide sequences for novel Pi2-like disease resistance gene homologues cloned from rice, and the amino acid sequences for the proteins or partial-length proteins or polypeptides encoded thereby. Methods of the invention involve stably transforming a plant with one of these novel disease resistance Pi2-like gene homologues operably linked with a promoter capable of driving expression of a nucleotide coding sequence in a plant cell. Expression of the novel nucleotide sequences confers disease resistance to a plant by interacting with the complementing phytopathogen avirulence gene product released into the plant by the invading plant pathogen. The methods of the invention find use in controlling plant pests, including fungal pathogens, viruses, nematodes, insects, and the like.

Transformed plants and seeds, as well as methods for making such plants and seeds are additionally provided.

BRIEF DESCRIPTION OF THE DRAWINGS

FIG. 5 shows a multiple protein sequence alignment between the predicted amino acid sequences of NBS1 (SEQ ID NO:2), NBS2 (SEQ ID NO:4), NBS4 (SEQ ID NO:8), NBS6 (SEQ ID NO:12) and the cloned blast resistance gene Pib (SEQ ID NO:16).

DETAILED DESCRIPTION OF THE INVENTION

Figure 1:
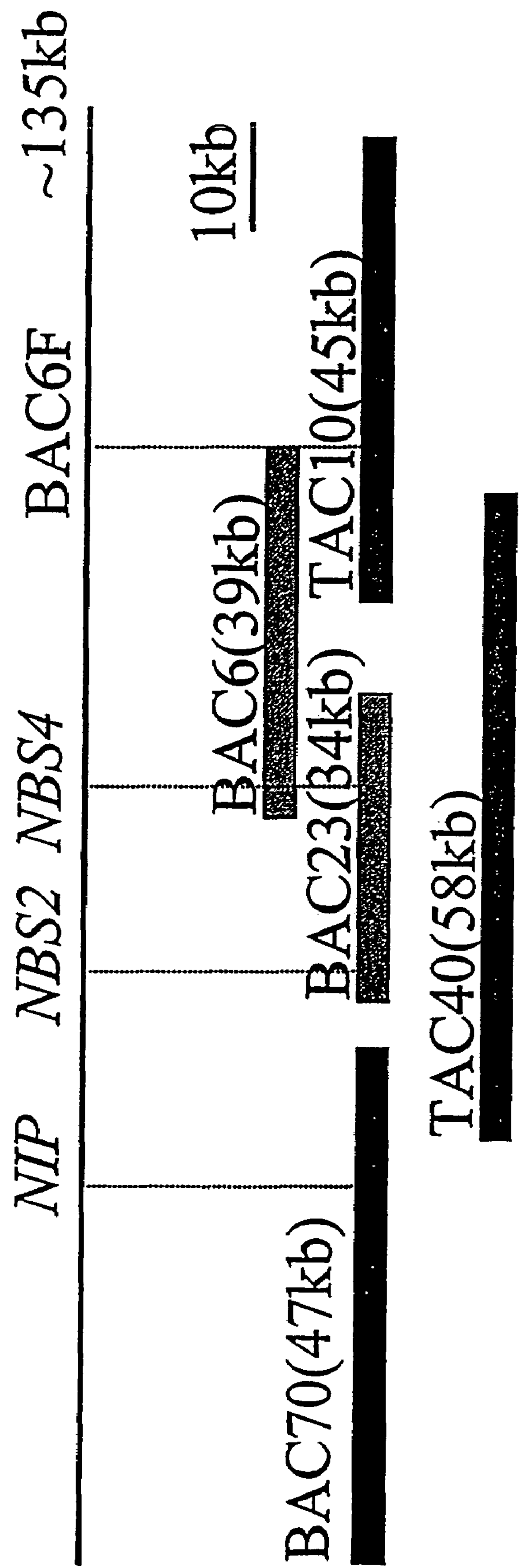
FIG. 1 shows a physical map of the Pi2 locus. The TAC and BAC clones are shown with bars. The BAC70, TAC40, and TAC 10 clones were used for sequencing. The positions of primers NIP, NBS2, NBS4, and BAC6F on the corresponding BAC and TAC clones are shown above the BAC/TAC contig.

Compositions of the invention include the Pi2 and related (Pi2-like) genes that are involved in disease resistance. In particular, the present invention provides for isolated nucleic acid molecules comprising nucleotide sequences encoding the amino acid sequences shown in SEQ ID NOs:2, 4, 6, 8, 10, and 12. Further provided are polypeptides having an amino acid sequence encoded by a nucleic acid molecule described herein, for example those set forth in SEQ ID NOs:1, 3, 5, 7, 9, and 11.

The present invention discloses the nucleotide sequences for NBS1-NBS6 as SEQ ID NOs:1, 3, 5, 7, 9, and 11, respectively. The present invention also discloses the corresponding amino acid sequences for NBS1-6 as SEQ ID NOs:2, 4, 6, 8, 10, and 12, respectively. SEQ ID NO:13 discloses the 99,090 bp contiguous sequence at the Pi2 region obtained in Example 3. SEQ ID NOs:14 and 15 correspond to cDNA-45 and cDNA-21 of Example 6, respectively; that is, to the two partially sequenced 3' fragments of the NBS4 gene that extend past the termination codon to include DNA sequence flanking the 3' end of the NBS4 gene.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence confer disease resistance. Alternatively, fragments of a nucleotide sequence that are useful as hybridization probes generally do not encode fragment proteins retaining biological activity to a plant. Thus, fragments of a nucleotide sequence may range from at least about 20 nucleotides, about 50 nucleotides, about 100 nucleotides, and up to the full-length nucleotide sequence encoding the proteins of the invention.

A fragment of a Pi2-like nucleotide sequence that encodes a biologically active portion of a Pi2-like polypeptide of the invention will encode at least 15, 25, 30, 50, 100, 150, 200, 250, 300, 350, 400, 450, 500, 550, 660, 650, 700, 750, 800, 850, 900, 950, or 1000 contiguous amino acids, or up to the total number of amino acids present in a full-length Pi2-like protein of the invention (for example, 993, 1032, 660, 1032, 49, and 998 amino acids for SEQ ID NOs:2, 4, 6, 8, 10, and 12, respectively). Fragments of a Pi2-like nucleotide sequence that are useful as hybridization probes or PCR primers generally need not encode a biologically active portion of a Pi2-like protein.

Thus, a fragment of a Pi2-like nucleotide sequence may encode a biologically active portion of a Pi2-like protein, or it may be a fragment that can be used as a hybridization probe or PCR primer using methods disclosed below. A biologically active portion of a Pi2-like protein can be prepared by isolating a portion of one of the Pi2-like nucleotide sequences of the invention, expressing the encoded portion of the Pi2-like protein (e.g., by recombinant expression in vitro), and assessing the activity of the encoded portion of the Pi2-like protein. Nucleic acid molecules that are fragments of a Pi2-like nucleotide sequence comprise at least 16, 20, 50, 75, 100, 150, 200, 250, 300, 350, 400, 450, 500,550, 600, 650, 700, 750, 800, 850, 900, 950, 1000,1150, 1200, 1250, 1300, 1350, 1400, 1450, 1500, 1550, 1660, 1650, 1700, 1750, 1800, 1850, 1900, 1950, 2000, 2150, 2200, 2250, 2300, 2350, 2400, 2450, 2500, 2550, 2660, 2650, 2700, 2750, 2800, 2850, 2900, 1950, 3000, or 3050 nucleotides, or up to the number of nucleotides present in a full-length Pi2-like nucleotide sequence disclosed herein (for example, 2982, 3099, 4147, 3099, 1389, and 2997 nucleotides for SEQ ID NOs:1, 3, 5, 7, 9, and 11, respectively).

By "variants" is intended substantially similar sequences. For nucleotide sequences, conservative variants include those sequences that, because of the degeneracy of the genetic code, encode the amino acid sequence of one of the Pi2-like polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a Pi2-like protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, Pi2-like activity as described herein. Such variants may result from, for example, genetic polymorphism or from human manipulation. Biologically active variants of a native Pi2-like protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters.

A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the Pi2-like proteins can be prepared by mutations in the DNA. Methods for mutagenesis and nucleotide sequence alterations are well known in the art. See, for example, Kunkel (1985) *Proc. Natl. Acad Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired Pi2-like activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated using assays such as are described in Liu et al. (2002) *Mol. Genet. and Genom.* 267:472-480, herein incorporated by reference.

Variant nucleotide sequences and proteins also encompass sequences and proteins derived from a mutagenic and recombinogenic procedure such as DNA shuffling. With such a procedure, one or more different Pi2-like coding sequences can be manipulated to create a new Pi2-like sequence coding for a Pi2-like polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Pi2-like gene of the invention and other known Pi2-like genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, including other monocots and dicots. In this manner, methods such as PCR, hybridization, and the like can be used to identify such sequences based on their sequence homology to the sequences set forth herein. Sequences isolated based on their sequence identity to the entire Pi2-like sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode a Pi2-like protein and which hybridize under stringent conditions to the Pi2-like nucleotide sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual (*2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the Pi2-like sequences of the invention. Methods for preparation of probes for hybridization and for construction of cDNA and genomic libraries are generally known in the art and are disclosed in Sambrook et al. (1989) *Molecular Cloning. A Laboratory Manual* (2d ed., Cold Spring Harbor Laboratory Press, Plainview, N.Y.).

For example, one of the entire Pi2-like sequences disclosed herein, or one or more portions thereof, may be used as a probe capable of specifically hybridizing to corresponding Pi2-like sequences and messenger RNAs. To achieve specific hybridization under a variety of conditions, such probes include sequences that are unique among Pi2-like sequences and are preferably at least about 10 nucleotides in length, and most preferably at least about 20 nucleotides in length. Such probes may be used to amplify corresponding Pi2-like sequences from a chosen plant by PCR. This technique may be used to isolate additional coding sequences from a desired plant or as a diagnostic assay to determine the presence of coding sequences in a plant.

One example of such a diagnostic assay is marker-aided selection. In this technique, a marker nucleotide sequence corresponding to a portion of the Pi2 gene can be used as a hybridization probe or as the basis for oligonucleotide primers to amplify nucleic acid, e.g., by PCR, from plants in order to screen the plant for the presence of the Pi2 gene. In one embodiment, this technique may be used to select for wild plants containing the Pi2 gene sequence. In another embodiment, the technique may be used to identify Pi2-containing plants resulting from crosses obtained in plant breeding programs. See, for example, Yu et al. (1991) *Theor. Appl. Genet.* 81:471-476, and Hittalmani et al. (2000) *Theor. Appl. Genet.* 100:1121-1128.

Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*;Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*;Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*;Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*;Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*;corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482;the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence Hencoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5√ C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The Pi2-like sequences of the invention are provided in expression cassettes for expression in the plant of interest. The cassette will include 5' and 3' regulatory sequences operably linked to a Pi2-like sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the Pi2-like sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a Pi2-like DNA sequence of the invention, and a transcriptional and translational termination region (i.e., termination region) functional in plants. The promoter may be native or analogous, or foreign or heterologous, to the plant host and/or to the Pi2-like DNA sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the Pi2-like DNA sequence of the invention, it is intended that the promoter is not the native or naturally occurring promoter for the operably linked Pi2-like DNA sequence of the invention. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of Pi2-like protein of the invention in the plant or plant cell. Thus, the phenotype of the plant or plant cell is altered.

The termination region may be native with the transcriptional initiation region, may be native with the operably linked Pi2-like DNA sequence of interest, may be native with the plant host, or may be derived from another source (i.e., foreign or heterologous to the promoter, the Pi2-like DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome.

The nucleic acids of the invention can be combined with constitutive, tissue-preferred, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of Pi2-like protein within a particular plant tissue. Tissue-preferred promoters include Yamamoto et al. (1997) *Plant J.* 12(2):255-265; Kawamata et al. (1997)

*Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112 (3):1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the-invention may be introduced into plants by contacting plants with a virus or viral nucleic acids. Generally, such methods involve incorporating a nucleotide construct of the invention within a viral DNA or RNA molecule. It is recognized that the a Pi2-like protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

The effects of transformation on the expression of the introduced Pi2-like gene of the invention may be assayed in a variety of ways. Differences in the expression of specific genes between, for example, an untransformed state and a transformed state where the plant now contains a Pi2-like gene may be determined using gene expression profiling. Total RNA or mRNA can be analyzed using the gene expression profiling process (GeneCalling®) as described in U.S. Pat. No. 5,871,697, herein incorporated by reference.

The following examples are offered by way of illustration and not by way of limitation.

EXPERIMENTAL

Summary

Recently, two resistance genes, Pib and Pi-ta, were successfully isolated. Pib was introgressed independently from two Indonesian and two Malaysian cultivars into various *Oviza sativa* spp. *japonica* cultivars (Yokoo et al. (1978) *Jpn. J. Breed* 28:359-385). The deduced amino acid sequence of the Pib gene contains a nucleotide binding site (NBS) and leucine-rich repeats (LRRs) (Wang et al. (1999) *Plant J.* 19:5 5-64), together a common feature of many cloned plant resistance genes (Bent (1996) *Plant Cell* 8:1757-1771). Interestingly, Pi-ta is similar to Pib as it contains a centrally localized nucleotide binding site and leucine-rich domain (LRD) at the C-terminus. AVR-Pi-ta (176) protein, which lacks the secretory and pro-protein sequences, can bind specifically to the LRD of the Pi-ta protein, both in the yeast two-hybrid system and in an in vitro binding assay, suggesting that the AVR-Pi-ta (176) protein binds directly to the Pi-ta LRD region inside the plant cell to initiate a Pi-ta-mediated defense response (Bryan (2000) *Plant Cell* 12:203 3-46; Jia et al. (2000) *EMBO J.* 19:4004-14). Comparison of the sequences of 6 resistant and 5 susceptible alleles of Pi-ta has revealed overall amino acid polymorphism with only one single amino acid determining specificity.

The Pi2 gene was introgressed from a highly resistant *O. sativa* spp. indica cultivar 5173 into the susceptible cultivar C039 and the derived isogenic line was named C101A51 (Mackill and Bonman (1992) *Phytopathology* 82:746-749). C101A51 was found to be resistant to over 200 isolates collected from different regions in the Philippines and susceptible to only a few isolates belonging to lineage 44 (Chen et al. (1996) *Rice Plant Dis.* 80:52-56). Extensive inoculation tests in several other countries also indicated that Pi2 is one of the most broad-spectrum blast resistance genes (H. Leung, International Rice Research Institute, IRRI). The Pi2 gene was mapped to rice chromosome 6 and found to be closely linked to the RFLP marker RG64 (2.1 cM) (Yu et al. (1991) *Theor. Appl. Genet.* 81:471-476). Pi9 was introgressed from the tetraploid wild rice *Oryza minuta* (BBCC genome) into the elite breeding line IR31917 (Amante-Bordeos et al. (1992) *Theor. Appl. Genet.* 84:345-354). The gene was also mapped on the chromosome 6 and is tightly linked to Pi2 (Liu et al. (2002) *Mol. Genet. and Genom.* 267:472-480). Using all of the Pi9 markers, a high-resolution map and BAC/TAC contig spanning at the Pi2 locus were constructed. Sequence analysis of a 99 kb fragment in the contig showed six NBS/LRR genes (NBS1-6) present in the region. Genetic and mutant analysis suggest that the one of the candidate genes, NBS2, is the Pi2 gene.

Example 1

High-resolution Mapping of the Pi2 Region Using Pi9 Linked Markers in a Large F2 Population To construct a high-resolution map at the Pi2 locus, over 2000 $F_2$ plants from a cross between the Pi2 isogenic line C101A51 and susceptible cultivar C039 were inoculated with blast isolate PO6-6. Seven days after inoculation, plants were scored for infection based on a 0-5 scoring system. A total of 505 plants with typical susceptible lesions were transplanted to pots in the greenhouse. Two weeks after the transplanting, a young leaf (3-4 cm long) was harvested from each plant for small-scale DNA extraction. DNA was extracted from all the susceptible plants. DNA quality and concentration were checked on agarose gel and adjusted to about 20 ng/μl with TE buffer. Two microliters of DNA were used for PCR amplification.

TABLE 1

Primer sequences used in the Pi2 mapping

| Marker | Name | Sequence | Reference |
|---|---|---|---|
| RG6 | 431 | GTT GTT TGA GCT CTC CAA TGC CTG TTC | Yu et al. 1991 |
| | 432 | CTG CAG TGC AAT GTA CGG CCA GG | |
| NBS1 | pi9-p5 | AGA GGA AGT GAA TAC ACA CC | |
| | pi9-p6 | GCA AAC TGA GCT GGA GAA G | |
| NBS2 | pi9-p9 | TCT ATA GAA GTG CAA ACA GC | |
| | pi9-p10 | TTA GGT ACG AAG ATG AGT AG | |
| NBS4 | NBS6-F1 | GGT TTC CCA CTC TCT TAC A | |
| | pi9-p12 | TCT GTT GCT TCC ACT TCA AC | |

Five pairs of primers (RG64 [431: SEQ ID NO:17 and 432: SEQ ID NO:18], NBS1 [pi9-p5: SEQ ID NO:19 and pi9-p6: SEQ ID NO:20], NBS2 [pi9-p9: SEQ ID NO:21 and pi9-pi10: SEQ ID NO:22], NBS4 [NBS6F1: SEQ ID NO:23 and NBS4 pi9-p12: SEQ ID NO:24, and NBS6) (Table 1) were designed based on the genomic sequence at the Pi9 region. These primers were first used to screen for polymorphism between C101A51 and CO39. NBS1 and NBS6 primers could not amplify a specific band from CO39 whereas NBS2 primers could only amplify a specific band from C101A51. NBS4 primers amplified bands from both C101A51 and CO39, but with different sizes of PCR product. For RG64 primers, a polymorphism was observed between the two parents only after digestion of the PCR product with the restriction enzyme HaeIII (Hittalmani et al. (1995) *Theor. Appl. Genet.* 100:1121-1128). Thus, we used NBS2, NBS4, and RG64 primers to screen a total of 505 susceptible plants. Fifteen recombinants were found at the RG64 locus, which is consistent with the RFLP mapping results of a 2.8 cM distance between the marker and the Pi2 gene (Yu et al. (1991) *Theor. Appl. Genet.* 81:471-476). Eight recombinants were identified in another 426 F2 plants between the RFLP marker R2131, indicating a distance of 2.7 cM from the Pi2 gene. No recombinants were found between Pi2 and either the NBS2 or NBS4 marker in the 505 susceptible plants. These results indicate that Pi2 is highly linked to both NBS2 and NBS4.

Example 2

Construction of a Pi2 BAC and a TAC Library

To construct a BAC and TAC library, high molecular weight (HMW) DNA was isolated from the Pi2 isogenic line C101A51 and was partially digested with restriction enzyme HindIII. The DNA was then size-fractionated (100-200 kb) using a pulse field gel electrophoresis device. Purified DNA from low-melting agarose was ligated to the HindIII-digested and dephosphorylated BAC and TAC vectors, respectively. The ligation mix was electroporated into *E. coli* DH10B cells using the Cell-Porator system. The average insert size of the two libraries was around 40 kb, since only one-size selection was performed for the partially digested DNA. Approximately 200,000 BAC clones and 150,000 TAC clones were collected and stored separately in 80 BAC pools (about 5000 clones per pool) and 45 TAC pools (about 3000 clones per pool). BAC/TAC plasmid DNA was isolated from each pool for PCR and Southern analysis.

Figure 2:
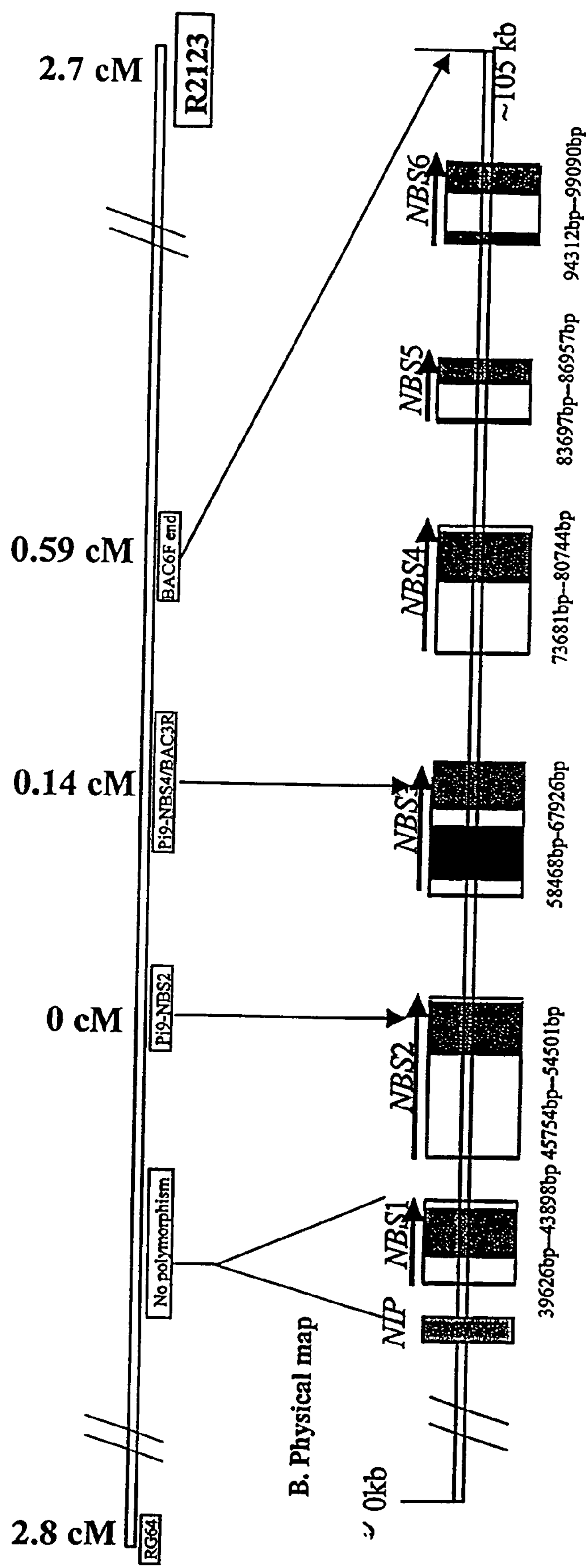
FIG. 2A, B shows genetic and physical maps of the Pi2 locus. A. The markers used in the Pi2 genetic mapping are shown in boxes, which are matched to the corresponding genomic sequence using arrows, and the genetic distance between the corresponding markers and Pi2 are shown above the markers. B. NBS/LRR gene cluster in the Pi2 region. The NIP gene that lies upstream to the NBS/LRR gene cluster is shown as the leftmost shaded box. The six NBS/LRR genes (NBS1-NBS6) have been named by the order of their occurrence in the genome sequence, and are shown as the six boxes of the figure labeled NBS1-NBS6, respectively. The transcription direction for each of these genes is shown with the arrow below the gene name. The exons of genes NBS1-NBS6 are shown as lightly shaded boxes; the darkly shaded box in the left-hand portion of the NBS3 gene represents the retroposon insert in this gene.

Three primer pairs (nitrate induced protein gene, and the NBS2 and NBS4 markers) were used to screen for positive BAC and TAC clones from the two libraries. Primers from the nitrate-induced protein gene were used as it lies upstream of the NBS gene cluster in the Pi9 sequence. Expected bands were amplified from three BAC pools and two TAC pools for the three primer pairs. After colony and Southern hybridization, three individual BACs (BAC6, 23, and 70) containing these three fragments were obtained. The two positive clones (TAC39 and TAC40) from the TAC library were confirmed to be the same clone and to overlap with BAC70, BAC23, and BAC6 according to their restriction digestion and Southern hybridization patterns. Furthermore, TAC10, which overlaps with TAC40 and BAC6 from the TAC library, was identified using the forward end of the BAC6 as probe for colony hybridization. According to an estimation from the HindIII and NotI-digested bands, the contiguous length of the whole contig is about 135 kb (FIG. 1). Among these clones, BAC70 was confirmed to contain the nitrate-induced protein gene, BAC23 contains the NBS2 and NBS4 markers, and BAC6 contains the NBS4 marker (FIG. 2A).

Example 3

Shotgun Libraries of the BAC and TAC Clones Spanning the Pi2 Locus

Based on the above results, three clones (BAC70, TAC40, TAC10) with minimum overlap were selected for sequencing using a shotgun method. The BAC and TAC DNA that were miniprepared using an ammonia-acetate precipitation method were sheared by sonication and repaired with T4 DNA polymerase. The repaired DNA was size-selected on agarose gel and purified using a GFX column (Amersham). The purified DNA was ligated to a SmaI-digested and dephosphorylated pBluescript-KS(+) vector. The ligation mix was electroporated into *E. coli* DH10B cells using the Cell-Porator system. The insert size of the three libraries was between 1.5 kb to 2.5 kb. White colonies were picked and stored in 96-well plates at −80° C. for sequencing. Around 900 individual clones from the TAC40 shotgun library and 700 individual clones from the BAC70 shotgun library were sequenced from both ends. The program phred/phrap/Consed was used to assemble all of the sequence data from both TAC40 and BAC70. Assembled sequence data indicated lengths of 58 kb for TAC40 and 46 kb for BAC70. The total length of the contiguous sequence at the Pi2 region was 99,090 bp (SEQ ID NO:13) after removal of the overlap sequence between the BAC70 and TAC40.

Example 4

NBS-LRR Homologous Gene Cluster in the Pi2 Sequence

To identify the open reading frame (ORF) accurately from the genomic sequence, two different approaches were used. First, the gene prediction program GenScan1.0 was used to obtain the skeleton of the coding sequence in the 99 kb region. Second, a homology search using the BLAST program was used to modify the gene prediction results. A resistant gene-like cluster downstream of the nitrate-induced protein (NIP) gene was identified in the 99 kb sequence. Six genes (named NBS1-NBS6), which are highly homologous to NBS/LRR type disease resistance genes cloned in plant species, were identified in the gene cluster (FIG. 2B). Among the six Pi2 candidate genes, NBS2 (SEQ ID NO:3) and NBS4 (SEQ ID NO:7) were confirmed with partial sequence of the relative cDNA. NBS3 (SEQ ID NO:5) is truncated by an insertion of a solo-LTR, which shows 86% identity in nucleotide sequence to the LTR of rice gypsy-type retrotransposon, RIRE8. This solo-LTR shows typical features including duplicated target sequences of GACCG and inverted repeat sequences of TGTCAC. It seems that NBS5 (SEQ ID NO:9) is another truncated gene since a large deletion was found in the coding sequence. NBS6 (SEQ ID NO:11) is at the right end of the sequence and extension of the sequence toward the right side is in progress.

Example 5

Sequence Comparison Analysis of the Six Pi2 Candidate Genes

The six putative NBS/LRR genes were translated into protein sequence. Since NBS3, NBS5, and NBS6 were either truncated or incomplete genes, the sequence comparison was done with the homologous fragments of those genes using the BLAST2 (Table 2). Among the six NBS/LRR genes, NBS2 shows 94% and 95% identities with NBS4 and NBS6, respectively. NBS4 and NBS6 show 97% identities to each other.

TABLE 2

Comparison of the amino acid sequence of the six NBS/LRR genes. The sequence identity and similarity were shown on the upper and lower, separately.

| | NBS2 | NBS3 | NBS4 | NBS5* | NBS6* |
|---|---|---|---|---|---|
| NBS1 | 62% | 61% | 62% | 45% | 60% |
| | 76% | 77% | 76% | 59% | 75% |
| NBS2 | | 63% | 93% | 42% | 94% |
| | | 77% | 94% | 57% | 95% |
| NBS3 | | | 62% | 53% | 63% |
| | | | 76% | 72% | 77% |
| NBS4 | | | | 43% | 97% |
| | | | | 57% | 97% |
| NBS5 | | | | | 76% |
| | | | | | 76% |

*Both NBS5 and NBS6 were compared with other genes using their nucleotide sequence since they are either truncated or incomplete.
**NBS5 and NBS6 were compared with their nucleotide sequence.

Example 6

Screening the cDNA of the Candidate Pi2 Gene

A cDNA library was constructed using RNA isolated from the leaf tissues 12 and 24 hours after infection with blast isolate PO6-6. Equal amounts of RNA from these two time points were mixed and used for mRNA purification. The purified mRNA was used to construct the cDNA library. The average size of the cDNA clones is 1.5 kb with size arranging from 0.7 kb to 2.8 kb after 20 individual clones were checked. The cDNA library was saved in 50 pools, totaling about 500,000 cDNA clones. Several candidate pools were identified by hybridization with the NBS2 marker as a probe to the EcoRI-digested plasmid DNA of each pool. cDNA-45 (SEQ ID NO:14) and cDNA-21 (SEQ ID NO:15) were finally identified using colony hybridization and matched to NBS4 with sequence confirmation.

Figure 3:
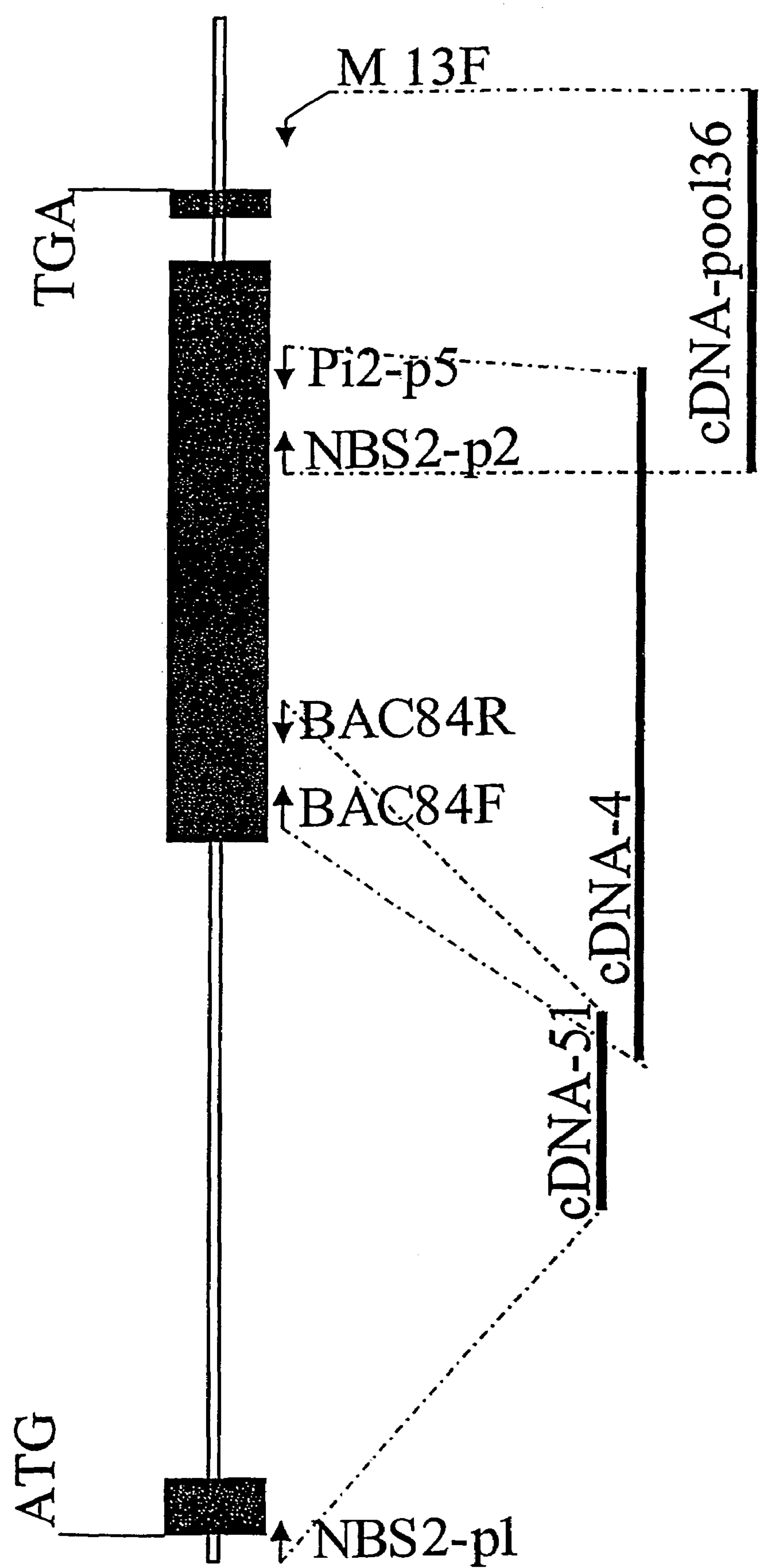
FIG. 3 shows a schematic diagram for cloning the complete coding sequences (CDS) of NBS2.

PCR amplification from the cDNA pools and RT-PCR were applied to clone the complete coding sequence of NBS2 and NBS4. Specific primers from both NBS2 and NBS4 were designed based on the genomic sequence of the Pi2 region (Table 3, FIG. 3). cDNA-f3 was obtained from cDNA pools with NBS2-p2 and M13 forward primers. cDNA-51, cDNA-52, and cDNA-4 were amplified using RT-PCR method with primer pairs of NBS2-p1/BAC84R and NBS2-p3/pi2-p5, separately. Sequencing of these cDNA confirmed that three of the cDNA clones (cDNA-f3, cDNA-51, and cDNA-4) matched the NBS2 gene and cDNA-52 matched to the NBS4 gene. The complete coding sequence of NBS2 was obtained by removing the overlap among these three cDNAs (cDNA-f3, cDNA-51, and cDNA-4). This sequence is presented as SEQ ID NO:3.

TABLE 3

Primer sequence used in cloning cDNA of NBS2 and NBS4

| Name | Sequence | SEQ ID NO |
|---|---|---|
| BAC84F1 | TTG AAA GCG AAG AAG ACA TT | SEQ ID NO: 25 |
| BAC84R1 | GAC GAC CAC ATT TAT TTA CA | SEQ ID NO: 26 |
| NBS2-p1 | AAC GAA TCC ATG GCG GAG AC | SEQ ID NO: 27 |
| NBS2-p2 | TGA TAT CAT GAA TTC GAC AAG | SEQ ID NO: 28 |
| NBS2-p3 | AGT TCA GGA AAA CAC TCG CC | SEQ ID NO: 29 |
| NBS2-p4 | CCA TAC CTG TTT TGC AGG AC | SEQ ID NO: 30 |
| NBS2-p5 | GGA GCA TTA TTC GAT CAT TAG | SEQ ID NO: 31 |

Example 7

Fine-mapping of the Pi2 Region with More Markers

Figure 4:
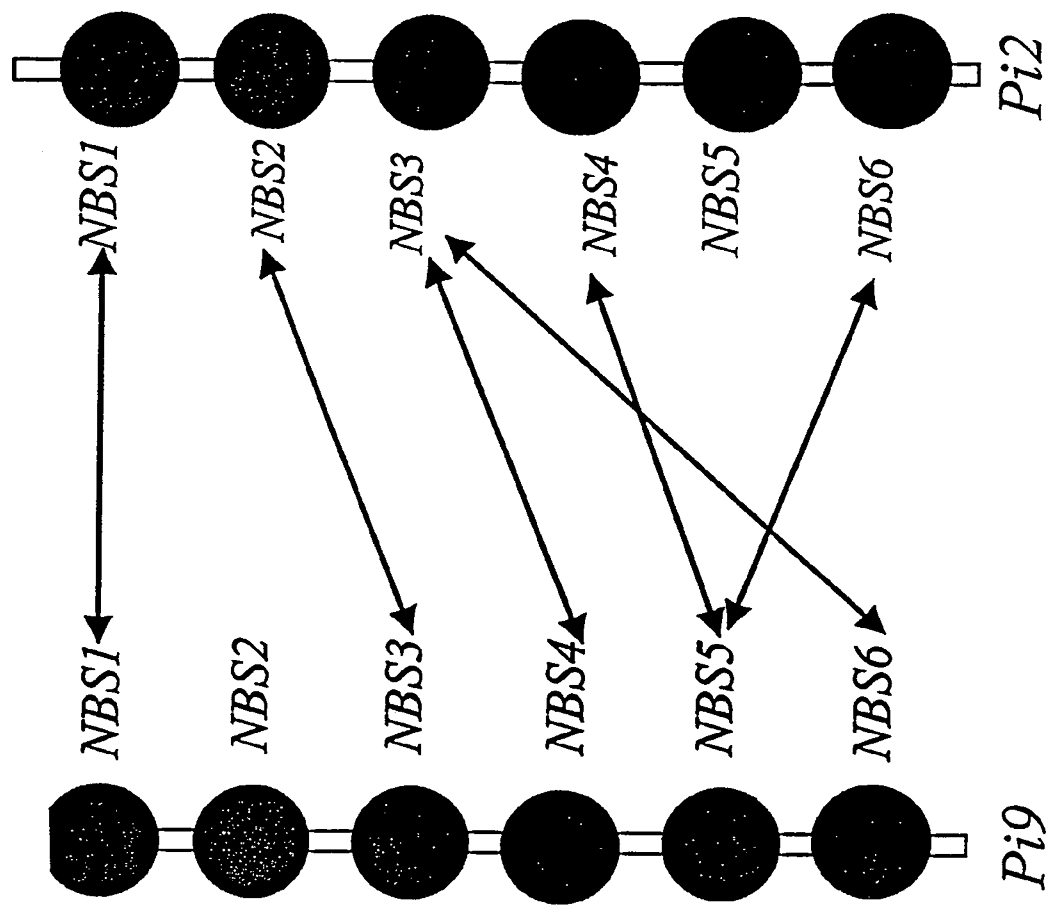
FIG. 4 shows an alignment of NBS/LRR genes at both Pi9 and Pi2 locus. The genomic sequence is identified with bold string and the NBS/LRR genes are identified with solid circles. The orthologous genes between Pi2 and Pi9 locus are shown with two-end arrow strings.
Figure 6:
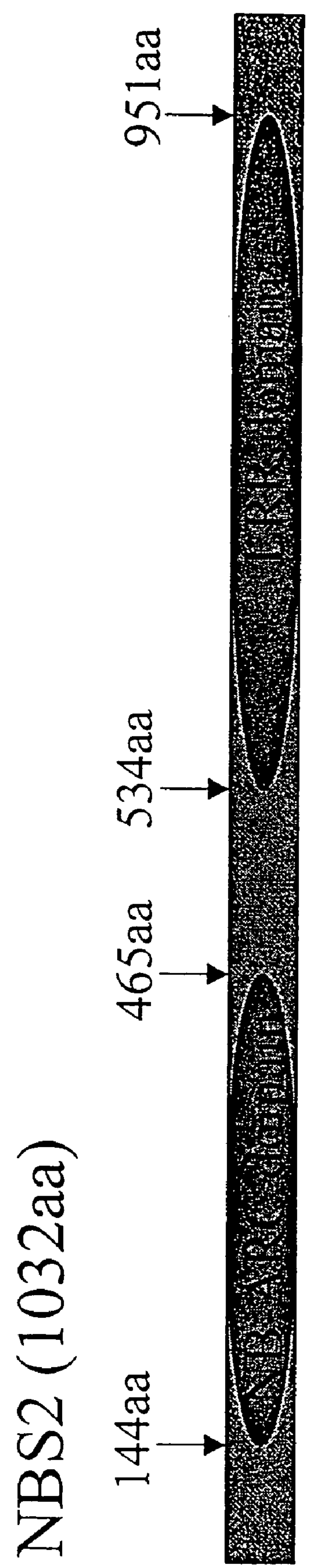
FIG. 6 shows conserved NB-ARC and LRR domains within the NBS2 (Pi2) gene. A NB-ARC domain is present in this gene from about amino acid 144 to about amino acid 465, while a LRR domain is present in this gene from about amino acid 534 to about amino acid 951.

A difference in the NBS/LRR gene alignment was found between Pi2 and Pi9 region (FIG. 4). The primers designed from NBS4, which were used for Pi2 genetic mapping, were confirmed to match to NBS3 in Pi2. Another marker, BAC3R end, from Pi9 was also matched to the same NBS3 gene in Pi2. There is only one copy of the NBS3 gene in the Pi2 region, a difference from Pi9. No recombinants were found between either NBS2 and NBS3 and Pi2 in 505 susceptible plants using PCR method. One recombinant was found between NBS3 and Pi2 in another 426 F2 plants using hybridization method. To determine the direction of Pi2 to NBS3, more PCR primer pairs were designed based on sequence from NBS1-NBS6 region. When the primer pair designed based on the sequence from BAC6 forward end was used to screen 505 susceptible plants, three recombinants were identified. The Pi2 gene should thus lie upstream to NBS3 since BAC6 forward end is downstream to NBS3. Together with the previous result that no polymorphism was found in the region upstream to NBS1, these results established that Pi2 is either NBS1 or NBS2, the only two genes between NIP and NBS3 in the Pi2 region (FIG. 2A).

Example 8

Mutant Generation from the Pi2 Plants

To accelerate cloning of the Pi2 gene, we generated mutant lines from Pi2-carrying cultivar C101A51. C101A51 seeds were treated with gamma rays and more than 10,000 M1 lines were collected. Individual M2 seeds were sowed in soil and inoculated with PO6-6 after 3 weeks. The plants with typical susceptible symptoms were transplanted to pots in the greenhouse. The DNA was extracted from each plant for PCR and Southern analysis after two weeks. Three specific primer pairs (Nip, NBS2, and BAC6 forward end) were used for PCR screening (Table 3). PCR analysis showed that the Nip gene was not deleted in every M2 plant while NBS2 and BAC6 forward end were lost in all susceptible mutant plants. Interestingly, two resistant plants in two different families (25-4 and 41-2) had no deletions within the three-targeted regions.

TABLE 4

Primer sequence for analysis of the mutant lines of C101A51

| Locus | Name | Sequence | |
|---|---|---|---|
| Nip | pi9-p4 | CAC TGA ATA ACG ACT ACA TC | SEQ ID NO: 32 |
| | pi9-p15 | ATT GGT GGT TGG GCA TCT AG | SEQ ID NO: 33 |
| Nbs2 | pi9-p9 | TCT ATA GAA GTG CAA ACA GC | SEQ ID NO: 34 |
| | pi9-p10 | TTA GGT ACG AAC ATG AGT AG | SEQ ID NO: 35 |
| BAC6F | BAC6F-1 | TCA TTA AGA TTA AGG AGC CC | SEQ ID NO: 36 |
| | BAC6F-2 | CAT GGT TGC TAT ATT TTA GG | SEQ ID NO: 37 |
| Nbs1 | NBS-LRR-F2 | CAC TGT TGT AGC GGA GGA GA | SEQ ID NO: 38 |
| | pi2-p2 | TTC GAT GGC GTT CAC CAA G | SEQ ID NO: 39 |
| Nbs2-5' | pi2-p8 | CCA ATG TCT GCA TAC TCT TC | SEQ ID NO: 40 |
| | pi2-p5 | ATT CCA ACC TGC AGC AAG AG | SEQ ID NO: 41 |
| Nbs2-3' | BAC84F | TTG AAA GCG AAG AAG ACA TT | SEQ ID NO: 42 |
| | pi2-p5 | GGA GCA TTA TTC GAT CAT TAG | SEQ ID NO: 43 |

Serial DNA probes were used for hybridization analysis to determine the deletion region in the susceptible mutants lines of C101A51 (Table 4). One region contains a fragment from 42361 bp to 45301 bp that spans from the 3' end of NBS1 to the promoter region of NBS2 (FIG. 2B). The same set of mutant plants used in PCR analysis was used in Southern analysis. When the NBS1 fragment was used as a probe, all susceptible and resistant mutants showed the same hybridization pattern with the wild-type resistant plant C101A51. The size of the two hybridizing bands was identical to ones determined from the restriction map of the sequence. However, the 3' region of the NBS2 gene, which is from 53221 bp and 54023 bp, was deleted in all susceptible M2 plants but not in resistant plants (FIG. 2B). The deletion site at the NBS2 gene region was determined using another NBS2 probe from 51894 bp and 54023 bp (FIG. 2B). Both the wild-type resistant plant C101A51 and resistant plants from mutant lines showed the same hybridization pattern: hybridizing bands identical in size to ones determined from the restriction map of the sequence. The susceptible plants from the mutant lines showed a smaller band of 1.6 kb without the band of 2.8 kb in the wild-type plant C101A51. It was deduced that the deletion site in the NBS2 gene was localized between 52891 bp and 55674 bp, which caused the band of 2.8 kb become to 1.6 kb. The fragment spanning the deletion region was also cloned using inverse PCR. The sequence of the deletion junction confirmed that the deletion region started in the middle of the NBS2 gene. Together with the PCR analysis result, it was deduced that the deletion region of the known mutants is between NBS2 and BAC6 forward end, and NBS1 is not one of the Pi2 candidate genes since it was intact in all susceptible mutant plants.

Combining high-resolution mapping and mutant analysis results, it has been concluded that NBS2 is the Pi2 candidate gene.

Example 9

Sequence Conservation between NBS-1 and Pib and Conserved Elements within NBS2 (Pi2)

In light of the six NBS genes NBS1-6 obtained in the preceding experiments, a multiple protein sequence alignment was performed between the predicted amino acid sequences obtained for these genes and the cloned blast resistance gene Pib. FIG. 4 shows the result of this alignment, which indicates regions of high sequence conservation.

Conserved elements within the NBS2 (Pi2) gene are also indicated in FIG. 10, which shows that a NB-ARC domain is present in this gene from about amino acid 144 to about amino acid 465, while a LRR domain is present in this gene from about amino acid 534 to about amino acid 951.

Example 10

Transformation and Regeneration of Transgenic Plants

Immature maize embryos from greenhouse donor plants are bombarded with a plasmid containing the Pi2-like DNA sequence of the invention operably linked to an appropriate promoter and the selectable marker gene PAT (Wohlleben et al. (1988) Gene 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the Pi2-like DNA operably linked to the appropriate promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for Pi2-like DNA activity.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.1 00 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6);

and 6 g/l bacto-agar (added after bringing to volume with polished D-I $H_2O$), sterilized and cooled to 60° C.

Example 11

*Agrobacterium*-mediated Transformation

For *Agrobacterium*-mediated transformation of maize with a Pi2-like gene of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the Pi2-like gene to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 12

Soybean Embryo Transformation

Soybean embryos are bombarded with a plasmid containing a Pi2-like gene of the invention operably linked to a suitable promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (*London*) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the Pi2-like gene operably linked to a suitable promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 13

Sunflower Meristem Tissue Transformation

Sunflower meristem tissues are transformed with an expression cassette containing a Pi2-like gene of the invention operably linked to a suitable promoter as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.* 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the Pi2-like gene operably linked to a suitable promoter is introduced into *Agrobacterium* strain EHA105 via freeze-thawing as described by Holsters et al. (1978) *Mol. Gen. Genet.* 163: 181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for Pi2-like protein activity, using assays such as are described in Liu et al. Mol. Gen. Genet. (2000) 267:472-480.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of To plants (parental generation) maturing in the greenhouse are identified by NPTII ELISA and/or by Pi2-like protein activity analysis of leaf extracts while transgenic seeds harvested from NPTII-positive To plants are identified by Pi2-like protein activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for Pi2-like protein activity using assays known in the art (see, for example assays such as are described in Liu et al. Mol. Gen. Genet. (2000) 267:472-480). After positive (i.e., for Pi2-like protein expression) explants are identified, those shoots that fail to exhibit Pi2-like protein activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for Pi2-like protein expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 14

Functional Analysis of Pi2 by Stable Rice Transformation

A TAC library with about 100,000 clones was made from the leaf tissue of the Pi2 carrying line C101A51. Several positive clones containing the Pi2 candidate gene sequences were identified. One of the clones, TAC40, was digested with AscI and self-ligated. A subclone, designed as C2 construct, containing a 32 kb fragment was obtained and used for transformation of the susceptible cultivar TP309 via *Agrobacterium*-mediated method. This fragment contains NBS2 and NBS3 as well as partial sequence of NBS1 and NBS4. A total of 12 independent T0 transgenic lines were developed and 4 lines were observed with a 3:1 segregation ratio (resistant to susceptible) to rice blast isolate PO-6-6 (data not shown). The resistant phenotype was also co-segregated perfectly with the Pi2 transgene in Southern blot analysis. With results from high resolution mapping, mutant and transgenic analyses, we concluded that NBS2 is the Pi2 gene.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of detecting the Pi2 locus in the genome of a plant or a part thereof comprising:

a) amplifying a fragment of DNA set forth in SEQ ID NO:13 from said plant or said plant part, wherein said fragment of DNA comprises a specific region linked to the genomic sequence of SEQ ID NO:7; and, b) identifying a plant having resistance to a Blast fungus.

2. The method of claim 1, wherein said fragment of DNA is between nucleotides 54203 to 67319 of SEQ ID NO:13.

3. The method of claim 2, wherein said fragment of DNA is between nucleotides 54203 to 56216 of SEQ ID NO:13.

4. The method of claim 3, wherein said fragment of DNA is amplified using a first primer comprising the sequence set forth in SEQ ID NO: 21 and a second primer comprising the sequence set forth in SEQ ID NO:22.

5. The method of claim 1, wherein the plant comprises a rice plant.

6. The method of claim 2, wherein said fragment of DNA is between nucleotides 64190 to 67319 of SEQ ID NO: 13.

7. The method of claim 6, wherein said fragment of DNA is amplified using a first primer comprising the sequence set forth in SEQ ID NO:23 and a second primer comprising the sequence set forth in SEQ ID NO: 24.

* * * * *